United States Patent
Rice et al.

(10) Patent No.: US 8,101,625 B2
(45) Date of Patent: Jan. 24, 2012

(54) PYRIMIDINONES AS CASEIN KINASE II (CK2) MODULATORS

(75) Inventors: Kenneth D. Rice, San Rafael, CA (US); Neel Kumar Anand, Burlingame, CA (US); Arlyn Arcalas, South San Francisco, CA (US); Charles M. Blazey, San Francisco, CA (US); Joerg Bussenius, Foster City, CA (US); Wai Ki Vicky Chan, San Francisco, CA (US); Hongwang Du, Millbrae, CA (US); Sergey Epshteyn, Fremont, CA (US); Mohamed Abdulkader Ibrahim, Mountain View, CA (US); Patrick Kearney, San Francisco, CA (US); Abigail R. Kennedy, Oakland, CA (US); Moon Hwan Kim, Palo Alto, CA (US); Jean-Claire Limun Manalo, Daly City, CA (US); Csaba J. Peto, Alameda, CA (US); Tsze H. Tsang, El Cerrito, CA (US); Amy Lew Tsuhako, Milpitas, CA (US); Peiwen Zhou, Palo Alto, CA (US); Elena S. Koltun, Foster City, CA (US)

(73) Assignee: Exelixis, Inc., South San Francisco, CA (US)

( * ) Notice: Subject to any disclaimer, the term of this patent is extended or adjusted under 35 U.S.C. 154(b) by 619 days.

(21) Appl. No.: 12/083,749

(22) PCT Filed: Oct. 23, 2006

(86) PCT No.: PCT/US2006/041505
§ 371 (c)(1),
(2), (4) Date: Jan. 22, 2009

(87) PCT Pub. No.: WO2007/048065
PCT Pub. Date: Apr. 26, 2007

(65) Prior Publication Data
US 2009/0215803 A1 Aug. 27, 2009

Related U.S. Application Data

(60) Provisional application No. 60/729,348, filed on Oct. 21, 2005.

(51) Int. Cl.
*A61K 31/505* (2006.01)
*C07D 239/02* (2006.01)
(52) U.S. Cl. .................................. 514/274; 544/316
(58) Field of Classification Search ................. 514/274; 544/316
See application file for complete search history.

(56) References Cited

U.S. PATENT DOCUMENTS 6,964,968 B2 * 11/2005 Giles et al. .................. 514/274
2005/0107413 A1   5/2005 Agarwal et al.

FOREIGN PATENT DOCUMENTS

| GB | 2 281 295 A | 3/1995 |
| JP | 06 298752 A | 10/1994 |
| WO | WO 2004/009560 A1 | 1/1929 |
| WO | WO 2005/013996 A2 | 2/2005 |

OTHER PUBLICATIONS

Pasha et al., 2005, CAS: 145:397448.*
Andotra et al., 2002, CAS: 138: 170177.*
Wasfy et al., 1996, CAS: 125: 300936.*
Fujisawa et al., 1985, CAS: 102: 95665.*
Bhat et al., 2001, CAS: 134: 280800.*
Ei-Gawad et al., 1999, CAS: 132: 166201.*
Amine's, 1999, CAS: 130: 311755.*
Thakar et al., 1984, CAS: 100: 121000.*
Thakar, K.A., et al., "Synthesis of some pyrimidine Derivatives," J. Indian Chem.. Soc., vol. 60, (1983) pp. 671-673.
Sabri, S. S., et al., "Reaction of alpha,beta-unsaturated ketones with urea. Synthesis and spectral properties of 2(1H)-pyrimidinone derivatives," J. Chem. Eng. Data, vol. 30, (1985), pp. 512-514.
Ruben, M., et al., "Supramolecular spintronic devices: spin transitions and magnetostructural correlations in $[Fe_4^{II}L_4]^{8+}$ [2×2]-grid-type complexes," Chem. Eur. J., vol. 9, (2003) pp. 4422-4429.
Sedova, V.F., et al., "Two directions of the reaction of 4-bromobenzaldehyde with substituted acetophenones and urea. Synthesis of aryl-substituted pyrimidin-2-one and hexahydropyrimido[4,5-d]pyrimidin-2,7-dione," Chemistry of Heterocyclic Compounds, vol. 40, No. 2, (2004), pp. 194-202.
Naik, S. K., et al., "Studies on Heterocyclic Compounds: Part III -4,6-disubstituted 5,6-dihydro-2(1H)pyrimidinethiones," Indian Journal of Chemistry, vol. 21B, (1982) pp. 1124-1125.
Yagai, S., et al., "Synthesis and noncovalent polymerization of self-complementary hydrogen-bonding supramolecular synthons: N, N'-disubstituted 4,6-diamino-pyrimidin-2(1H)-ones," Chem. Commun., (2004), pp. 1114-1115.
El-Hashash, M.A., et al., "A facile one-pot conversion of chalcones to pyrimidine derivatives and their microbial and antifungal activities," Indian Journal of Chemistry, vol. 32B, (1993), pp. 449-452.

(Continued)

Primary Examiner — Rei-tsang Shiao
(74) Attorney, Agent, or Firm — McDonnell Boehnen Hulbert & Berghoff LLP

(57) ABSTRACT

A compound having Formula (I) or a pharmaceutically acceptable salt thereof, wherein X, $R_1$ and $R_2$ are defined in the specification; pharmaceutical compositions thereof; and methods of use thereof.

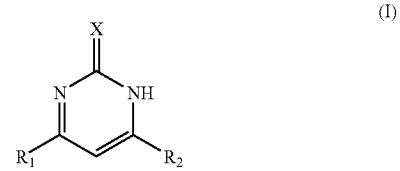

(I)

13 Claims, No Drawings

OTHER PUBLICATIONS

Essawy, S.A., et al., "Some reactions of 4-(2-methoxynaphthyl)-6-(p-chlorophenyl) pyrimidin-2 (1H)-one and its corresponding 2-chloro derivative," Egypt. J. Chem., vol. 37, No. 4, (1994), pp. 413-421.

Yassin, F.A., "Synthesis, properties and structure of thiopyrimidine derivatives," Egypt. J. Chem., vol. 46, No. 1, (2003), pp. 107-120.

Amine, M.S., "Utilities of 4-(4'-benzyl phenyl)-6-arylpyrimidine-2-thiones for the synthesis of biologically active condensed and non-condensed heterocycles," Egypt. J. Chem., vol. 41, (1998), pp. 267-276.

Soliman, F.M.A., et al., "Behavior of 4,6-diaryl-2(1H)-pyrimidin-2-thione towards some nucleophiles and eletrophiles," Revue Roumaine de Chimie, vol. 41, No. 1-2, (1996), pp. 109-117.

Al-farkh, Y.A., et al., "Synthesis and spectroscopic studies of some heterocyclic compounds," Chem. Pharm. Bull, vol. 26, (1978), pp. 1298-1303.

Baddar, F.G., et al., "Acetylenic ketones. Part V (1). Reaction of acetylenic ketones with thiourea and some of its derivatives," J. Heterocyclic Chem., vol. 15, (1978), pp. 105-112.

Ishibashi, M., et al., "Casein Kinase II Inhibitors Isolated from Two Brazilian Plants *Hymenaea parvifolia* and *Wulffia baccata*," Bioorganic & Medicinal Chemistry Letters, vol. 9, pp. 2157-2160, (1999).

\* cited by examiner

PYRIMIDINONES AS CASEIN KINASE II (CK2) MODULATORS

CROSS REFERENCE TO RELATE APPLICATIONS

This application claims priority to U.S. Provisional Application Ser. No. 60/729,348, filed Oct. 21, 2005.

BACKGROUND OF THE INVENTION

1. Field of the Invention

This invention relates to the field of protein kinases and inhibitors thereof. In particular, the invention relates to inhibitors of Casein kinase II (CK2) pathways.

2. Summary of the Related Art

Casein kinase II (CK2) is a highly conserved, ubiquitously expressed protein serine/threonine kinase that phosphorylates acidic proteins such as casein. It has a tetrameric $\alpha(2)/\beta(2)$ structure. The alpha subunit possesses catalytic activity, and the beta subunit is autophosphorylated in vitro. While consideration of CK2 as a tetrameric complex remains relevant, significant evidence has emerged to challenge the view that its individual subunits exist exclusively within these complexes (Bibby et al (2005) Int J Biol Sci. 1:67-79). Circumscribed as having a vast array of substrates located in a number of cellular compartments, CK2 has been implicated in critical cellular processes such as proliferation, apoptosis, differentiation, and transformation (Olsten et al (2004) Biochem Cell Biol. 82:681-93).

Thus, there is a need for novel compounds that specifically inhibit, regulate and/or modulate kinases, particularly Casein kinase II (CK2), in order to treat, prevent, and/or inhibit diseases and conditions that involve critical cellular processes such as proliferation, apoptosis, differentiation, and transformation, such as cancers.

SUMMARY OF THE INVENTION

The invention relates to compounds and pharmaceutical compositions of the compounds for inhibiting CK2.

One aspect of the invention relates to compounds that inhibit CK2 function. The compounds are exemplified by Formula I as described herein.

Another aspect of the invention relates to a pharmaceutical composition comprising a compound according Formula I and a pharmaceutically acceptable carrier, excipient, or diluent.

Another aspect of the invention relates to a method of inhibiting CK2 in a cell, comprising contacting the cell, in which inhibition of CK2 is desired, with a compound according to Formula I.

Another aspect of the invention relates to a method of inhibiting CK2 in a cell, comprising contacting a cell in which inhibition of CK2 is desired with a pharmaceutical composition comprising a compound according to Formula I and a pharmaceutically acceptable carrier, excipient, or diluent.

Another aspect of the invention relates to a method of treating a disease or condition that involves CK2 comprising administering to a patient, in need of said treatment, a compound according to Formula I.

Another aspect of the invention relates to a method of treating a disease or condition that involves CK2 comprising administering to a patient, in need of said treatment, a pharmaceutical composition comprising a compound according to Formula I and a pharmaceutically acceptable carrier, excipient, or diluent.

The disease or condition that can be treated by the compounds of Formula I, and the pharmaceutical compositions thereof, include cancer. Non-limiting examples of the types of cancer that can be treated include ovarian cancer, cervical cancer, breast cancer, colorectal cancer, or glioblastomas.

The foregoing only summarizes certain aspects of the invention and is not intended to be limiting in nature. These aspects and other aspects and embodiments are described more fully below.

DETAILED DESCRIPTION OF THE INVENTION

The first aspect of the invention relates to compounds of the Formula I:

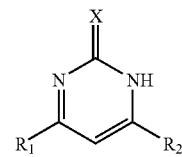

or a pharmaceutically acceptable salt thereof, wherein:

X is O or S;

$R_1$ is —$(C_5-C_{10})$aryl, —NH—$(C_5-C_{10})$aryl, pyrrol, pyridinyl, dihydropyridinyl or indole, wherein each —$(C_5-C_{10})$aryl, —NH—$(C_5-C_{10})$aryl, pyrrol, pyridinyl, dihydropyridinyl, and indole are optionally substituted with one or more groups independently selected from halo, —OH, —$(C_1-C_6)$alkyl, —$CF_3$, —$O(C_1-C_6)$alkyl$(C_5-C_{10})$aryl, —N—$(C_5-C_{10})$aryl, —$(C_1-C_6)$alkyl-$(C_5-C_{10})$aryl, —$O(C_1-C_6)$alkyl, —$O(C_1-C_6)$alkenyl, -(5-10 membered)heteroaryl, —$O(C_1-C_6)$aryl, —$(C_1-C_6)$alkoxy, —$(C_1-C_6)$alkoxy$(C_1-C_6)$alkoxy, —$O(C_1-C_6)$alkyl-$N[(C_1-C_6)$alkyl]$_2$, —$C(O)NH(C_1-C_6)$alkyl, —$C(O)NH(C_1-C_6)$alkyl-$N[(C_1-C_6)$alkyl]$_2$, —$C(O)NH(C_1-C_6)$alkyl-$NH_2$, —O—$(C_1-C_6)$alkyl-$C(O)NH(C_1-C_6)$alkyl-$(C_5-C_{10})$aryl, —$C(O)NH(C_1-C_6)$alkyl-O—$(C_1-C_6)$alkyl, —$C(O)$—N$[(C_1-C_6)$alkyl]$_2$-$N[(C_1-C_6)$alkyl]$_2$ and oxo;

$R_2$ is —$(C_5-C_{10})$aryl, —NH—$(C_5-C_{10})$aryl, pyrrol, pyridinyl, dihydropyridinyl or indole, wherein each —$(C_5-C_{10})$aryl, —NH—$(C_5-C_{10})$aryl, pyrrol, pyridinyl, dihydropyridinyl, and indole are optionally substituted with one or more groups independently selected from halo, —OH, —$(C_1-C_6)$alkyl, —$CF_3$, —$O(C_1-C_6)$alkyl$(C_5-C_{10})$aryl, —NH—$(C_5-C_{10})$aryl, —$(C_1-C_6)$alkyl-$(C_5-C_{10})$aryl, —$O(C_1-C_6)$alkyl, —$O(C_1-C_6)$alkenyl, -(5-10 membered)heteroaryl, —$O(C_1-C_6)$aryl, —$(C_1-C_6)$alkoxy, —$(C_1-C_6)$alkoxy$(C_1-C_6)$alkoxy, —$O(C_1-C_6)$alkyl-$N[(C_1-C_6)$alkyl]$_2$, —$C(O)NH(C_1-C_6)$alkyl, —$C(O)NH(C_1-C_6)$alkyl-$N[(C_1-C_6)$alkyl]$_2$, —$C(O)NH(C_1-C_6)$alkyl-$NH_2$, —O—$(C_1-C_6)$alkyl-$C(O)NH(C_1-C_6)$alkyl-$(C_5-C_{10})$aryl, —$C(O)NH(C_1-C_6)$alkyl-O—$(C_1-C_6)$alkyl, —$C(O)$—$N[(C_1-C_6)$alkyl]$_2$-$N[(C_1-C_6)$alkyl]$_2$ and oxo;

with the provisos that when one of $R_1$ or $R_2$ is phenyl, then the remaining $R_1$ or $R_2$ is not

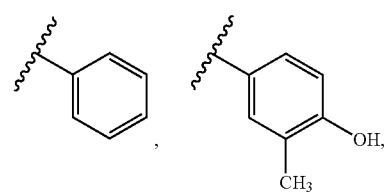

-continued

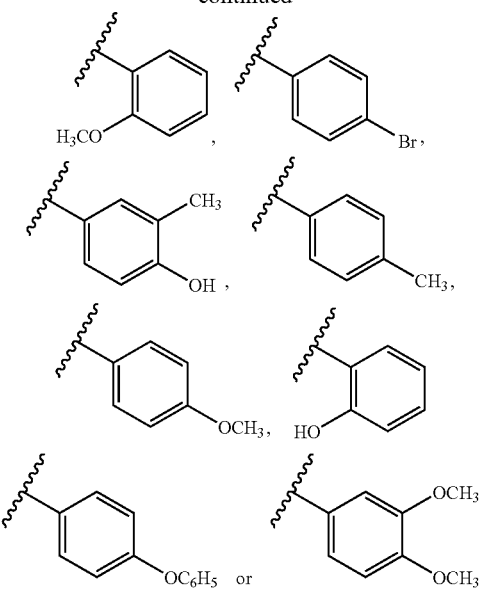

and when one of $R_1$ or $R_2$ is

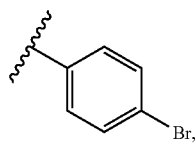

then the remaining $R_1$ or $R_2$ is not

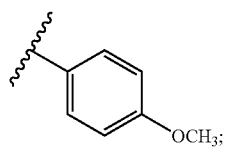

or one of $R_1$ or $R_2$ is

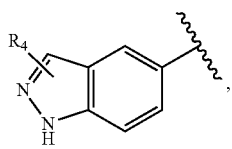

and the remaining $R_1$ or $R_2$ is

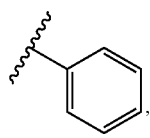

wherein $R_4$ is selected from hydrogen, halo, —OH, —$NH_2$, and —($C_1$-$C_6$)alkyl;

or one of $R_1$ or $R_2$ is an unsubstituted phenyl, and the remaining $R_1$ or $R_2$ is phenyl substituted with one —$NH_2$ and optionally one —($C_1$-$C_6$)alkyl.

In another embodiment,

X is O.

In another embodiment, $R_1$ is —($C_5$-$C_{10}$)aryl substituted with one or more groups independently selected from Cl, I, —OH, —($C_1$-$C_6$)alkyl, —$CF_3$, —O($C_1$-$C_6$)alkyl($C_5$-$C_{10}$)aryl, —($C_1$-$C_6$)alkyl-($C_5$-$C_{10}$)aryl, —O($C_1$-$C_6$)alkyl, —O($C_1$-$C_6$)alkenyl, -(5-10 membered)heteroaryl, —O($C_1$-$C_6$)aryl, —($C_1$-$C_6$)alkoxy, —($C_1$-$C_6$)alkoxy($C_1$-$C_6$)alkoxy, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)NH($C_1$-$C_6$)alkyl-$NH_2$, —O—($C_1$-$C_6$)alkyl-C(O)NH($C_1$-$C_6$)alkyl-($C_5$-$C_{10}$)aryl, —C(O)NH($C_1$-$C_6$)alkyl-O—($C_1$-$C_6$)alkyl, and —C(O)—N[($C_1$-$C_6$)alkyl]$_2$-N[($C_1$-$C_6$)alkyl]$_2$.

In another embodiment, $R_2$ is —($C_5$-$C_{10}$)aryl, substituted with one or more groups independently selected from —O($C_1$-$C_6$)alkyl($C_5$-$C_{10}$)aryl, —($C_1$-$C_6$)alkyl-($C_5$-$C_{10}$)aryl, —O($C_1$-$C_6$)alkyl, —O($C_1$-$C_6$)alkenyl, -(5-10 membered)heteroaryl, —O($C_1$-$C_6$)aryl, —$NH_2$, —($C_1$-$C_6$)alkoxy, —($C_1$-$C_6$)alkoxy($C_1$-$C_6$)alkoxy, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)NH($C_1$-$C_6$)alkyl-$NH_2$, —O—($C_1$-$C_6$)alkyl-C(O)NH($C_1$-$C_6$)alkyl-($C_5$-$C_{10}$)aryl, —C(O)NH($C_1$-$C_6$)alkyl-O—($C_1$-$C_6$)alkyl, and —C(O)—N[($C_1$-$C_6$)alkyl]$_2$-N[($C_1$-$C_6$)alkyl]$_2$.

In another embodiment, $R_2$ is —($C_5$-$C_{10}$)aryl, substituted in the ortho or meta positions with one or more groups independently selected from —O($C_1$-$C_6$)alkyl($C_5$-$C_{10}$)aryl, —($C_1$-$C_6$)alkyl-($C_5$-$C_{10}$)aryl, —O($C_1$-$C_6$)alkyl, —O($C_1$-$C_6$)alkenyl, -(5-10 membered)heteroaryl, —O($C_1$-$C_6$)aryl, —$NH_2$, —($C_1$-$C_6$)alkoxy, —($C_1$-$C_6$)alkoxy($C_1$-$C_6$)alkoxy, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)NH($C_1$-$C_6$)alkyl-$NH_2$, —O—($C_1$-$C_6$)alkyl-C(O)NH($C_1$-$C_6$)alkyl-($C_5$-$C_{10}$)aryl, —C(O)NH($C_1$-$C_6$)alkyl-O—($C_1$-$C_6$)alkyl, and —C(O)—N[($C_1$-$C_6$)alkyl]$_2$-N[($C_1$-$C_6$)alkyl]$_2$.

In another embodiment, $R_2$ is phenyl substituted with both Br and —$CH_3$ or both Br and —$OCH_3$.

In another embodiment, $R_1$ is —($C_5$-$C_{10}$)aryl substituted with one or more groups independently selected from —OH and —($C_1$-$C_6$)alkyl.

In another embodiment, $R_2$ is —($C_5$-$C_{10}$)aryl substituted with one or more groups independently selected from —O($C_1$-$C_6$)alkyl-OH, —O($C_1$-$C_6$)alkyl, —O($C_1$-$C_6$)alkenyl, —($C_1$-$C_6$)alkoxy($C_1$-$C_6$)alkoxy, —O($C_1$-$C_6$)alkyl-(5-10 membered)heteroaryl, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)—N[($C_1$-$C_6$)alkyl]$_2$, —N[($C_1$-$C_6$)alkyl]$_2$, —C(O)NH($C_1$-$C_6$)alkyl-O—($C_1$-$C_6$)alkyl, and —C(O)NH($C_1$-$C_6$)alkyl-N[($C_1$-$C_6$)alkyl]$_2$.

In another embodiment, $R_2$ is —($C_5$-$C_{10}$)aryl substituted in the ortho or meta positions with one or more groups independently selected from —O($C_1$-$C_6$)alkyl-OH, —O($C_1$-$C_6$)alkyl, —O($C_1$-$C_6$)alkenyl, —($C_1$-$C_6$)alkoxy($C_1$-$C_6$)alkoxy, —O($C_1$-$C_6$)alkyl-(5-10 membered)heteroaryl, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)—N

[(C$_1$-C$_6$)alkyl]$_2$-N[(C$_1$-C$_6$)alkyl]$_2$, —C(O)NH(C$_1$-C$_6$) alkyl-O—(C$_1$-C$_6$)alkyl, and —C(O)NH(C$_1$-C$_6$)alkyl-N [(C$_1$-C$_6$)alkyl]$_2$.

In another embodiment, R$_1$ is

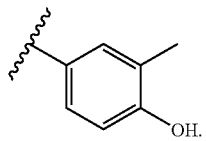

In another embodiment,

R$_2$ is phenyl substituted with one or more groups independently selected from —O(C$_1$-C$_3$)alkyl-OH, —O(C$_1$-C$_6$) alkyl, —O(C$_1$-C$_3$)alkenyl, —(C$_1$-C$_3$)alkoxy(C$_1$-C$_3$) alkoxy, —O(C$_1$-C$_3$)alkyl-(5-6 membered)heteroaryl, —O(C$_1$-C$_3$)alkyl-N[(C$_1$-C$_3$)alkyl]$_2$, —C(O)NH(C$_1$-C$_3$)alkyl, —C(O)NH(C$_1$-C$_3$)alkyl-N[(C$_1$-C$_3$)alkyl]$_2$, —C(O)—N[(C$_1$-C$_3$)alkyl]$_2$-N[(C$_1$-C$_3$)alkyl]$_2$, —C(O) NH(C$_1$-C$_3$)alkyl-O—(C$_1$-C$_3$)alkyl, and —C(O)NH(C$_1$-C$_3$)alkyl-N[(C$_1$-C$_6$)alkyl]$_2$.

In another embodiment,

R$_2$ is phenyl substituted in the ortho or meta positions with one or more groups independently selected from —O(C$_1$-C$_3$)alkyl-OH, —O(C$_1$-C$_6$)alkyl, —O(C$_1$-C$_3$)alkenyl, —(C$_1$-C$_3$)alkoxy(C$_1$-C$_3$)alkoxy, —O(C$_1$-C$_3$)alkyl-(5-6 membered)heteroaryl, —O(C$_1$-C$_3$)alkyl-N[(C$_1$-C$_3$)alkyl]$_2$, —C(O)NH(C$_1$-C$_3$)alkyl, —C(O)NH(C$_1$-C$_3$)alkyl-N[(C$_1$-C$_3$)alkyl]$_2$, —C(O)—N[(C$_1$-C$_3$)alkyl]$_2$-N[(C$_1$-C$_3$)alkyl]$_2$, —C(O)NH(C$_1$-C$_3$)alkyl-O—(C$_1$-C$_3$)alkyl, and —C(O)NH(C$_1$-C$_3$)alkyl-N[(C$_1$-C$_6$)alkyl]$_2$.

In another embodiment,

X is O;

R$_1$ is —(C$_5$-C$_{10}$)aryl substituted with one or more groups independently selected from Cl, I, —OH, —(C$_1$-C$_6$)alkyl, —CF$_3$, —O(C$_1$-C$_6$)alkyl(C$_5$-C$_{10}$)aryl, —(C$_1$-C$_6$)alkyl-(C$_5$-C$_{10}$)aryl, —O(C$_1$-C$_6$)alkyl, —O(C$_1$-C$_6$)alkenyl, -(5-10 membered)heteroaryl, —O(C$_1$-C$_6$)aryl, —(C$_1$-C$_6$) alkoxy, —(C$_1$-C$_6$)alkoxy(C$_1$-C$_6$)alkoxy, —O(C$_1$-C$_6$) alkyl-N[(C$_1$-C$_6$)alkyl]$_2$, —C(O)NH(C$_1$-C$_6$)alkyl, —C(O) NH(C$_1$-C$_6$)alkyl-N[(C$_1$-C$_6$)alkyl]$_2$, —C(O)NH(C$_1$-C$_6$) alkyl-NH$_2$, —O—(C$_1$-C$_6$)alkyl-C(O)NH(C$_1$-C$_6$)alkyl-(C$_5$-C$_{10}$)aryl, —C(O)NH(C$_1$-C$_6$)alkyl-O—(C$_1$-C$_6$)alkyl, and —C(O)—N[(C$_1$-C$_6$)alkyl]$_2$-N[(C$_1$-C$_6$)alkyl]$_2$;

R$_2$ is —(C$_5$-C$_{10}$)aryl, substituted with one or more groups independently selected from —O(C$_1$-C$_6$)alkyl(C$_5$-C$_{10}$) aryl, —(C$_1$-C$_6$)alkyl-(C$_5$-C$_{10}$)aryl, —O(C$_1$-C$_6$)alkyl, —O(C$_1$-C$_6$)alkenyl, -(5-10 membered)heteroaryl, —O(C$_1$-C$_6$)aryl, —NH$_2$, —(C$_1$-C$_6$)alkoxy, —(C$_1$-C$_6$) alkoxy(C$_1$-C$_6$)alkoxy, —O(C$_1$-C$_6$)alkyl-N[(C$_1$-C$_6$) alkyl]$_2$, —C(O)NH(C$_1$-C$_6$)alkyl, —C(O)NH(C$_1$-C$_6$) alkyl-N[(C$_1$-C$_6$)alkyl]$_2$, —C(O)NH(C$_1$-C$_6$)alkyl-NH$_2$, —O—(C$_1$-C$_6$)alkyl-C(O)NH(C$_1$-C$_6$)alkyl-(C$_5$-C$_{10}$)alkyl, —C(O)NH(C$_1$-C$_6$)alkyl-O—(C$_1$-C$_6$)alkyl, and —C(O)—N[(C$_1$-C$_6$)alkyl]$_2$-N[(C$_1$-C$_6$)alkyl]$_2$; or R$_2$ is —(C$_5$-C$_{10}$)aryl substituted with both Br and —CH$_3$ or both Br and —OCH$_3$;

or R$_1$ is an unsubstituted phenyl; and R$_2$ is phenyl substituted with one —NH$_2$ and optionally one —(C$_1$-C$_6$)alkyl.

In another embodiment,

X is O;

R$_1$ is —(C$_5$-C$_{10}$)aryl substituted with one or more groups independently selected from —OH and —(C$_1$-C$_6$)alkyl; and R$_2$ is —(C$_5$-C$_{10}$)aryl substituted with one or more groups independently selected from —O(C$_1$-C$_6$)alkyl-OH, —O(C$_1$-C$_6$)alkyl, —O(C$_1$-C$_6$)alkenyl, —(C$_1$-C$_6$)alkoxy (C$_1$-C$_6$)alkoxy, —O(C$_1$-C$_6$)alkyl-(5-10 membered)heteroaryl, —O(C$_1$-C$_6$)alkyl-N[(C$_1$-C$_6$)alkyl]$_2$, —C(O)NH (C$_1$-C$_6$)alkyl, —C(O)NH(C$_1$-C$_6$)alkyl-N[(C$_1$-C$_6$)alkyl]$_2$, —C(O)—N[(C$_1$-C$_6$)alkyl]$_2$-N[(C$_1$-C$_6$)alkyl]$_2$, —C(O) NH(C$_1$-C$_6$)alkyl-O—(C$_1$-C$_6$)alkyl, and —C(O)NH(C$_1$-C$_6$)alkyl-N[(C$_1$-C$_6$)alkyl]$_2$; or R$_2$ is —(C$_5$-C$_{10}$)aryl substituted with both Br and —CH$_3$ or both Br and —OCH$_3$.

In another embodiment, X is O;

R$_1$ is

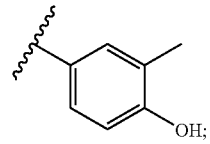

and

R$_2$ is phenyl substituted with one or more groups independently selected from —O(C$_1$-C$_3$)alkyl-OH, —O(C$_1$-C$_6$) alkyl, —O(C$_1$-C$_3$)alkenyl, —(C$_1$-C$_3$)alkoxy(C$_1$-C$_3$) alkoxy, —O(C$_1$-C$_3$)alkyl-(5-6 membered)heteroaryl, —O(C$_1$-C$_3$)alkyl-N[(C$_1$-C$_3$)alkyl]$_2$, —C(O)NH(C$_1$-C$_3$) alkyl, —C(O)NH(C$_1$-C$_3$)alkyl-N[(C$_1$-C$_3$)alkyl]$_2$, —C(O)—N[(C$_1$-C$_3$)alkyl]$_2$-N[(C$_1$-C$_3$)alkyl]$_2$, —C(O) NH(C$_1$-C$_3$)alkyl-O—(C$_1$-C$_3$)alkyl, and —C(O)NH(C$_1$-C$_3$)alkyl-N[(C$_1$-C$_6$)alkyl]$_2$.

In another embodiment, one of R$_1$ or R$_2$ is phenyl substituted with —OCH$_3$ and —OH.

In another embodiment, one of R$_1$ or R$_2$ is phenyl substituted with Cl and —OH.

In another embodiment, one of R$_1$ or R$_2$ is phenyl substituted with —O—(CH$_2$)$_2$—O—CH$_3$.

In another embodiment, one of R$_1$ or R$_2$ is phenyl substituted with —O—(CH$_2$)$_2$CH(CH$_3$)$_2$.

In another embodiment, one of R$_1$ or R$_2$ is phenyl substituted with —NH—CH$_2$—NH—CH$_2$CH$_3$.

Another aspect of the invention relates to a pharmaceutical composition comprising a compound according to Formula I and a pharmaceutically acceptable carrier, excipient, or diluent.

Another aspect of the invention relates to a method of inhibiting CK2 in a cell, comprising contacting a cell in which inhibition of CK2 is desired with a compound according to Formula I, or a pharmaceutically acceptable salt thereof.

Another aspect of the invention relates to a method of inhibiting CK2 in a cell, comprising contacting a cell in which inhibition of CK2 is desired with a pharmaceutical composition comprising a compound according to Formula I and a pharmaceutically acceptable carrier, excipient, or diluent.

Another aspect of the invention relates to a method of treating a disease or condition that involves CK2 comprising administering to a patient, in need of the treatment, a compound according to Formula I, or a pharmaceutically acceptable salt thereof. Non-limiting examples of the disease or condition that can be treated include cancer such as ovarian cancer, cervical cancer, breast cancer, colorectal cancer, or glioblastomas.

Another aspect of the invention relates to a method of treating a disease or condition that involves CK2 comprising administering to a patient, in need of the treatment, a pharmaceutical composition comprising a compound according to Formula I and a pharmaceutically acceptable carrier, excipient, or diluent. Non-limiting examples of the disease or condition that can be treated include cancer such as ovarian cancer, cervical cancer, breast cancer, colorectal cancer, or glioblastomas.

Table 1 illustrates some examples of the compounds of the invention. The examples in Table 1 are merely illustrative, and do not limit the scope of the invention in any way.

TABLE 1

| Cpd. No. | Structure | IUPAC Name | MS |
| --- | --- | --- | --- |
| 1 | 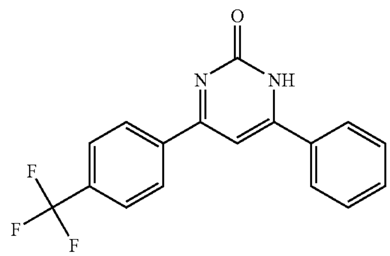 | 6-phenyl-4-[4-(trifluoromethyl)phenyl]pyrimidin-2(1H)-one | 317 |
| 2 | 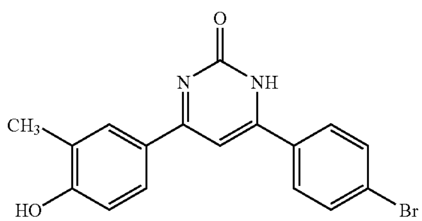 | 6-(4-bromophenyl)-4-(4-hydroxy-3-methylphenyl)pyrimidin-2(1H)-one | 358 |
| 3 | 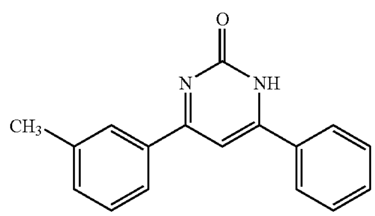 | 4-(3-methylphenyl)-6-phenylpyrimidin-2(1H)-one | 263 |
| 4 | 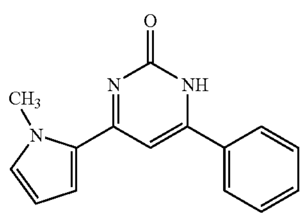 | 4-(1-methyl-1H-pyrrol-2-yl)-6-phenylpyrimidin-2(1H)-one | 252 |
| 5 | 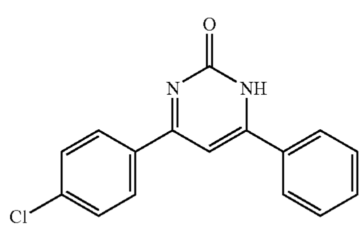 | 4-(4-chlorophenyl)-6-phenylpyrimidin-2(1H)-one | 283 |
| 6 | 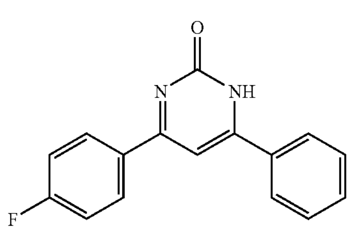 | 4-(4-fluorophenyl)-6-phenylpyrimidin-2(1H)-one | 267 |

TABLE 1-continued

| Cpd. No. | Structure | IUPAC Name | MS |
|---|---|---|---|
| 7 | 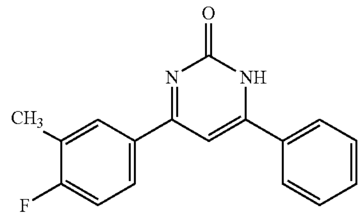 | 4-(4-fluoro-3-methylphenyl)-6-phenylpyrimidin-2(1H)-one | 281 |
| 8 | 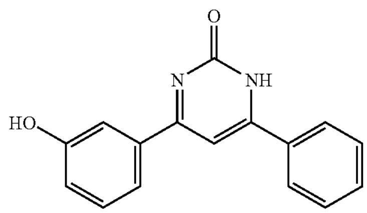 | 4-(3-hydroxyphenyl)-6-phenylpyrimidin-2(1H)-one | 265 |
| 9 | 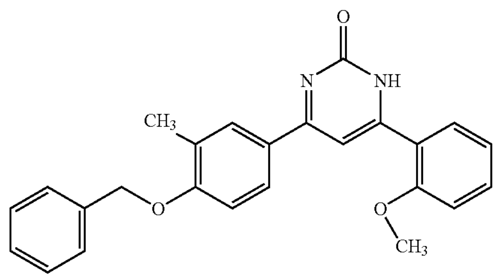 | 6-[2-(methyloxy)phenyl]-4-{3-methyl-4-[(phenylmethyl)oxy]phenyl}pyrimidin-2(1H)-one | 399 |
| 10 | 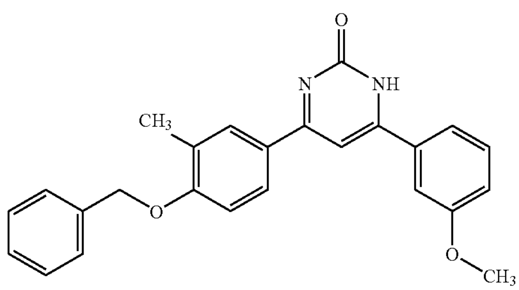 | 6-[3-(methyloxy)phenyl]-4-{3-methyl-4-[(phenylmethyl)oxy]phenyl}pyrimidin-2(1H)-one | 399 |
| 11 | 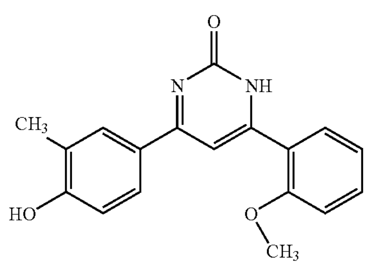 | 4-(4-hydroxy-3-methylphenyl)-6-[2-(methyloxy)phenyl]pyrimidin-2(1H)-one | 309 |
| 12 | 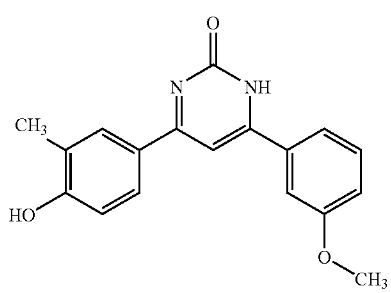 | 4-(4-hydroxy-3-methylphenyl)-6-[3-(methyloxy)phenyl]pyrimidin-2(1H)-one | 309 |

TABLE 1-continued

| Cpd. No. | Structure | IUPAC Name | MS |
|---|---|---|---|
| 13 | 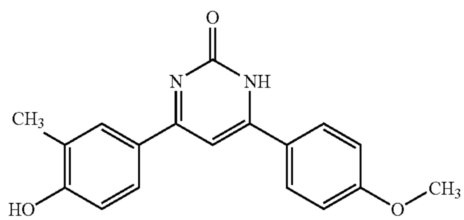 | 4-(4-hydroxy-3-methylphenyl)-6-[4-(methyloxy)phenyl]pyrimidin-2(1H)-one | 309 |
| 14 | 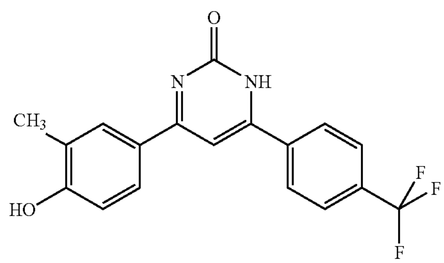 | 4-(4-hydroxy-3-methylphenyl)-6-[4-(trifluoromethyl)phenyl]pyrimidin-2(1H)-one | 347 |
| 15 | 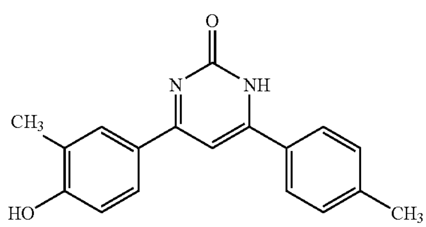 | 4-(4-hydroxy-3-methylphenyl)-6-(4-methylphenyl)pyrimidin-2(1H)-one | 293 |
| 16 | 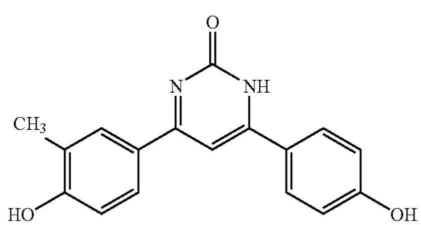 | 4-(4-hydroxy-3-methylphenyl)-6-(4-hydroxyphenyl)pyrimidin-2(1H)-one | 295 |
| 17 | 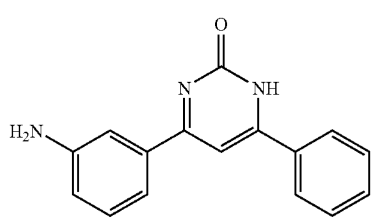 | 4-(3-aminophenyl)-6-phenylpyrimidin-2(1H)-one | 264 |
| 18 | 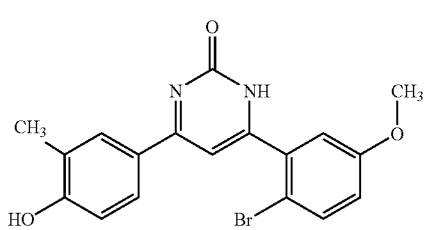 | 6-[2-bromo-5-(methyloxy)phenyl]-4-(4-hydroxy-3-methylphenyl)pyrimidin-2(1H)-one | 389 |
| 19 | 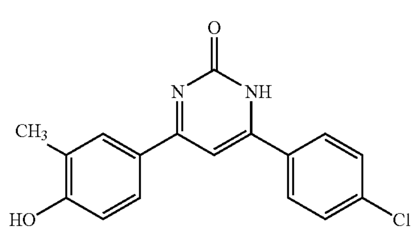 | 6-(4-chlorophenyl)-4-(4-hydroxy-3-methylphenyl)pyrimidin-2(1H)-one | 313 |

TABLE 1-continued

| Cpd. No. | Structure | IUPAC Name | MS |
|---|---|---|---|
| 20 | 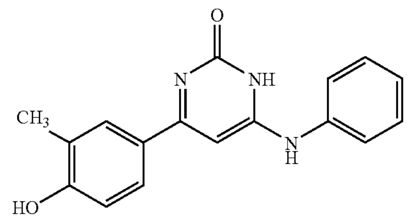 | 4-(4-hydroxy-3-methylphenyl)-6-(phenylamino)pyrimidin-2(1H)-one | 294 |
| 21 | 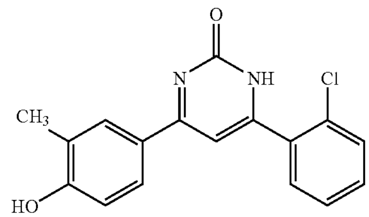 | 6-(2-chlorophenyl)-4-(4-hydroxy-3-methylphenyl)pyrimidin-2(1H)-one | 313 |
| 22 | 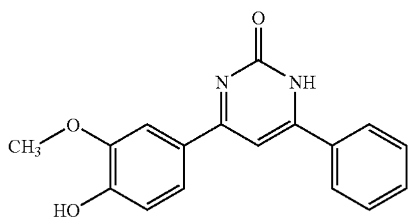 | 4-[4-hydroxy-3-(methyloxy)phenyl]-6-phenylpyrimidin-2(1H)-one | 295 |
| 23 | 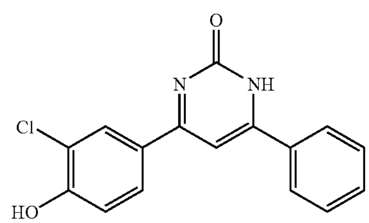 | 4-(3-chloro-4-hydroxyphenyl)-6-phenylpyrimidin-2(1H)-one | 299 |
| 24 | 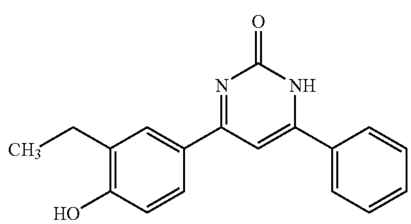 | 4-(3-ethyl-4-hydroxyphenyl)-6-phenylpyrimidin-2(1H)-one | 293 |
| 25 | 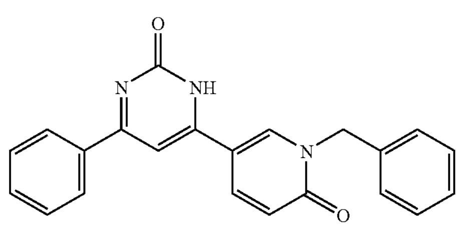 | 6-[6-oxo-1-(phenylmethyl)-1,6-dihydropyridin-3-yl]-4-phenylpyrimidin-2(1H)-one | 356 |
| 26 | 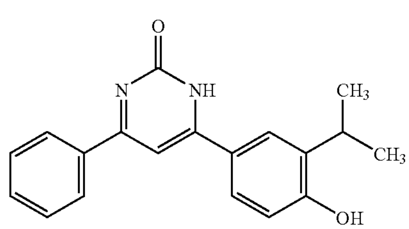 | 6-[4-hydroxy-3-(1-methylethyl)phenyl]-4-phenylpyrimidin-2(1H)-one | 307 |

TABLE 1-continued

| Cpd. No. | Structure | IUPAC Name | MS |
|---|---|---|---|
| 27 | 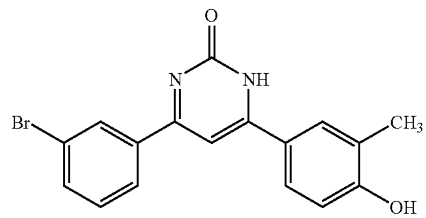 | 4-(3-bromophenyl)-6-(4-hydroxy-3-methylphenyl)pyrimidin-2(1H)-one | 358 |
| 28 | 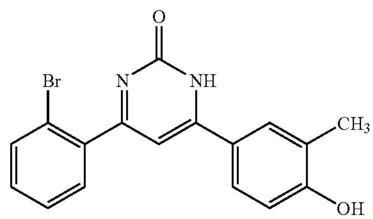 | 4-(2-bromophenyl)-6-(4-hydroxy-3-methylphenyl)pyrimidin-2(1H)-one | 358 |
| 29 | 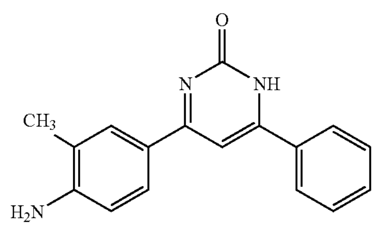 | 4-(4-amino-3-methylphenyl)-6-phenylpyrimidin-2(1H)-one | 278 |
| 30 | 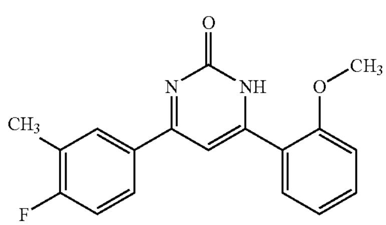 | 4-(4-fluoro-3-methylphenyl)-6-[2-(methyloxy)phenyl]pyrimidin-2(1H)-one | 311 |
| 31 | 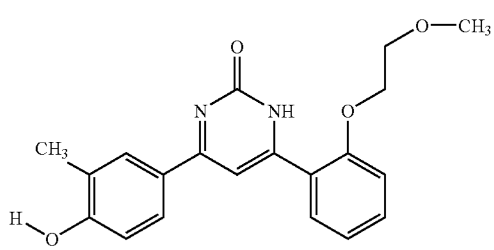 | 4-(4-hydroxy-3-methylphenyl)-6-(2-{[2-(methyloxy)ethyl]oxy}phenyl)pyrimidin-2(1H)-one | 353 |
| 32 | 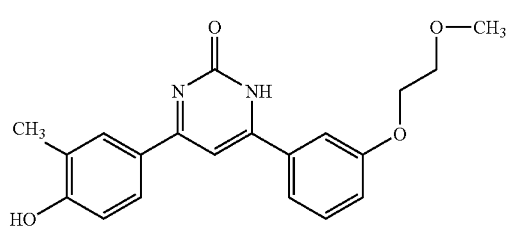 | 4-(4-hydroxy-3-methylphenyl)-6-(3-{[2-(methyloxy)ethyl]oxy}phenyl)pyrimidin-2(1H)-one | 353 |
| 33 | 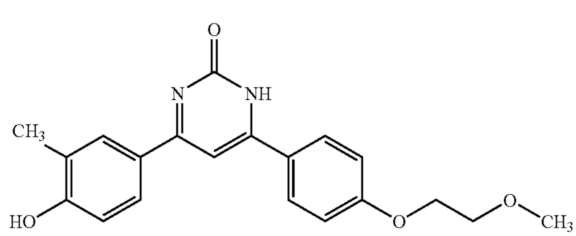 | 4-(4-hydroxy-3-methylphenyl)-6-(4-{[2-(methyloxy)ethyl]oxy}phenyl)pyrimidin-2(1H)-one | 353 |

TABLE 1-continued

| Cpd. No. | Structure | IUPAC Name | MS |
|---|---|---|---|
| 34 | 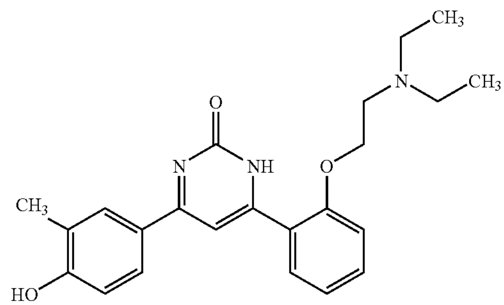 | 6-(2-{[2-(diethylamino)ethyl]oxy}phenyl)-4-(4-hydroxy-3-methylphenyl)pyrimidin-2(1H)-one | 394 |
| 35 | 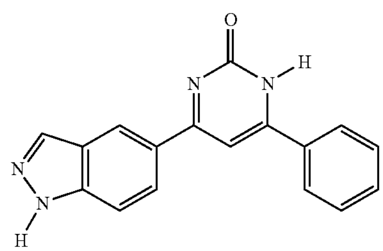 | 4-(1H-indazol-5-yl)-6-phenylpyrimidin-2(1H)-one | 289 |
| 36 | 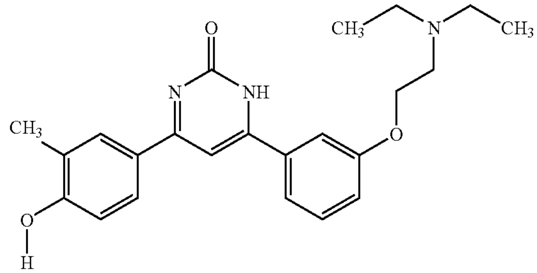 | 6-(3-{[2-(diethylamino)ethyl]oxy}phenyl)-4-(4-hydroxy-3-methylphenyl)pyrimidin-2(1H)-one | 394 |
| 37 | 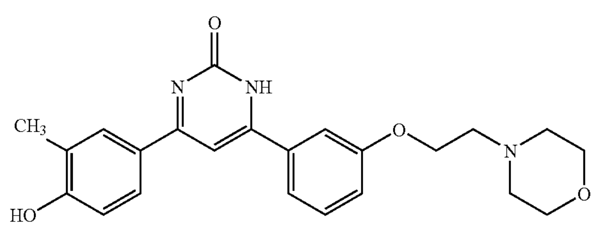 | 4-(4-hydroxy-3-methylphenyl)-6-{3-[(2-morpholin-4-ylethyl)oxy]phenyl}pyrimidin-2(1H)-one | 408 |
| 38 | 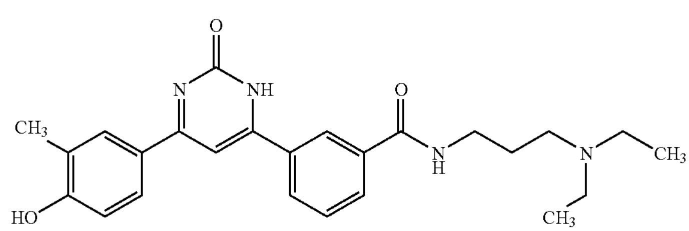 | N-[3-(diethylamino)propyl]-3-[6-(4-hydroxy-3-methylphenyl)-2-oxo-2,3-dihydropyrimidin-4-yl]benzamide | 435 |
| 39 | 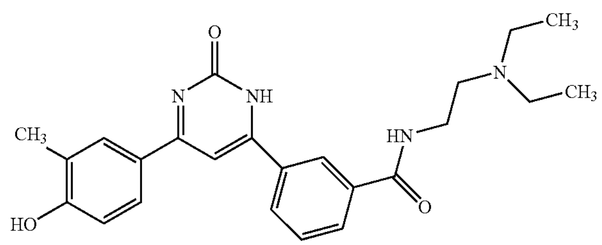 | N-[2-(diethylamino)ethyl]-3-[6-(4-hydroxy-3-methylphenyl)-2-oxo-2,3-dihydropyrimidin-4-yl]benzamide | 421 |

TABLE 1-continued

| Cpd. No. | Structure | IUPAC Name | MS |
|---|---|---|---|
| 40 | 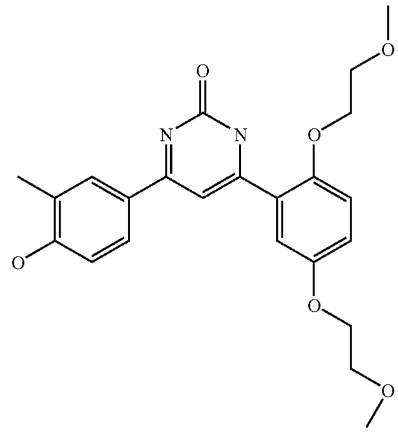 | 6-(2,5-bis{[2-(methyloxy)ethyl]oxy}phenyl)-4-(4-hydroxy-3-methylphenyl)pyrimidin-2(1H)-one | 427 |
| 41 | 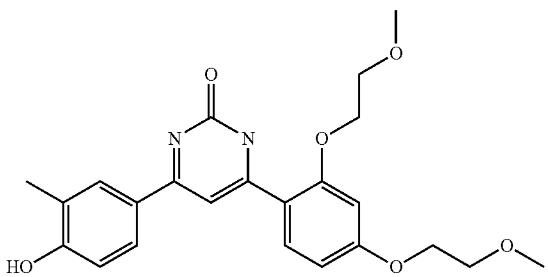 | 6-(2,4-bis{[2-(methyloxy)ethyl]oxy}phenyl)-4-(4-hydroxy-3-methylphenyl)pyrimidin-2(1H)-on | 427 |
| 42 | 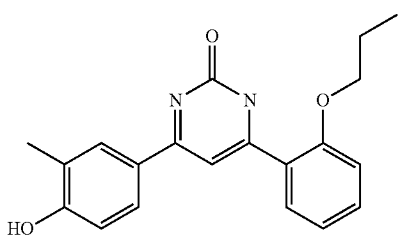 | 4-(4-hydroxy-3-methylphenyl)-6-[2-(propyloxy)phenyl]pyrimidin-2(1H)-one | 337 |
| 43 | 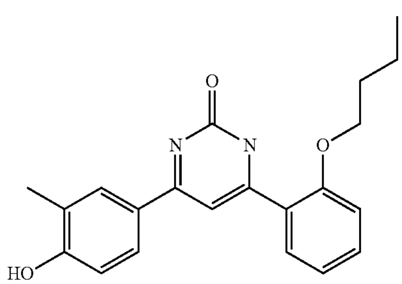 | 6-[2-(butyloxy)phenyl]-4-(4-hydroxy-3-methylphenyl)pyrimidin-2(1H)-one | 351 |
| 44 | 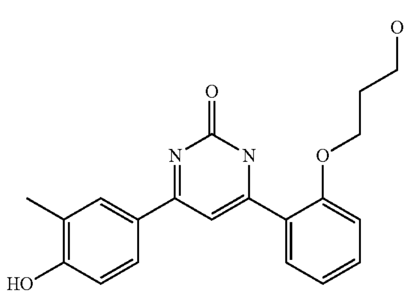 | 4-(4-hydroxy-3-methylphenyl)-6-{2-[(3-hydroxypropyl)oxy]phenyl}pyrimidin-2(1H)-one | 431 |

TABLE 1-continued

| Cpd. No. | Structure | IUPAC Name | MS |
|---|---|---|---|
| 45 | 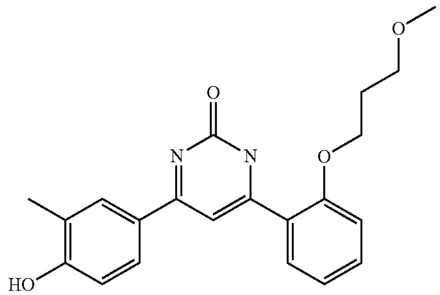 | 4-(4-hydroxy-3-methylphenyl)-6-(2-{[3-(methyloxy)propyl]oxy}phenyl)pyrimidin-2(1H)-one | 367 |
| 46 | 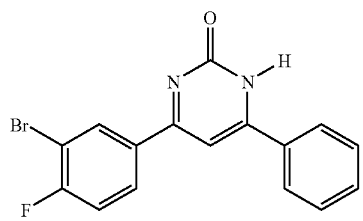 | 4-(3-bromo-4-fluorophenyl)-6-phenylpyrimidin-2(1H)-one | 345 |
| 47 | 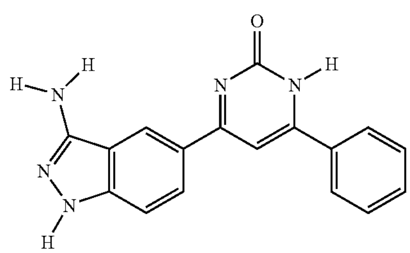 | 4-(3-amino-1H-indazol-5-yl)-6-phenylpyrimidin-2(1H)-one | 304 |
| 48 | 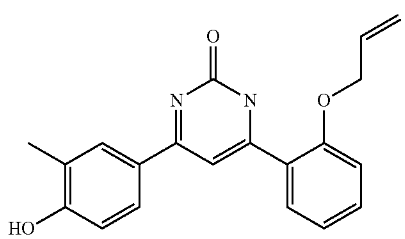 | 4-(4-hydroxy-3-methylphenyl)-6-[2-(prop-2-en-1-yloxy)phenyl]pyrimidin-2(1H)-one | 347 |
| 49 | 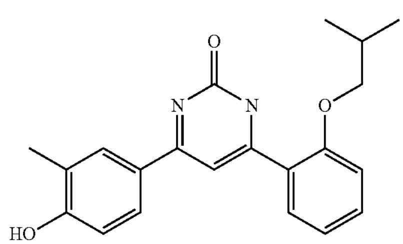 | 4-(4-hydroxy-3-methylphenyl)-6-{2-[(2-methylpropyl)oxy]phenyl}pyrimidin-2(1H)-one | 351 |
| 50 | 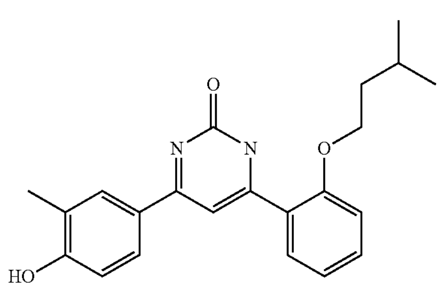 | 4-(4-hydroxy-3-methylphenyl)-6-{2-[(3-methylbutyl)oxy]phenyl}pyrimidin-2(1H)-one | 365 |

TABLE 1-continued

| Cpd. No. | Structure | IUPAC Name | MS |
|---|---|---|---|
| 51 | 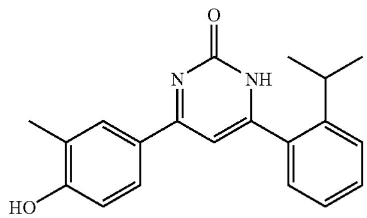 | 4-(4-hydroxy-3-methylphenyl)-6-[2-(1-methylethyl)phenyl]pyrimidin-2(1H)-one | |
| 52 | 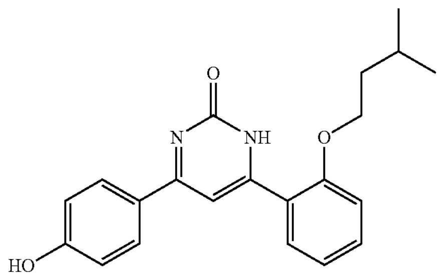 | 4-(4-hydroxyphenyl)-6-{2-[(3-methylbutyl)oxy]phenyl}pyrimidin-2(1H)-one | 351 |
| 53 | 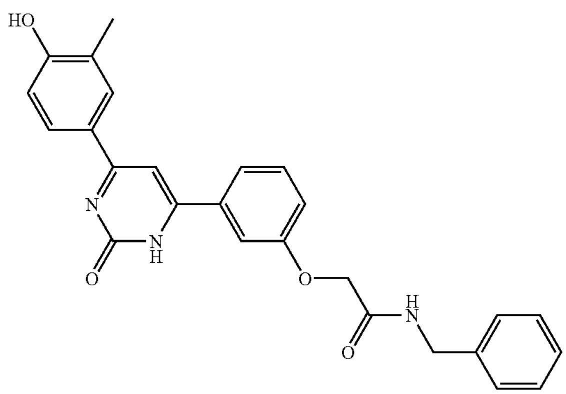 | 2-({3-[6-(4-hydroxy-3-methylphenyl)-2-oxo-2,3-dihydropyrimidin-4-yl]phenyl}oxy)-N-(phenylmethyl)acetamide | 442 |
| 54 | 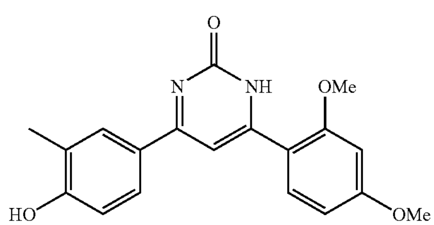 | 6-[2,4-bis(methyloxy)phenyl]-4-(4-hydroxy-3-methylphenyl)pyrimidin-2(1H)-one | 339 |
| 55 | 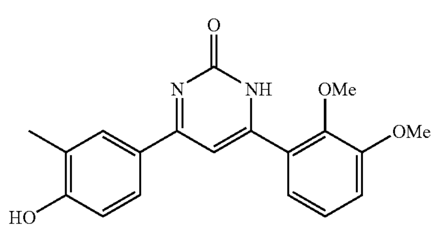 | 6-[2,3-bis(methyloxy)phenyl]-4-(4-hydroxy-3-methylphenyl)pyrimidin-2(1H)-one | 339.4 |
| 56 | 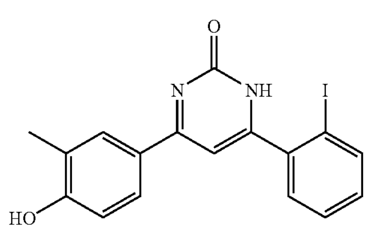 | 4-(4-hydroxy-3-methylphenyl)-6-(2-iodophenyl)pyrimidin-2(1H)-one | 405 |

TABLE 1-continued

| Cpd. No. | Structure | IUPAC Name | MS |
|---|---|---|---|
| 57 | 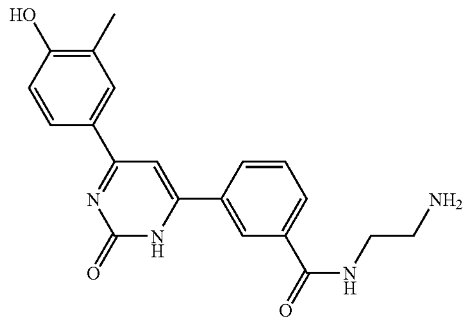 | N-(2-aminoethyl)-3-[6-(4-hydroxy-3-methylphenyl)-2-oxo-2,3-dihydropyrimidin-4-yl]benzamide | 365 |
| 58 | 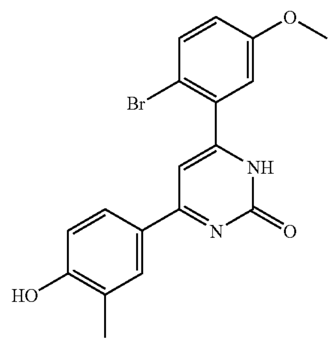 | 6-[2-bromo-5-(methyloxy)phenyl]-4-(4-hydroxy-3-methylphenyl)pyrimidin-2(1H)-one | |
| 59 | 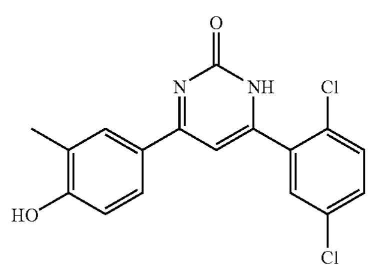 | 6-(2,5-dichlorophenyl)-4-(4-hydroxy-3-methylphenyl)pyrimidin-2(1H)-one | 307 |
| 60 | 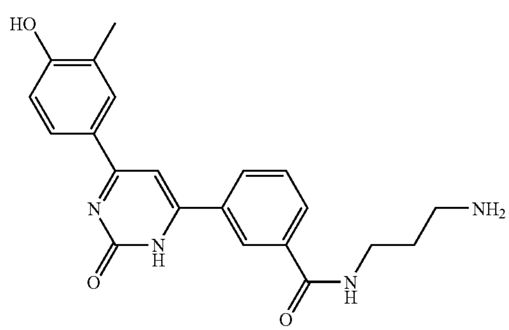 | N-(3-aminopropyl)-3-[6-(4-hydroxy-3-methylphenyl-2-oxo-2,3-dihydropyrimidin-4-yl]benzamide | 379 |
| 61 | 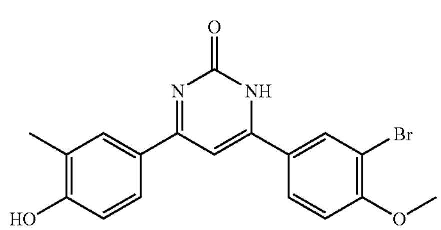 | 6-[3-bromo-4-(methyloxy)phenyl]-4-(4-hydroxy-3-methylphenyl)pyrimidin-2(1H)-one | 387 |

TABLE 1-continued

| Cpd. No. | Structure | IUPAC Name | MS |
|---|---|---|---|
| 62 | 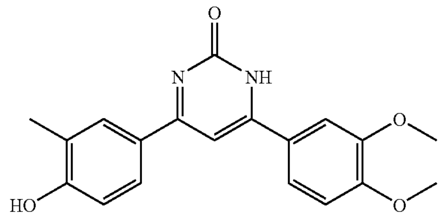 | 6-[3,4-bis(methyloxy)phenyl]-4-(4-hydroxy-3-methylphenyl)pyrimidin-2(1H)-one | 339.1 |
| 63 | 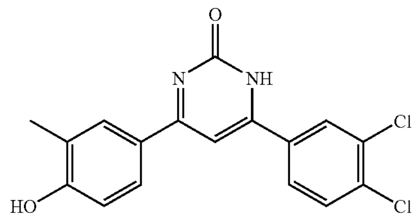 | 6-(3,4-dichlorophenyl)-4-(4-hydroxy-3-methylphenyl)pyrimidin-2(1H)-one | 347 |
| 64 | 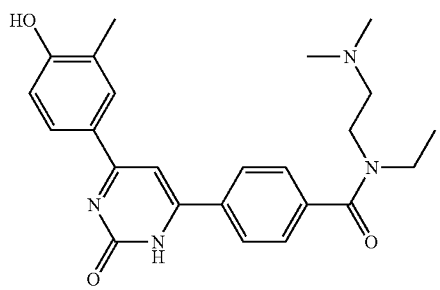 | N-[2-(dimethylamino)ethyl]-N-ethyl-4-[6-(4-hydroxy-3-methylphenyl)-2-oxo-2,3-dihydropyrimidin-4-yl]benzamide | 323 |
| 65 | 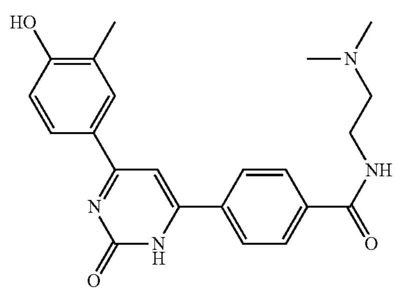 | N-[2-(dimethylamino)ethyl]-4-[6-(4-hydroxy-3-methylphenyl)-2-oxo-2,3-dihydropyrimidin-4-yl]benzamide | 393 |
| 66 | 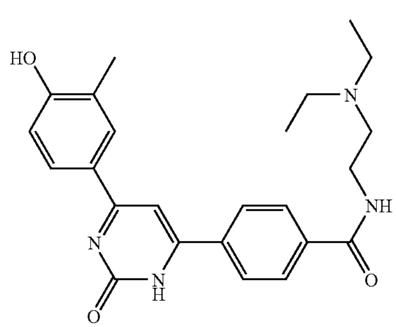 | N-[2-(diethylamino)ethyl]-4-[6-(4-hydroxy-3-methylphenyl)-2-oxo-2,3-dihydropyrimidin-4-yl]benzamlde | 421 |

TABLE 1-continued

| Cpd. No. | Structure | IUPAC Name | MS |
|---|---|---|---|
| 67 | 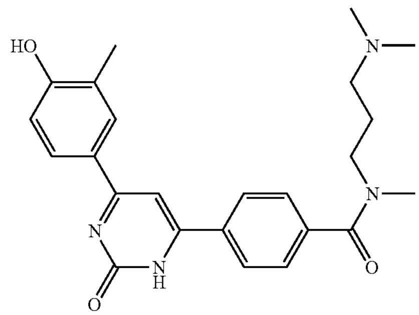 | N-[3-(dimethylamino)propyl]-4-[6-(4-hydroxy-3-methylphenyl)-2-oxo-2,3-dihydropyrimidin-4-yl]-N-methylbenzamide | 421 |
| 68 | 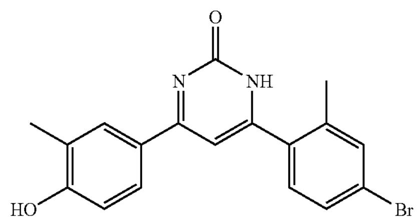 | 6-(4-bromo-2-methylphenyl)-4-(4-hydroxy-3-methylphenyl)pyrimidin-2(1H)-one | 371.4 |
| 69 | 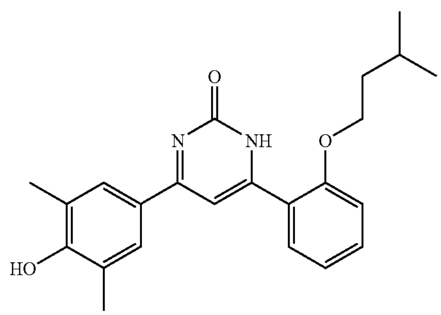 | 4-(4-hydroxy-3,5-dimethylphenyl)-6-{2-[(3-methylbutyl)oxy]phenyl}pyrimidin-2(1H)-one | 379 |
| 70 | 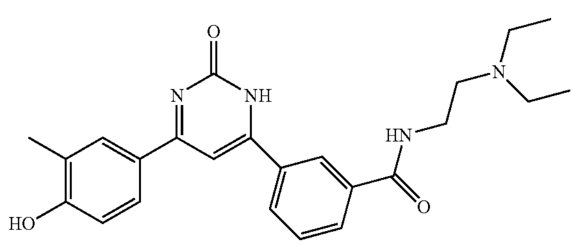 | N-[2-(diethylamino)ethyl]-3-[6-(4-hydroxy-3-methylphenyl)-2-oxo-2,3-dihydropyrimidin-4-yl]benzamide | |
| 71 | 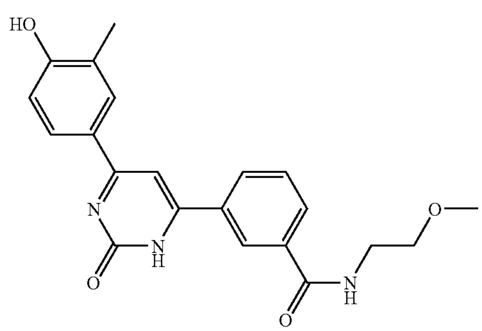 | 3-[6-(4-hydroxy-3-methylphenyl)-2-oxo-2,3-dihydropyrimidin-4-yl]-N-[2-(methyloxy)ethyl]benzamide | 380 |

TABLE 1-continued

| Cpd. No. | Structure | IUPAC Name | MS |
|---|---|---|---|
| 72 | 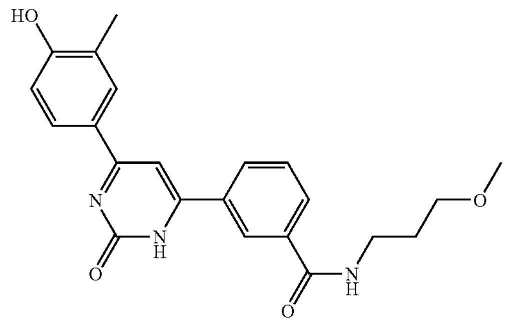 | 3-[6-(4-hydroxy-3-methylphenyl)-2-oxo-2,3-dihydropyrimidin-4-yl]-N-[3-(methyloxy)propyl]benzamide | 394 |
| 73 | 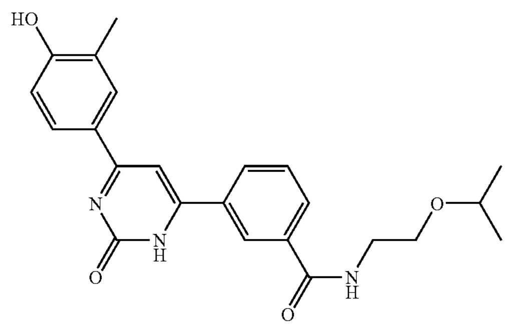 | 3-[6-(4-hydroxy-3-methylphenyl)-2-oxo-2,3-dihydropyrimidin-4-yl]-N-{2-[(1-methylethyl)oxy]ethyl}benzamide | 408 |
| 74 | 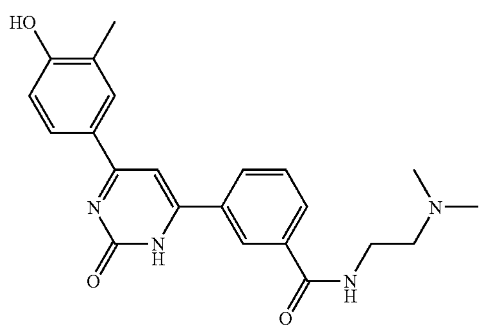 | N-[2-(dimethylamino)ethyl]-3-[6-(4-hydroxy-3-methylphenyl)-2-oxo-2,3-dihydropyrimidin-4-yl]benzamide | 393 |
| 75 | 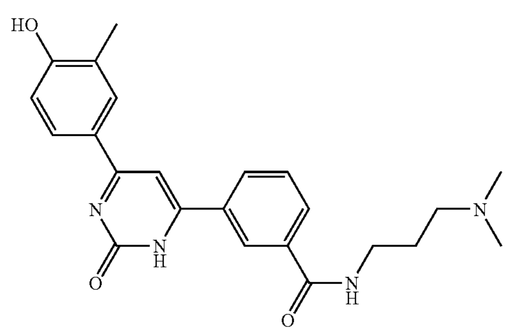 | N-[3-(dimethylamino)propyl]-3-[6-(4-hydroxy-3-methylphenyl)-2-oxo-2,3-dihydropyrimidin-4-yl]benzamide | 407 |

TABLE 1-continued

| Cpd. No. | Structure | IUPAC Name | MS |
|---|---|---|---|
| 76 | 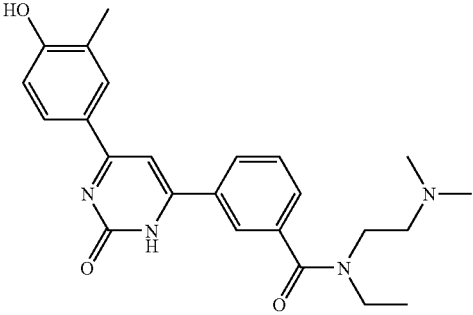 | N-[2-(dimethylamino)ethyl]-N-ethyl-3-[6-(4-hydroxy-3-methylphenyl)-2-oxo-2,3-dihydropyrimidin-4-yl]benzamide | 421 |
| 77 | 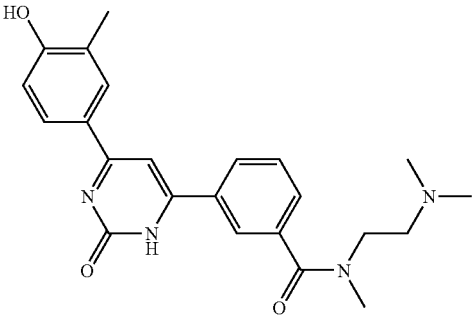 | N-[2-(dimethylamino)ethyl]-3-[6-(4-hydroxy-3-methylphenyl)-2-oxo-2,3-dihydropyrimidin-4-yl]-N-methylbenzamide | 407 |
| 78 | 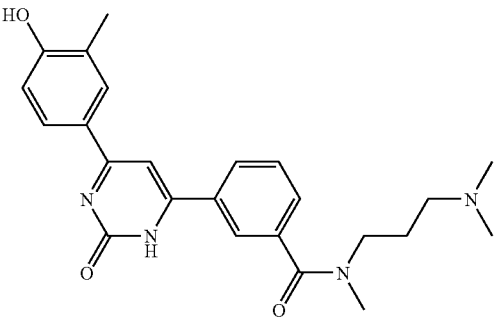 | N-[3-(dimethylamino)propyl]-3-[6-(4-hydroxy-3-methylphenyl)-2-oxo-2,3-dihydropyrimidin-4-yl]-N-methylbenzamide | 421 |
| 79 | 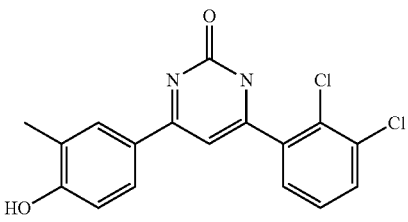 | 6-(2,3-dichlorophenyl)-4-(4-hydroxy-3-methylphenyl)pyrimidin-2(1H)-one | 348.5 |

The compounds in the table above can be prepared using art recognized methods.

Abbreviations and Definitions

The following abbreviations and terms have the indicated meanings throughout:

| Abbreviation | Meaning |
|---|---|
| Ac | Acetyl |
| °C. | degrees Celsius |
| CBZ | CarboBenZoxy = benzyloxycarbonyl |
| D | Doublet |
| DIPEA | N,N-diisopropylethylamine |
| DMF | N,N-dimethylformamide |
| DMSO | dimethyl sulfoxide |
| EI | Electron Impact ionization |
| Et | Ethyl |
| G | gram(s) |
| GC | gas chromatography |
| h or hr | hour(s) |
| HOAc | acetic acid |
| HOBt | hydroxybenzotriazole |
| HPLC | high pressure liquid chromatography |

| Abbreviation | Meaning |
|---|---|
| l or L | liter(s) |
| M | molar or molarity |
| M | Multiplet |
| Me | Methyl |
| Mesyl | Methanesulfonyl |
| Mg or mg | milligram(s) |
| MHz | megahertz (frequency) |
| Min | minute(s) |
| mL | milliliter(s) |
| mM | Millimolar |
| Mmol | millimole(s) |
| Mol or mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | Nanomolar |
| NMO | N-methylmorpholine oxide |
| NMR | nuclear magnetic resonance spectroscopy |
| Ph | Phenyl |
| PhOH | Phenol |
| PPTS | Pyridinium p-toluenesulfonate |
| Q | Quartet |
| RT or rt | Room temperature |
| Sat'd | Saturated |
| S | Singlet |
| t | Triplet |
| TFA | trifluoroacetic acid |
| THF | Tetrahydrofuran |
| TMOF | trimethyl orthoformate |
| TMS | Trimethylsilyl |
| Tosyl | p-toluenesulfonyl |
| uL | microliter(s) |
| uM | Micromole(s) or micromolar |
| LS/MSD | A type of Liquid Chromatography Mass Spectrometer |
| PPh$_3$ | Triphenylphosphine |

DEFINITIONS

As used in the present specification, the following words and phrases are generally intended to have the meanings as set forth below, except to the extent that the context in which they are used indicates otherwise or they are expressly defined to mean something different.

The symbol "—" means a single bond, "═" means a double bond, "≡" means a triple bond, "⸺" means a single or double bond. When a group is depicted removed from its parent formula, the "⤳" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

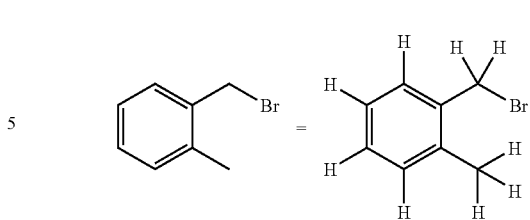

If a group "R" is depicted as "floating" on a ring system, as for example in the formula:

then, unless otherwise defined, a substituent "R" can reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

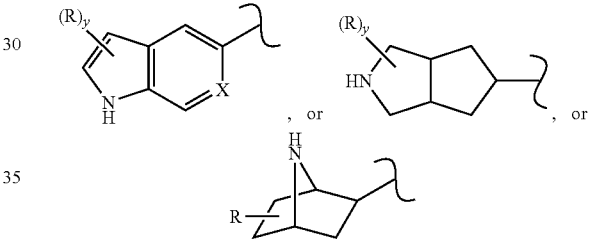

then, unless otherwise defined, a substituent "R" can reside on any atom of the fused ring system, assuming replacement of a depicted hydrogen (for example the —NH— in the formula above), implied hydrogen (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group can reside on either the 5-membered or the 6-membered ring of the fused ring system. In the formula depicted above, when y is 2 for example, then the two "R's" can reside on any two atoms of the ring system, again assuming each replaces a depicted, implied, or expressly defined hydrogen on the ring.

When a group "R" is depicted as existing on a ring system containing saturated carbons, as for example in the formula:

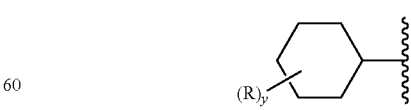

where, in this example, "y" can be more than one, assuming each replaces a currently depicted, implied, or expressly defined hydrogen on the ring; then, unless otherwise defined, where the resulting structure is stable, two "R's" can reside on the same carbon. A simple example is when R is a methyl group; there can exist a geminal dimethyl on a carbon of the depicted ring (an "annular" carbon). In another example, two R's on the same carbon, including that carbon, can form a ring, thus creating a spirocyclic ring (a "spirocyclyl" group) structure with the depicted ring as for example in the formula:

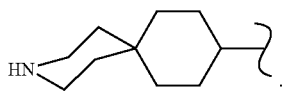

"$(C_1\text{-}C_6)$alkyl" is intended to mean $C_1\text{-}C_6$ linear or branched structures and combinations thereof, inclusively. For example, "$C_6$ alkyl" can refer to an n-hexyl, iso-hexyl, and the like. "$(C_1\text{-}C_6)$alkyl is intended to include" $(C_1\text{-}C_3)$ alkyl. Examples of $(C_1\text{-}C_6)$alkyl groups include methyl, ethyl, propyl, isopropyl, butyl, s-butyl, t-butyl, isobutyl, pentyl, hexyl and the like. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl.

"$(C_3\text{-}C_{10})$cycloalkyl" means a non-aromatic mono- or multicyclic ring system comprising about 3 to 10 carbon atoms. $(C_3\text{-}C_{10})$cycloalkyl is intended to include $(C_5\text{-}C_6)$cycloalkyl. Non-limiting examples of monocyclic cycloalkyls include cyclopropyl, cyclopentyl, cyclohexyl, cycloheptyl and the like. Non-limiting examples of multicyclic cycloalkyls include 1-decalin, norbornyl, adamantyl and the like. Cycloalkyls can be fused or bridge ring systems or spirocyclic systems.

"Alkylene" is a subset of alkyl and refers to straight or branched chain divalent group consisting solely of carbon and hydrogen atoms, containing no unsaturation and having from one to six carbon atoms, for example, methylene, ethylene, propylene, n-butylene and the like. Alkylene refers to the same residues as alkyl, but having two points of attachment and, specifically, fully saturated. Examples of alkylene include ethylene (—$CH_2CH_2$—), propylene (—$CH_2CH_2CH_2$—), and dimethylpropylene (—$CH_2C(CH_3)_2CH_2$—).

"Alkylidene" is a subset of alkyl and refers to a straight or branched chain unsaturated divalent group consisting solely of carbon and hydrogen atoms, having from two to six carbon atoms, for example, ethylidene, propylidene, n-butylidene, and the like. Alkylidene refers to the same residues as alkyl, but having two points of attachment and, specifically, double bond unsaturation. The unsaturation present includes at least one double bond.

"Alkylidyne" refers to a straight or branched chain unsaturated divalent group consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above groups, "alkylene," "alkylidene" and "alkylidyne," when optionally substituted, can contain alkyl substitution which itself contains unsaturation. For example, 2-(2-phenylethynyl-but-3-enyl)-naphthalene (IUPAC name) contains an n-butylid-3-ynyl group with a vinyl substituent at the 2-position of said group.

"$(C_1\text{-}C_6)$alkoxy" refers to the group O—$(C_1\text{-}C_6)$alkyl, wherein the term "$(C_1\text{-}C_6)$alkyl" is as defined hereinabove. "$(C_1\text{-}C_6)$alkoxy" is intended to include $(C_1\text{-}C_3)$alkoxy. Examples include methoxy, ethoxy, propoxy, isopropoxy, and the like.

"$(C_5\text{-}C_{10})$aryl" means a monovalent five- to ten-membered mono- or multicyclic ring, wherein the monocyclic ring is aromatic and at least one of the rings in the multicyclic ring is aromatic. "$(C_5\text{-}C_{10})$aryl" is intended to include "$(C_5\text{-}C_6)$aryl. Representative non-limiting examples of aryl include phenyl, naphthyl, and indanyl, and the like.

"Arylalkyl" means a residue in which an aryl moiety, as defined above, is attached to a parent structure via one of an alkylene, alkylidene, or alkylidyne group. Examples include benzyl, phenethyl, phenylvinyl, phenylallyl and the like.

"—$(C_1\text{-}C_6)$alkyl-$(C_5\text{-}C_{10})$aryl," is intended to mean a $(C_5\text{-}C_{10})$aryl moiety attached to a parent structure via $(C_1\text{-}C_6)$ alkylene group. Examples include benzyl, phenethyl, and the like.

In some examples, as appreciated by one of ordinary skill in the art, two adjacent groups on an aromatic system can be fused together to form a ring structure. The fused ring structure can contain heteroatoms and can be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems includes non-aromatic and aromatic systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention can themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl groups that are substituted with one or more halogens, respectively. Non-limiting examples of "haloalkyl" include —$CH_2F$, —$CHCl_2$ or —$CF_3$.

"Heteroatom" refers to O, S, N, or P.

"(4-10 membered)heterocycloalkyl" refers to a stable four- to ten-membered ring substituent that consists of carbon atoms and from one to five heteroatoms selected from the nitrogen, phosphorus, oxygen and sulfur. For purposes of this invention, the heterocycloalkyl substituent can be a monocyclic or a multicyclic ring system, which can include fused or bridged ring systems as well as spirocyclic systems.

"(5-10 membered)heteroaryl" refers to a stable five- to ten-membered ring substituent that consists of carbon atoms and from one to five heteroatoms selected from the nitrogen, phosphorus, oxygen and sulfur. For purposes of this invention, the heteroaryl substituent can be a monocyclic or a multicyclic ring system, which can include fused or bridged ring systems as well as spirocyclic systems.

In the above heteroaryl and heterocycloalkyl substituents, the nitrogen, phosphorus, carbon or sulfur atoms can be optionally oxidized to various oxidation states. In a specific example, the group —$S(O)_{0\text{-}2}$—, refers to —S-(sulfide), —S(O)— (sulfoxide), and —$SO_2$— (sulfone) respectively. For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms can be optionally quaternized; and the ring substituent can be partially or fully saturated or aromatic.

Non-limiting examples of (4-10 membered)heterocycloalkyl and (5-10 membered)heteroaryl groups include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, tetrahydrofuranyl, tetrahydroisoquinolinyl, and tetrahydroquinolinyl.

Representative examples of "(5-10 membered)heteroaryl" include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzdioxolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Fused, bridged, and spiro moieties are also included within the scope of this definition.

When a group is referred to as "—(C₁-C₆)alkyl-(4-10 membered)heterocycloalkyl" the heterocycloalkyl is attached to a parent structure via one of an alkylene, alkylidene, or alkylidyne group. Examples include (4-methylpiperazin-1-yl)methyl, (morpholin-4-yl)methyl, (pyridine-4-yl) methyl, 2-(oxazolin-2-yl)ethyl, 4-(4-methylpiperazin-1-yl)-2-butenyl, and the like. Both the heterocyclyl and the corresponding alkylene, alkylidene, or alkylidyne portion of a heterocyclylalkyl group can be optionally substituted.

"Optional" or "optionally" means that the subsequently described event or circumstance can or can not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC₁₋₈ alkyl," both the "C₁₋₈ alkyl" portion and the "aryl" portion of the molecule can or can not be substituted. A list of exemplary optional substitutions is presented below in the definition of "substituted."

"Saturated bridged ring system" refers to a bicyclic or polycyclic ring system that is not aromatic. Such a system can contain isolated or conjugated unsaturation, but not aromatic or heteroaromatic rings in its core structure (but can have aromatic substitution thereon). For example, hexahydro-furo [3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

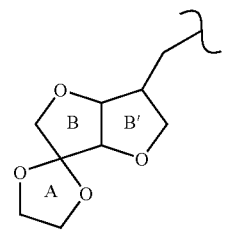

"Substituted" alkyl, aryl, and heterocyclyl, refer respectively to alkyl, aryl, and heterocyclyl, one or more (for example up to about five, in another example, up to about three) hydrogen atoms are replaced by a substituent independently selected from: alkyl (for example, fluoromethyl), aryl (for example, 4-hydroxyphenyl), arylalkyl (for example, 1-phenyl-ethyl), heterocyclylalkyl (for example, 1-pyridin-3-yl-ethyl), heterocyclyl (for example, 5-chloro-pyridin-3-yl or 1-methyl-piperidin-4-yl), alkoxy, alkylenedioxy (for example methylenedioxy), amino (for example, alkylamino and dialkylamino), amidino, aryloxy (for example, phenoxy), arylalkyloxy (for example, benzyloxy), carboxy (—CO₂H), carboalkoxy (that is, acyloxy or —OC(=O)R), carboxyalkyl (that is, esters or —CO₂R), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido. And each substituent of a substituted group is optionally substituted, but these optional substituents themselves are not further substituted. Thus, an optionally substituted moiety is one that can or can not have one or more substituents, and each of the substituents can or can not have one or more substituents. But, the substituents of the substituents can not be substituted.

Some of the compounds of the invention can have imino, amino, oxo or hydroxy substituents off aromatic heterocyclyl systems. For purposes of this disclosure, it is understood that such imino, amino, oxo or hydroxy substituents can exist in their corresponding tautomeric form, i.e., amino, imino, hydroxy or oxo, respectively.

The compounds of the invention, or their pharmaceutically acceptable salts, can have asymmetric carbon atoms, oxidized sulfur atoms or quaternized nitrogen atoms in their structure.

The compounds of the invention and their pharmaceutically acceptable salts can exist as single stereoisomers, racemates, and as mixtures of enantiomers and diastereomers. The compounds can also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that theoretically some constructs which would not normally be considered as stable compounds (that is, sterically practical and/or synthetically feasible, supra).

When a particular group with its bonding structure is denoted as being bonded to two partners; that is, a divalent group, for example, —OCH$_2$—, then it is understood that either of the two partners can be bound to the particular group at one end, and the other partner is necessarily bound to the other end of the particular group, unless stated explicitly otherwise. Stated another way, divalent groups are not to be construed as limited to the depicted orientation, for example "—OCH$_2$—" is meant to mean not only "—OCH$_2$—" as drawn, but also "—CH$_2$O—."

In addition to the various embodiments recited hereinabove, also encompassed by this invention are combinations of the embodiments described herein.

Methods for the preparation and/or separation and isolation of single stereoisomers from racemic mixtures or non-racemic mixtures of stereoisomers are well known in the art. For example, optically active (R)- and (S)-isomers can be prepared using chiral synthons or chiral reagents, or resolved using conventional techniques. Enantiomers (R- and S-isomers) can be resolved by methods known to one of ordinary skill in the art, for example by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step can be required to liberate the desired enantiomeric form. Alternatively, specific enantiomer can be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer can be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, can also modulate, either directly or indirectly, phosphatase activity. This additional modulation, if present, can be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarnorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoina, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defomians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphpblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropyl amine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons).

Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt can be the biologically active form of the compound in the body. In one example, a prodrug can be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art, in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

It is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition can be necessary, and will be ascertainable with routine experimentation by one of ordinary skill in the art.

One of ordinary skill in the art would understand that certain crystallized, protein-ligand complexes, in particular CK2-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods can be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for kinase modulation, and determining whether said candidate agent modulates kinase activity in the assay. Such methods can also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method can be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

In the another aspect, the invention provides pharmaceutical compositions comprising an inhibitor of CK2 according to the invention and a pharmaceutically acceptable carrier, excipient, or diluent. In other embodiments, administration can preferably be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions can include a conventional pharmaceutical carrier or excipient and a compound of the invention as the/an active agent, and, in addition, can include other medicinal agents, pharmaceutical agents, carriers, adjuvants, etc. Compositions of the invention can be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It can also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention can also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid dosage forms as described above can be prepared with coatings and shells, such as enteric coatings and others well known in the art. They can contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, can contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with, for example, suitable-non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as can be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Utility of Compounds of the Invention as Screening Agents

To employ the compounds of the invention in a method of screening for candidate agents that bind to, for example CK2, the protein is bound to a support, and a compound of the invention is added to the assay. Alternatively, the compound of the invention is bound to the support and the protein is added. Classes of candidate agents among which novel binding agents can be sought include specific antibodies, non-natural binding agents identified in screens of chemical libraries, peptide analogs, etc. Of particular interest are screening assays for candidate agents that have a low toxicity for human cells. A wide variety of assays can be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, CK2 can be done in a number of ways. In one example, the candidate agent (the compound of the invention) is labeled, for example, with a fluorescent or radioactive moiety and binding determined directly. For example, this can be done by attaching all or a portion of the CK2 protein to a solid support, adding a labeled agent (for example a compound of the invention in which at least one atom has been replaced by a detectable isotope), washing off excess reagent, and determining whether the amount of the label is that present on the solid support. Various blocking and washing steps can be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

In some embodiments, only one of the components is labeled. For example, CK2 protein can be labeled at tyrosine positions using $^{125}$I, or with fluorophores. Alternatively, more than one component can be labeled with different labels; using $^{125}$I for the proteins, for example, and a fluorophor for the candidate agents.

The compounds of the invention can also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They can be capable of directly or indirectly altering the cellular proliferation phenotype or the expression of a cellular proliferation sequence, including both nucleic acid sequences, and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to CK2.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclyl structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to IGF1R, such as an antibody, peptide, binding partner, ligand, etc. Under certain circumstances, there can be competitive binding as between the candidate agent and the binding moiety, with the binding moiety displacing the candidate agent.

In some embodiments, the candidate agent is labeled. Either the candidate agent, or the competitor, or both, is added first to CK2 protein for a time sufficient to allow binding, if present. Incubations can be performed at any temperature that facilitates optimal activity, typically between 4° C. and 40° C.

Incubation periods are selected for optimum activity, but can also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to CK2 and thus is capable of binding to, and potentially modulating, the activity of the CK2. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor can indicate the candidate agent is bound to CK2 with a higher affinity. Thus, if the candidate agent is labeled, the presence of the label on the support, coupled with a lack of competitor binding, can indicate the candidate agent is capable of binding to CK2.

It can be of value to identify the binding site of CK2. This can be done in a variety of ways. In one embodiment, once CK2 is identified as binding to the candidate agent, the CK2 is fragmented or modified and the assays repeated to identify the necessary components for binding.

Modulation is tested by screening for candidate agents capable of modulating the activity of CK2 comprising the steps of combining a candidate agent with CK2, as above, and determining an alteration in the biological activity of the CK2. Thus, in this embodiment, the candidate agent should both bind to (although this can not be necessary), and alter its biological or biochemical activity as defined herein. The methods include both in vitro screening methods and in vivo screening of cells for alterations in cell viability, morphology, and the like.

Alternatively, differential screening can be used to identify drug candidates that bind to native CK2, but cannot bind to modified CK2.

Positive controls and negative controls can be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins, e.g., albumin, detergents, etc which can be used to facilitate optimal protein-protein binding and/or reduce non-specific or background interactions. Also reagents that otherwise improve the efficiency of the assay, such as protease inhibitors, nuclease inhibitors, anti-microbial agents, etc., can be used. The mixture of components can be added in any order that provides for the requisite binding.

One of ordinary skill in the art would understand that certain crystallized, protein-ligand complexes, in particular CK2-ligand complexes, and their corresponding x-ray structure coordinates can be used to reveal new structural information useful for understanding the biological activity of CK2 kinases as described herein. As well, the key structural features of the aforementioned proteins, particularly, the shape of the ligand binding site, are useful in methods for designing or identifying selective modulators of CK2 kinases and in solving the structures of other proteins with similar features. Ligands of such complexes can include compounds of the invention as described herein.

As well, one of ordinary skill in the art would appreciate that such suitable x-ray quality crystals can be used as part of a method of identifying a candidate agent capable of binding to and modulating the activity of CK2 kinases. Such methods can be characterized by the following aspects: a) introducing into a suitable computer program, information defining a ligand binding domain of a CK2 kinase in a conformation (e.g. as defined by x-ray structure coordinates obtained from suitable x-ray quality crystals as described above) the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods can further entail: performing rational drug design with the model of the three-dimensional structure, and selecting a potential candidate agent in conjunction with computer modeling.

Additionally, one skilled in the art would appreciate that such methods can further entail: employing a candidate agent, so-determined to fit spatially into the ligand binding domain, in a biological activity assay for CK2 kinase modulation, and determining whether said candidate agent modulates CK2 kinase activity in the assay. Such methods can also include administering the candidate agent, determined to modulate CK2 kinase activity, to a mammal suffering from a condition treatable by CK2 kinase modulation, such as those described above.

Also, one skilled in the art would appreciate that compounds of the invention can be used in a method of evaluating the ability of a test agent to associate with a molecule or molecular complex comprising a ligand binding domain of a CK2 kinase. Such a method can be characterized by the following aspects: a) creating a computer model of a CK2 kinase binding pocket using structure coordinates obtained from suitable x-ray quality crystals of the CK2 kinase, b) employing computational algorithms to perform a fitting operation between the test agent and the computer model of the binding pocket, and c) analyzing the results of the fitting operation to quantify the association between the test agent and the computer model of the binding pocket.

Synthetic Procedures

Generally, the compounds listed below were identified by LC-MS, and/or isolated, and characterized by $^1$H-NMR (most typically 400 MHz). Liquid chromatography-mass spectral (LC-MS) analyses were performed using at least one of: a Hewlett-Packard Series 1100 MSD, an Agilent 1100 Series LC/MSD (available from Agilent Technologies Deutschland GmbH of Waldbronn Germany), or a Waters 8-Channel MUX System (available from Waters Corporation of Milford, Mass.). Compounds were identified according to either their observed mass [M+1] or [M+Na] ion (positive mode) or [M−1] ion (negative mode). $^1$H-NMR data for compounds was taken with a Varian AS400 Spectrometer (400 MHz, available from Varian GmbH, Darmstadt, Germany).

Compound Synthesis:

Compounds of the invention that are of the 4,6-diarylpyrimidin-2(1H)-one class can be synthesized by the synthetic route outlined in Scheme 1. Thus, commercially available 1-[(4-hydroxy-3-methyl)phenyl]ethanone (1a) is protected as the corresponding benzyl ether (1b) using standard techniques. Condensation then with a suitably Scheme 1

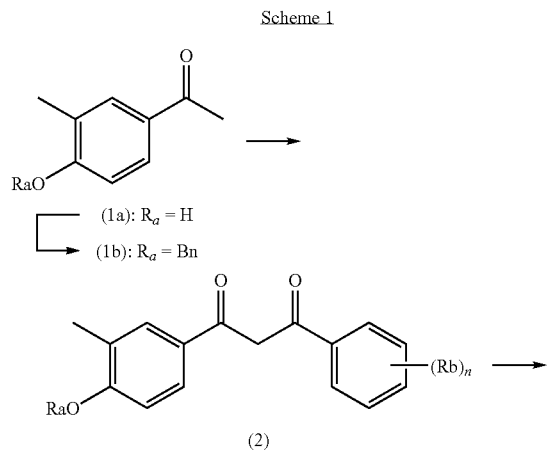

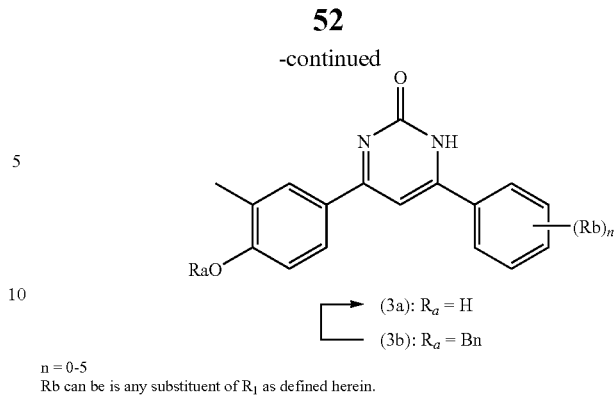

n = 0-5
Rb can be is any substituent of R$_1$ as defined herein.

functionalized benzoate ester is typically carried out by heating the mixture in the presence of a base such as sodium hydride to give a diketone intermediate (2). Reaction with urea under acidic condition with heating affords a pyrimidin-2(1H)-one (3b), which is then de-benzylated to afford a compound of the invention (3a) by treatment with trifluoroacetic acid, see: Greene T. W. and Wuts P. G. in Protective Groups in Organic Synthesis, Wiley-Interscience. Scheme 2 illustrates the general method of synthesis for compounds of the invention where the phenol aryl ring is replaced by an indazole. In this Scheme 2

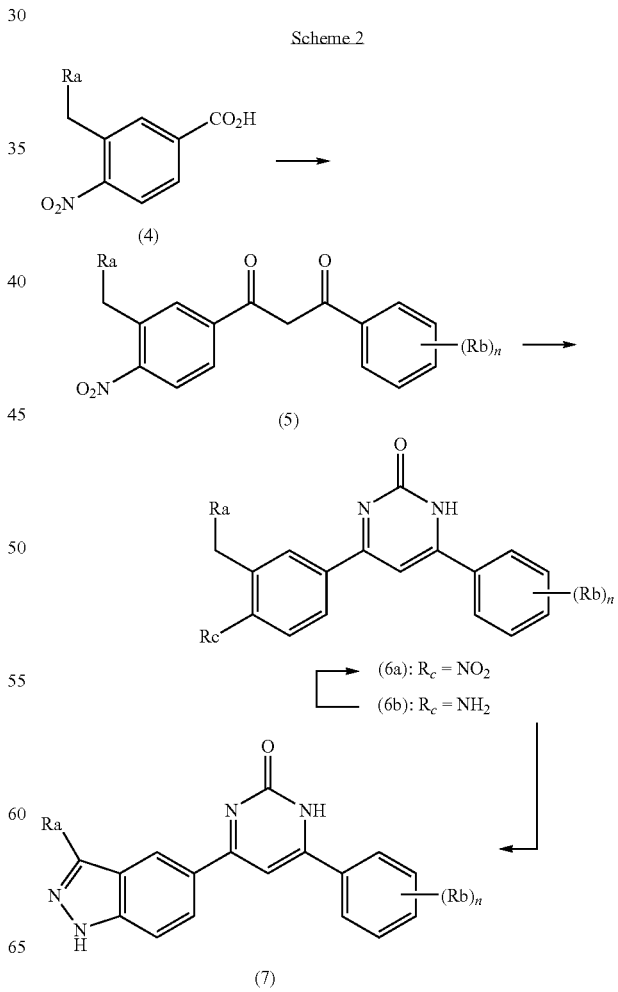

instance a 3-alkyl-4-nitrobenzoic acid (4) is converted to diketone (5) then cyclized by treatment with urea to give pyrimidin-2(1H)-one (6a) as before. Reduction of the nitroarene to the corresponding aniline (6b) can be carried out by a range of techniques including for example, reaction with tin (II) chloride. The resulting 3-alkyl-4-aminoaryl moiety can then be converted to the corresponding indazole (7) by making use of the Jacobson indazole synthesis, see: 1) Simplification of the Jacobson indazole-synthesis. Ruechardt, Christoph; Hassmann, Volker. Synthesis (1972), (7), 375-6. 2) Indazole. Huisgen, Rolf; Bast, Klaus. Organic Syntheses (1962), 42, 69-72, which is incorporated herein by reference.

EXAMPLES

The following examples serve to provide further appreciation of the invention, but are not meant in any way to restrict the effective scope of the invention.

Example 1

4-(4-hydroxy-3-methylphenyl)-6-(2-{[2-(methyloxy)ethyl]oxy}phenyl)pyrimidin-2(1H)-one hydrochloride (Compound 30)

A solution of 1-[(4-hydroxy-3-methyl)phenyl]ethanone (2.0 g, 13 mmol), potassium carbonate (3.7 g, 27 mmol) and (bromomethyl)benzene (1.6 mL, 13 mmol) in acetone was heated in a 60° C. oil bath for 2 h. The reaction mixture was concentrated in vacuo then partitioned between ethyl acetate and water. The layers were separated and the aqueous layer was extracted with ethyl acetate. The combined organic layers were dried over anhydrous sodium sulfate, filtered and concentrated in vacuo. Column chromatography (silica gel, 10:1 hexanes/ethyl acetate) gave 3.0 g (94%) of 1-{3-methyl-4-[(phenylmethyl)oxy]phenyl}ethanone as a white crystalline solid. $^1$H NMR (400 MHz, CDCl$_3$): 7.80 (m, 2H), 7.34-7.45 (m, 5H), 6.90 (d, 1H), 5.16 (s, 2H), 2.55 (s, 3H), 2.32 (s, 3H).

To a solution of 1-{3-methyl-4-[(phenylmethyl)oxy]phenyl}ethanone (0.81 g, 3.4 mmol) in tetrahydrofuran (11 mL) was added sodium hydride (0.27 g, 6.7 mmol) followed by methyl 2-{[2-(methyloxy)ethyl]oxy}benzoate (0.70 g, 3.4 mmol, Harkin, S. H.; Wells, N. S., GB Patent 2250511, 1992) and the resultant mixture was heated in a 60° C. oil bath for 12 h. The solution was allowed to cool to room temperature and was diluted with water then 1M aqueous hydrochloric acid. The mixture was extracted (3× ethyl acetate) and the combined organic layers were dried over anhydrous sodium sulfate, filtered and concentrated in vacuo. Column chromatography (silica gel, 5:1 hexanes/ethyl acetate) gave 0.24 g (17%) of 1-(2-{[2-(methyloxy)ethyl]oxy}phenyl)-3-{3-methyl-4-[(phenylmethyl)oxy]phenyl}propane-1,3-dione as a colorless oil. $^1$H NMR (400 MHz, CDCl$_3$): 8.01 (dd, 1H), 7.89 (m, 2H), 7.34-7.45 (m, 7H), 7.08 (t, 1H), 6.97 (d, 1H), 6.92 (d, 1H), 5.17 (s, 2H), 4.24 (m, 2H), 3.85 (m, 2H), 3.42 (s, 3H), 2.34 (s, 3H).

A solution of 1-(2-{[2-(methyloxy)ethyl]oxy}phenyl)-3-{3-methyl-4-[(phenylmethyl)oxy]phenyl}propane-1,3-dione (0.24 g, 0.56 mmol), urea (0.34 g, 5.6 mmol), 4.0M hydrochloric acid in dioxane (1.4 mL, 5.6 mmol) in ethanol (2 mL) was heated in a 110° C. oil bath for 12 h. The solution was allowed to cool to room temperature and was concentrated in vacuo. The residue was partitioned between ethyl acetate (10% methanol) and aqueous saturated sodium bicarbonate. The layers were separated and the aqueous layer was extracted with ethyl acetate (2×). The combined organic layers were dried over anhydrous sodium sulfate, filtered and concentrated in vacuo. This crude mixture was taken up in 2.0 mL trifluoroacetic acid and heated in an 80° C. oil bath for 1 hour then concentrated. Purification of the residue by HPLC (reverse-phase, acetonitrile/water with 0.1% trifluoroacetic acid), followed by concentration in vacuo, treatment with methanol and 4.0 M hydrochloric acid in dioxane, and lyophilization gave the title compound 4-(4-hydroxy-3-methylphenyl)-6-(2-{[2-(methyloxy)ethyl]oxy}phenyl)pyrimidin-2(1H)-one hydrochloride (0.037 g, 19%). $^1$H NMR (400 MHz, d$_6$-DMSO): 11.07 (s, 1H), 8.01 (d, 1H), 7.92 (dd, 1H), 7.74 (dd, 1H), 7.63 (dt, 1H), 7.47 (s, 1H), 7.29 (d, 1H), 7.19 (dt, 1H), 7.10 (d, 1H), 4.29 (m, 2H), 3.71 (m, 2H), 3.27 (s, 3H), 2.20 (s, 3H). MS (EI) for C$_{20}$H$_{20}$N$_2$O$_4$: 352 (MH$^+$).

Example 2

6-phenyl-4-[4-(trifluoromethyl)phenyl]pyrimidin-2(1H)-one (Compound 1)

Using the same or analogous synthetic techniques described in Example 1, 6-phenyl-4-[4-(trifluoromethyl)phenyl]pyrimidin-2(1H)-one was prepared by replacing 1-[(4-hydroxy-3-methyl)phenyl]ethanone with commercially available 1-[(4-trifluoromethyl)phenyl]ethanone and replacing methyl 2-{[2-(methyloxy)ethyl]oxy}benzoate with commercially available methyl benzoate.

Example 3

6-(4-bromophenyl)-4-(4-hydroxy-3-methylphenyl)pyrimidin-2(1H)-one (Compound 2)

Using the same or analogous synthetic techniques described in Example 1, 6-(4-bromophenyl)-4-(4-hydroxy-3-methylphenyl)pyrimidin-2(1H)-one was prepared by replacing methyl 2-{[2-(methyloxy)ethyl]oxy}benzoate with commercially available methyl 4-bromobenzoate.

Example 4

4-(1-methyl-1H-pyrrol-2-yl)-6-phenylpyrimidin-2(1H)-one (Compound 3)

Using the same or analogous synthetic techniques described in Example 1, 4-(1-methyl-1H-pyrrol-2-yl)-6-phenylpyrimidin-2(1H)-one was prepared by replacing 1-[(4-hydroxy-3-methyl)phenyl]ethanone with commercially available 2-acetyl-N-methylpyrrole and replacing methyl 2-{[2-(methyloxy)ethyl]oxy}benzoate with commercially available methyl benzoate.

Example 5

4-(4-chlorophenyl)-6-phenylpyrimidin-2(1H)-one (Compound 4)

Using the same or analogous synthetic techniques described in Example 1, 4-(4-chlorophenyl)-6-phenylpyrimidin-2(1H)-one was prepared.

Example 6

4-(4-fluorophenyl)-6-phenylpyrimidin-2(1H)-one (Compound 5)

Using the same or analogous synthetic techniques described in Example 1, 4-(4-fluorophenyl)-6-phenylpyrimidin-2(1H)-one was prepared by replacing 1-[(4-hydroxy-3-methyl)phenyl]ethanone with commercially available 1-[(4-fluoro)phenyl]ethanone and replacing methyl 2-{[2-(methyloxy)ethyl]oxy}benzoate with commercially available methyl benzoate.

Example 7

4-(4-fluoro-3-methylphenyl-6-phenylpyrimidin-2 (1H)-one (Compound 6)

Using the same or analogous synthetic techniques described in Example 1, 4-(4-fluoro-3-methylphenyl)-6-phenylpyrimidin-2(1H)-one was prepared by replacing 1-[(4-hydroxy-3-methyl)phenyl]ethanone with commercially available acetophenone and methyl 2-{[2-(methyloxy)ethyl]oxy}benzoate with commercially available 4-fluoro-3-methylbenzoic acid.

Example 8

4-(3-hydroxyphenyl)-6-phenylpyrimidin-2(1H)-one (Compound 7)

Using the same or analogous synthetic techniques described in Example 1, 4-(3-hydroxyphenyl)-6-phenylpyrimidin-2(1H)-one was prepared by replacing 1-[(4-hydroxy-3-methyl)phenyl]ethanone with commercially available 1-[(3-hydroxy)phenyl]ethanone and replacing methyl 2-{[2-(methyloxy)ethyl]oxy}benzoate with commercially available methyl benzoate.

Example 9

6-[2-(methyloxy)phenyl]-4-{3-methyl-4-[(phenylmethyl)oxy]phenyl}pyrimidin-2(1H)-one (Compound 8)

Using the same or analogous synthetic techniques described in Example 1, 6-[2-(methyloxy)phenyl]-4-{3-methyl-4-[(phenylmethyl)oxy]phenyl}pyrimidin-2(1H)-one was prepared by replacing methyl 2-{[2-(methyloxy)ethyl]oxy}benzoate with commercially available methyl 2-(methyloxy)benzoate.

Example 10

6-[3-(methyloxy)phenyl]-4-{3-methyl-4-[(phenylmethyl)oxy]phenyl}pyrimidin-2(1H)-one (Compound 9)

Using the same or analogous synthetic techniques described in Example 1, 6-[3-(methyloxy)phenyl]-4-{3-methyl-4-[(phenylmethyl)oxy]phenyl}pyrimidin-2(1H)-one was prepared by replacing methyl 2-{[2-(methyloxy)ethyl]oxy}benzoate with commercially available methyl 3-(methyloxy)benzoate.

Example 11

4-(4-hydroxy-3-methylphenyl)-6-[2-(methyloxy) phenyl]pyrimidin-2(1H)-one (Compound 10)

Using the same or analogous synthetic techniques described in Example 1, 4-(4-hydroxy-3-methylphenyl)-6-[2-(methyloxy)phenyl]pyrimidin-2(1H)-one was prepared by replacing methyl 2-{[2-(methyloxy)ethyl]oxy}benzoate with commercially available methyl 2-(methyloxy)benzoate.

Example 12

4-(4-hydroxy-3-methylphenyl)-6-[3-(methyloxy) phenyl]pyrimidin-2(1H)-one (Compound 11)

Using the same or analogous synthetic techniques described in Example 1, 4-(4-hydroxy-3-methylphenyl)-6-[3-(methyloxy)phenyl]pyrimidin-2(1H)-one was prepared by replacing methyl 2-{[2-(methyloxy)ethyl]oxy}benzoate with commercially available methyl 3-(methyloxy)benzoate.

Example 13

4-(4-hydroxy-3-methylphenyl)-6-[4-(methyloxy) phenyl]pyrimidin-2(1H)-one (Compound 12)

Using the same or analogous synthetic techniques described in Example 1, 4-(4-hydroxy-3-methylphenyl)-6-[4-(methyloxy)phenyl]pyrimidin-2(1H)-one was prepared by replacing methyl 2-{[2-(methyloxy)ethyl]oxy}benzoate with commercially available methyl 4-(methyloxy)benzoate.

Example 14

4-(4-hydroxy-3-methylphenyl)-6-[4-(trifluoromethyl)phenyl]pyrimidin-2(1H)-one (Compound 13)

Using the same or analogous synthetic techniques described in Example 1, 4-(4-hydroxy-3-methylphenyl)-6-[4-(trifluoromethyl)phenyl]pyrimidin-2(1H)-one was prepared by replacing methyl 2-{[2-(methyloxy)ethyl] oxy}benzoate with commercially available methyl 4-(trifluoromethyl)benzoate.

Example 15

4-(4-hydroxy-3-methylphenyl)-6-(4-methylphenyl) pyrimidin-2(1H)-one (Compound 14)

Using the same or analogous synthetic techniques described in Example 1, 4-(4-hydroxy-3-methylphenyl)-6-(4-methylphenyl)pyrimidin-2(1H)-one was prepared by replacing methyl 2-{[2-(methyloxy)ethyl]oxy}benzoate with commercially available methyl 4-(methyl)benzoate.

Example 16

4-(4-hydroxy-3-methylphenyl)-6-(4-hydroxyphenyl) pyrimidin-2(1H)-one (Compound 15)

Using the same or analogous synthetic techniques described in Example 1, 4-(4-hydroxy-3-methylphenyl)-6-(4-hydroxyphenyl)pyrimidin-2(1H)-one was prepared by replacing methyl 2-{[2-(methyloxy)ethyl]oxy}benzoate with commercially available methyl 4-(hydroxy)benzoate.

Example 17

4-(3-aminophenyl)-6-phenylpyrimidin-2(1H)-one (Compound 16)

Using the same or analogous synthetic techniques described in Example 1, 4-(3-aminophenyl)-6-phenylpyrimidin-2(1H)-one was prepared by replacing 1-[(4-hydroxy-3- methyl)phenyl]ethanone with commercially available 1-[(3-amino)phenyl]ethanone and replacing methyl 2-{[2-(methyloxy)ethyl]oxy}benzoate with commercially available methyl benzoate.

Example 18

6-[2-bromo-5-(methyloxy)phenyl]-4-(4-hydroxy-3-methylphenyl)pyrimidin-2(1H)-one (Compound 17)

Using the same or analogous synthetic techniques described in Example 1, 6-[2-bromo-5-(methyloxy)phenyl]-4-(4-hydroxy-3-methylphenyl)pyrimidin-2(1H)-one was prepared by replacing methyl 2-{[2-(methyloxy)ethyl]oxy}benzoate with commercially available methyl 2-bromo-5-(methyloxy)benzoate.

Example 19

6-(4-chlorophenyl)-4-(4-hydroxy-3-methylphenyl)pyrimidin-2(1H)-one (Compound 18)

Using the same or analogous synthetic techniques described in Example 1, 6-(4-chlorophenyl)-4-(4-hydroxy-3-methylphenyl)pyrimidin-2(1H)-one was prepared by replacing methyl 2-{[2-(methyloxy)ethyl]oxy}benzoate with commercially available methyl 4-(chloro)benzoate.

Example 20

4-(4-hydroxy-3-methylphenyl)-6-(phenylamino)pyrimidin-2(1H)-one (Compound 19)

Using the same or analogous synthetic techniques described in Example 1, 4-(4-hydroxy-3-methylphenyl)-6-[4-(methyloxy)phenyl]pyrimidin-2(1H)-one was prepared by replacing methyl 2-{[2-(methyloxy)ethyl]oxy}benzoate with commercially available methyl benzoate.

Example 21

6-(2-chlorophenyl)-4-(4-hydroxy-3-methylphenyl)pyrimidin-2(1H)-one (Compound 20)

Using the same or analogous synthetic techniques described in Example 1, 6-(2-chlorophenyl)-4-(4-hydroxy-3-methylphenyl)pyrimidin-2(1H)-one was prepared by replacing methyl 2-{[2-(methyloxy)ethyl]oxy}benzoate with commercially available methyl 2-(chloro)benzoate.

Example 22

4-[4-hydroxy-3-(methyloxy)phenyl]-6-phenylpyrimidin-2(1H)-one (Compound 21)

Using the same or analogous synthetic techniques described in Example 1, 4-[4-hydroxy-3-(methyloxy)phenyl]-6-phenylpyrimidin-2(1H)-one was prepared by replacing 1-[(4-hydroxy-3-methyl)phenyl]ethanone with commercially available 1-[(4-hydroxy-3-methyloxy)phenyl]ethanone and replacing methyl 2-{[2-(methyloxy)ethyl]oxy}benzoate with commercially available methyl benzoate.

Example 23

4-(3-chloro-4-hydroxyphenyl)-6-phenylpyrimidin-2(1H)-one (Compound 22)

Using the same or analogous synthetic techniques described in Example 1, 4-(3-chloro-4-hydroxyphenyl)-6-phenylpyrimidin-2(1H)-one was prepared by replacing 1-[(4-hydroxy-3-methyl)phenyl]ethanone with commercially available 1-[(3-chloro-4-hydroxy)phenyl]ethanone and replacing methyl 2-{[2-(methyloxy)ethyl]oxy}benzoate with commercially available methyl benzoate.

Example 24

4-(3 ethyl-4-hydroxyphenyl)-6-phenylpyrimidin-2(1H)-one (Compound 23)

Using the same or analogous synthetic techniques described in Example 1, 4-(3-ethyl-4-hydroxyphenyl)-6-phenylpyrimidin-2(1H)-one was prepared by replacing methyl 2-{[2-(methyloxy)ethyl]oxy}benzoate with commercially available methyl benzoate, and by replacing 1-[(4-hydroxy-3-methyl)phenyl]ethanone with 1-[(4-hydroxy-3-ethyl)phenyl]ethanone prepared according to Leclerc, Gerard; Bizec, Jean Claude; Bieth, Nicole, Schwartz, Jean. Synthesis and structure-activity relationships among α-adrenergic receptor agonists of the phenylethanolamine type. Journal of Medicinal Chemistry (1980), 23(7), 738-744, and Example 25

6-[6-oxo-1-(phenylmethyl)-1,6-dihydropyridin-3-yl]-4-phenylpyrimidin-2(1H)-one (Compound 24)

Using the same or analogous synthetic techniques described in Example 1, 6-[6-oxo-1-(phenylmethyl)-1,6-dihydropyridin-3-yl]-4-phenylpyrimidin-2(1H)-one was prepared by replacing of methyl 2-{[2-(methyloxy)ethyl]oxy}benzoate with commercially available methyl benzoate, and by replacing 1-[(4-hydroxy-3-methyl)phenyl]ethanone with 1-[(4-hydroxy-3-ethyl)phenyl]ethanone prepared according to Fujii, Tozo; Yoshifuji, Shigeyuki. Lactams. I. Synthesis and acid hydrolysis of 4- and 5-substituted-1-benzyl-2-piperidone derivatives. Tetrahedron (1970), 26(24), 5953-8.

Example 26

6-[4-hydroxy-3-(1-methylethyl)phenyl]-4-phenylpyrimidin-2(1H)-one (Compound 25)

Using the same or analogous synthetic techniques described in Example 1, 6-[4-hydroxy-3-(1-methylethyl)phenyl]-4-phenylpyrimidin-2(1H)-one was prepared by replacing methyl 2-{[2-(methyloxy)ethyl]oxy}benzoate with commercially available methyl benzoate, and by replacing 1-[(4-hydroxy-3-methyl)phenyl]ethanone with 1-[4-hydroxy-3-(1-methylethyl)phenyl]ethanone prepared according to Leclerc, Gerard; Bizec, Jean Claude; Bieth, Nicole; Schwartz, Jean. Synthesis and structure-activity relationships among α-adrenergic receptor agonists of the phenylethanolamine type. Journal of Medicinal Chemistry (1980), 23(7), 738-744.

Example 27

4-(3-bromophenyl)-6-(4-hydroxy-3-methylphenyl)pyrimidin-2(1H)-one (Compound 26)

Using the same or analogous synthetic techniques described in Example 1, 4-(3-bromophenyl)-6-(4-hydroxy-3-methylphenyl)pyrimidin-2(1H)-one was prepared by replac-

Example 28

4-(2-bromophenyl)-6-(4-hydroxy-3-methylphenyl) pyrimidin-2(1H)-one (Compound 27)

Using the same or analogous synthetic techniques described in Example 1, 4-(2-bromophenyl)-6-(4-hydroxy-3-methylphenyl)pyrimidin-2(1H)-one was prepared by replacing methyl 2-{[2-(methyloxy)ethyl]oxy}benzoate with commercially available methyl 2-(bromo)benzoate.

Example 29

4-(4-amino-3-methylphenyl)-6-phenylpyrimidin-2 (1H)-one (Compound 28)

Using the same or analogous synthetic techniques described in Example 1, 4-(4-amino-3-methylphenyl)-6-phenylpyrimidin-2(1H)-one was prepared by replacing 1-[(4-hydroxy-3-methyl)phenyl]ethanone with commercially available acetophenone, and by replacing methyl 2-{[2-(methyloxy)ethyl]oxy}benzoate with commercially available 3-amino-4-methylbenzoic acid.

Example 30

4-(4-fluoro-3-methylphenyl)-6-[2-(methyloxy)phenyl]pyrimidin-2(1H)-one (Compound 29)

Using the same or analogous synthetic techniques described in Example 1, 4-(4-fluoro-3-methylphenyl)-6-[2-(methyloxy)phenyl]pyrimidin-2(1H)-one was prepared.

Example 31

4-(4-hydroxy-3-methylphenyl)-6-(3-{[2-(methyloxy) ethyl]oxy}phenyl)pyrimidin-2(1H)-one (Compound 31)

Using the same or analogous synthetic techniques described in Example 1, 4-(4-hydroxy-3-methylphenyl)-6-(3-{[2-(methyloxy)ethyl]oxy}phenyl)pyrimidin-2(1H)-one was prepared by replacing methyl 2-{[2-(methyloxy)ethyl]oxy}benzoate with methyl 3-{[2-(methyloxy)ethyl]oxy}benzoate prepared according to Nitz, Theodore J.; Gaboury, Janet A.; Burns, Christopher J.; Laquerre, Sylvie; Pevear, Daniel C.; Lessen, Thomas A.; Rys, David J. Preparation of Triaryl Bistetrazole Derivatives for Treating or Preventing Pneumovirus Infection and associated diseases. PCT Int. Appl. (2004), 130 pp. WO 2004014316 A2 20040219 CAN 140:181452 AN 2004:142913.

Example 32

4-(4-hydroxy-3-methylphenyl)-6-(4-{[2-(methyloxy) ethyl]oxy}phenyl)pyrimidin-2(1H)-one (Compound 32)

Using the same or analogous synthetic techniques described in Example 1, 4-(4-hydroxy-3-methylphenyl)-6-(4-{[2-(methyloxy)ethyl]oxy}phenyl)pyrimidin-2(1H)-one was prepared by replacing methyl 2-{[2-(methyloxy)ethyl]oxy}benzoate with methyl 4-{[2-(methyloxy)ethyl]oxy}benzoate prepared according to Abe, Hidenori; Matsunaga, Shinichiro; Takekawa, Shiro; Watanabe, Masanori. Preparation of indole amino acid derivatives as somatostatin agonists or antagonists. PCT Int. Appl. (2004), 482 pp. WO 2064046107 A1 20040603 CAN 141:23903 AN 2004:453183.

Example 33

6-(2-{[2-(diethylamino)ethyl]oxy}phenyl)-4-(4-hydroxy-3-methylphenyl)pyrimidin-2(1H)-one (Compound 33)

Using the same or analogous synthetic techniques described in Example 1, 6-(2-{[2-(diethylamino)ethyl] oxy}phenyl)-4-(4-hydroxy-3-methylphenyl)pyrimidin-2 (1H)-one was prepared by replacing methyl 2-{[2-(methyloxy)ethyl]oxy}benzoate with methyl 2-{[2-(diethylamino) ethyl]oxy}benzoate prepared according to Dall'Asta, Leone; Pedrazzoli, Andrea. Derivatives of salicyloylhydrazines. Bulletin de la Societe Chimique de France (1968), (1), 414-19.

Example 34

4-(1H-indazol-5-yl)-6-phenylpyrimidin-2(1H)-one (Compound 34)

A solution of 1,1,1-trimethyl-N-(trimethylsilyl)silanamine (2.70 g, 16.8 mmol) in dry tetrahydrofuran (40 mL) was cooled to −78° C., at which time was added n-butyllithium 1.6 N (10.5 mL, 16.8 mmol) followed by commercially available acetophenone (5.50 g, 31 mmol). The reaction mixture was stirred for 1 h at −78° C. to give the 1-[2-(propyloxy)phenyl] ethanone lithium salt. Concurrent with the above was prepared a solution of 1-[(3-methyl-4-nitrophenyl)carbonyl]-1H-imidazole by adding 1,1'-carbonylbis(1H-imidazole) (2.70 g, 16.8 mmol) to 3-methyl-2-nitrobenzoic acid (2.50 g, 14.0 mmol) in tetrahydrofuran (40 mL) at room temperature. To the 1-[2-(propyloxy)phenyl]ethanone lithium salt solution was slowly added the 1-[(3-methyl-4-nitrophenyl)carbonyl]-1H-imidazole solution at −78° C. and the mixture was allowed to warm to room temperature. The reaction mixture was quenched with hydrochloric acid 1.0 N (100 mL) and the product was extracted with ethyl acetate (150 mL). The organic phase was washed with brine (80 mL), dried over anhydrous sodium sulfate, filtered and concentrated in vacuo. The residue was purified by flash chomatography (SiO$_2$, ethyl acetate/hexanes 1:2), followed by re-crystallization from diethyl ether and hexanes (1:5) to afford (1Z)-3-imino-3-(3-methyl-4-nitrophenyl)-1-[2-(propyloxy)phenyl]prop-1-en-1-amine (2.20 g, 46%).

To a solution of (1Z)-3-imino-3-(3-methyl-4-nitrophenyl)-1-[2-(propyloxy)phenyl]prop-1-en-1-amine (2.20 g, 6.45 mmol) in ethanol (100 mL) was added urea (6.0 g, 100 mmol) and hydrochloric acid in dioxane 4.0 N (25 mL) at room temperature. The reaction mixture was heated to 75° C. for 16 h, at which time it was concentrated in vacuo, diluted with water (200 mL) and adjusted to pH 10 with sodium hydroxide 2.0 N. The product was extracted with chloroform (200 mL) then diluted with hexanes (50 mL) to precipitate the product. The solid was filtered and washed with chloroform/hexanes (1:4) to give 4-(3-methyl-4-nitrophenyl)-6-[2-(propyloxy) phenyl]pyrimidin-2(1H)-one (1.80 g, 81%). MS (EI) for C$_{20}$H$_{19}$N$_4$O$_3$: 363 (MH$^+$).

A solution of 4-(3-methyl-4-nitrophenyl)-6-[2-(propyloxy)phenyl]pyrimidin-2(1l)-one (2.5 g, 6.85 mmol) and palladium on carbon 5% (catalytic amount) in methanol (100 mL) was stirred under hydrogen (1 atm) for 1.2 h. The suspension was filtered through Celite and the filtrate concentrated in vacuo to afford 4-(4-amino-3-methylphenyl)-6-[2-(propyloxy)phenyl]pyrimidin-2(1H)-one (2.10 g, 91%). MS (EI) for $C_{20}H_{22}N_3O_2$: 337 (MH$^+$).

To a stirred solution of 4-(4-amino-3-methylphenyl)-6-[2-(propyloxy)phenyl]pyrimidin-2(1H)-one (2.10 g, 6.27 mmol) and sodium acetate (3.10 g, 31.3 mmol) in chloroform (80 mL) at room temperature was added acetic anhydride (3.0 mL, 31.3 mmol) and stirred for 15 min. The reaction mixture was warmed to 75° C. and added drop-wise isoamyl nitrite (5.10 g, 38 mmol) then stirred at 65° C. for 18 h. The reaction mixture was cooled to room temperature and washed with water (100 mL) and saturated aqueous sodium bicarbonate (100 mL). The solution was dried over anhydrous sodium sulfate, concentrated in vacuo, and purified by flash chromatography (SiO$_2$, ethyl acetate/hexanes 1:2) to afford 1-acetyl-4-(1-acetyl-1H-indazol-5-yl)-6-[2-(propyloxy)phenyl]pyrimidin-2(1H)-one (1.06 g, 40%). MS (EI) for $C_{24}H_{22}N_4O_4$: 431 (MH$^+$).

To a solution of 1-acetyl-4-(1-acetyl-1H-indazol-5-yl)-6-[2-(propyloxy)phenyl]pyrimidin-2(1H)-one (1.06 g, 2.46 mmol) in methanol (100 mL) was added hydrogen chloride in dioxane 4.0 N (1.0 mL) and then refluxed for 30 min. The solution was evaporated in vacuo to afford the title compound (0.83 g, 98%) as the di-hydrochloride salt. $^1$H NMR (400 MHz, d$_6$-DMSO): 8.74 (s, 1H), 8.37 (s, 1H), 8.05 (d, 1H), 7.78 (t, 2H), 7.64 (t, 1H), 7.58 (s, 1H), 7.28 (d, 1H), 7.19 (t, 1H), 4.08 (t, 2H), 1.78 (m, 2H), 0.98 (t, 3H); MS (EI) for $C_{20}H_{18}N_4O_2$: 347 (MH$^+$).

Example 35

6-(3-{[2-(diethylamino)ethyl]oxy}phenyl)-4-(4-hydroxy-3-methylphenyl)pyrimidin-2(1H)-one (Compound 35)

Using the same or analogous synthetic techniques described in Example 1, 6-(3-{[2-(diethylamino)ethyl]oxy}phenyl)-4-(4-hydroxy-3-methylphenyl)pyrimidin-2(1H)-one was prepared by replacing methyl 2-{[2-(methyloxy)ethyl]oxy}benzoate with methyl 3-{[2-(diethylamino)ethyl]oxy}benzoate prepared according to Dall'Asta, Leone; Pedrazzoli, Andrea. Derivatives of salicyloylhydrazines. Bulletin de la Societe Chimique de France (1968), (1), 414-19.

Example 36

4-(4-hydroxy-3-methylphenyl)-6-{3-[(2-morpholin-4-ylethyl)oxy]phenyl}pyrimidin-2(1H)-one (Compound 36)

Using the same or analogous synthetic techniques described in Example 1, 4-(4-hydroxy-3-methylphenyl)-6-{3-[(2-morpholin-4-ylethyl)oxy]phenyl}pyrimidin-2(1H)-one was prepared by replacing of methyl 2-{[2-(methyloxy)ethyl]oxy}benzoate with methyl 3-[(2-morpholin-4-ylethyl)oxy]benzoate prepared according to Dall'Asta, Leone; Pedrazzoli, Andrea. Derivatives of salicyloylhydrazines. Bulletin de la Societe Chimique de France (1968), (1), 414-19.

Example 37

N-[3-(diethylamino)propyl]-3-[6-(4-hydroxy-3-methylphenyl)-2-oxo-2,3-dihydropyrimidin-4-yl]benzamide (Compound 37)

Using the same or analogous synthetic techniques described in Example 1, N-[3-(diethylamino)propyl]-3-[6-(4-hydroxy-3-methylphenyl)-2-oxo-2,3-dihydropyrimidin-4-yl]benzamide was prepared by replacing methyl 2-{[2-(methyloxy)ethyl]oxy}benzoate with dimethyl isophthalate followed by methyl ester hydrolysis and coupling with N,N-diethylpropane-1,3-diamine using standard synthetic methods.

Example 38

N-[2-(diethylamino)ethyl]-3-[6-(4-hydroxy-3-methylphenyl)-2-oxo-2,3-dihydropyrimidin-4-yl]benzamide (Compound 38)

Using the same or analogous synthetic techniques described in Example 1, N-[2-(diethylamino)ethyl]-3-[6-(4-hydroxy-3-methylphenyl)-2-oxo-2,3-dihydropyrimidin-4-yl]benzamide was prepared by replacing methyl 2-{[2-(methyloxy)ethyl]oxy}benzoate with dimethyl isophthalate followed by methyl ester hydrolysis and coupling with N,N-diethylethane-1,2-diamine using standard synthetic methods.

Example 39

6-(2,5-bis{[2-(methyloxy)ethyl]oxy}phenyl)-4-(4-hydroxy-3-methylphenyl)pyrimidin-2(1H)-one (Compound 39)

Using the same or analogous synthetic techniques described in Example 1, 6-(2,5-bis{[2-(methyloxy)ethyl]oxy}phenyl)-4-(4-hydroxy-3-methylphenyl)pyrimidin-2(1H)-one was prepared by replacing methyl 2-{[2-(methyloxy)ethyl]oxy}benzoate with methyl 2,5-bis(2-methoxyethoxy)benzoate prepared according to Abe, Hidenori; Matsunaga, Shinichiro; Takekawa, Shiro; Watanabe, Masanori. Preparation of indole amino acid derivatives as somatostatin agonists or antagonists. PCT Int. Appl. (2004), 482 pp. WO 2004046107 A1 20040603 CAN 141:23903 AN 2004:453183, and starting from commercially available methyl 2,5-dihydroxybenzoate.

$^1$H NMR (400 MHz, d$_6$-DMSO): 11.58 (s, 1H), 10.1 (s, 1H), 7.75-7.96 (m, 2H), 7.02-7.41 (m, 4H), 6.90 (d, 1H), 4.16 (m, 4H), 3.66 (m, 4H), 3.31 (s, 3H), 3.38 (s, 3H), 2.20 (s, 3H); MS (EI) for $C_{23}H_{26}N_2O_6$: 427 (MH$^+$).

Example 40

6-(2,4-bis{[2-(methyloxy)ethyl]oxy}phenyl)-4-(4-hydroxy-3-methylphenyl)pyrimidin-2(1H)-one (Compound 40)

Using the same or analogous synthetic techniques described in Example 1, 6-(2,4-bis{[2-(methyloxy)ethyl]oxy}phenyl)-4-(4-hydroxy-3-methylphenyl)pyrimidin-2(1H)-one was prepared by replacing methyl 2-{[2-(methyloxy)ethyl]oxy}benzoate with methyl 2,4-bis(2-methoxyethoxy)benzoate prepared according to Abe, Hidenori; Matsunaga, Shinichiro; Takekawa, Shiro; Watanabe, Masanori. Preparation of indole amino acid derivatives as somatostatin agonists or antagonists. PCT Int. Appl. (2004), 482 pp. WO 2004046107 A1 20040603 CAN 141:23903 AN 2004:453183, and starting from commercially available methyl 2,4-dihydroxybenzoate.

$^1$H NMR (400 MHz, d$_6$-DMSO): 11.33 (s, 1H), 10.6 (s, 1H), 7.87 (m, 2H), 6.89 (d, 2H), 6.65-6.79 (m, 3H), 4.23 (m, 4H), 3.70 (m, 4H), 3.33 (s, 3H), 3.31 (s, 3H), 2.20 (s, 3H); MS (EI) for $C_{23}H_{26}N_2O_6$: 427 (MH$^+$).

Example 41

4-(4-hydroxy-3-methylphenyl)-6-[2-(propyloxy) phenyl]pyrimidin-2(1H)-one (Compound 41)

Using the same or analogous synthetic techniques described in Example 1, 4-(4-hydroxy-3-methylphenyl)-6-[2-(propyloxy)phenyl]pyrimidin-2(1H)-one was prepared by replacing methyl 2-{[2-(methyloxy)ethyl]oxy}benzoate with methyl (2-propyloxy)benzoate prepared according to Rotella, David P.; Sun, Zhong; Zhu, Yeheng; Krupinski, John; Pongrac, Ronald; Seliger, Laurie; Normandin, Diane; Macor, John E. Optimization of Substituted N-3-Benzylimidazoquinazolinone Sulfonamides as Potent and Selective PDE5 Inhibitors. Journal of Medicinal Chemistry (2000), 43(26), 5037-5043.

$^1$H NMR (400 MHz, d$_6$-DMSO): 8.88 (broad s, 1H), 7.89 (s, 1H), 7.82 (d, 1H), 7.64 (d, 1H), 7.50 (t, 1H), 7.19 (s, 1H), 7.16 (d, 1H), 7.08 (t, 1H), 6.89 (d, 1H), 4.03 (t, 2H), 2.19 (s, 3H), 1.71-1.79 (m, 2H), 0.97 (t, 3H); MS (EI) for C$_{20}$H$_{20}$N$_2$O$_3$: 337 (MH$^+$).

Example 42

6-[2-(butyloxy)phenyl]-4-(4-hydroxy-3-methylphenyl)pyrimidin-2-(1H)-one: (Compound 42)

Using the same or analogous synthetic techniques described in Example 1, 6-[2-(butyloxy)phenyl]-4-(4-hydroxy-3-methylphenyl)pyrimidin-2-(1H)-one was prepared by replacing methyl 2-{[2-(methyloxy)ethyl]oxy}benzoate with methyl (2-butyloxy)benzoate prepared according to Coates, William J.; Connolly, Brendan; Dhanak, Dashyant; Flynn, Sean T.; Worby, Angela. Cyclic nucleotide phosphodiesterase inhibition by imidazopyridines: analogs of sulmazole and isomazole as inhibitors of the cGMP specific phosphodiesterase. Journal of Medicinal Chemistry (1993), 36(10), 1387-92.

$^1$H NMR (400 MHz, d$_6$-DMSO): 7.88 (s, 1H), 7.80 (d, 1H), 7.65 (d, 1H), 7.49 (t, 1H), 7.18 (d, 2H), 7.07 (t, 1H), 6.89 (d, 1H), 4.07 (t, 2H), 3.34 (s, 2H), 2.19 (s, 3H), 1.69-1.76 (m, 2H), 1.38-1.48 (m, 2H), 0.88 (t, 3H); MS (EI) for C$_{21}$H$_{22}$N$_2$O$_3$: 351 (MH$^+$).

Example 43

4-(4-hydroxy-3-methylphenyl)-6-[2-(prop-2-en-1-yloxy)phenyl]pyrimidin-2(1H)-one (Compound 47)

Using the same or analogous synthetic techniques described in Example 1, Using the same or analogous synthetic techniques described in Example 1, 6-[2-(butyloxy)phenyl]-4-(4-hydroxy-3-methylphenyl)pyrimidin-2-(1H)-one was prepared by replacing methyl 2-{[2-(methyloxy)ethyl]oxy}benzoate with methyl 2-(prop-2-en-yloxy)benzoate prepared according to Eissenstat, Michael A.; Bell, Malcolm R.; D'Ambra, Thomas E.; Alexander, E. John; Daum, Sol J.; Ackerman, James H.; Gruett, Monte D.; Kumar, Virendra; Estep, Kimberly G.; et al. Aminoalkylindoles: Structure-Activity Relationships of Novel Cannabinoid Mimetics. Journal of Medicinal Chemistry (1995), 38(16), 3094-105.

$^1$HNMR (400 MHz, d$_6$-DMSO): 7.98 (s, 1H), 7.90 (d, 1H), 7.67 (d, 1H), 7.59 (t, 1H), 7.32 (s, 1H), 7.24 (d, 1H), 7.15 (t, 1H), 6.97 (d, 1H), 6.03-6.13 (m, 1H), 5.42 (d, 1H), 5.27 (d, 1H), 4.70 (d, 2H), 2.20 (s, 3H); MS (EI) for C$_{20}$H$_{18}$N$_2$O$_3$: 335 (MH$^+$).

Example 44

4-(4-hydroxy-3-methylphenyl)-6-{2-[(2-methylpropyl)oxy]phenyl}pyrimidin-2(1H)-one (Compound 48)

Using the same or analogous synthetic techniques described in Example 1, Using the same or analogous synthetic techniques described in Example 1, 4-(4-hydroxy-3-methylphenyl)-6-{2-[(2-methylpropyl)oxy] phenyl}pyrimidin-2(1H)-one was prepared by replacing methyl 2-{[2-(methyloxy)ethyl]oxy}benzoate with methyl 2-[(2-methylpropyl)oxy]benzoate prepared according to Coates, William J.; Connolly, Brendan; Dhanak, Dashyant; Flynn, Sean T.; Worby, Angela. Cyclic nucleotide phosphodiesterase inhibition by imidazopyridines: analogs of sulmazole and isomazole as inhibitors of the cGMP specific phosphodiesterase. Journal of Medicinal Chemistry (1993), 36(10), 1387-92.

$^1$H NMR (400 MHz, d$_6$-DMSO): 10.56 (broad s, 1H), 7.97 (s, 1H), 7.88 (s, 1H), 7.67 (s, 1H), 7.56 (s, 1H), 7.40-7.46 (m, 1H), 7.29 (s, 1H), 7.21-7.23 (m, 1H), 7.09-7.14 (m, 1H), 6.92-6.96 (m, 1H), 3.88 (s, 2H), 2.19 (s, 2H), 2.00-2.08 (m, 1H), 0.97 (t, 6H); MS (EI) for C$_{21}$H$_{22}$N$_2$O$_3$: 351 (MH$^+$).

Example 45

4-(4-hydroxy-3-methylphenyl)-6-{2-[(3-methylbutyl)oxy]phenyl}pyrimidin-2(1H)-one (Compound 49)

Using the same or analogous synthetic techniques described in Example 1, Using the same or analogous synthetic techniques described in Example 1, 4-(4-hydroxy-3-methylphenyl)-6-{2-[(3-methylbutyl)oxy] phenyl}pyrimidin-2(1H)-one was prepared by replacing methyl 2-{[2-(methyloxy)ethyl]oxy}benzoate with methyl 2-[(3-methylbutyl)oxy]benzoate prepared according to Coates, William J.; Connolly, Brendan; Dhanak, Dashyant; Flynn, Sean T.; Worby, Angela. Cyclic nucleotide phosphodiesterase inhibition by imidazopyridines: analogs of sulmazole and isomazole as inhibitors of the cGMP specific phosphodiesterase. Journal of Medicinal Chemistry (1993), 36(10), 1387-92.

$^1$H NMR (400 MHz, d$_6$-DMSO): 10.56 (broad s, 1H), 7.94 (s, 1H), 7.85 (d, 1H), 7.66 (s, 1H), 7.56 (s, 1H), 7.23-7.28 (m, 2H), 7.11 (s, 1H), 6.94 (d, 1H), 4.11 (s, 2H), 2.20 (s, 3H), 1.76 (s, 1H), 1.65 (s, 2H), 0.89 (s, 6H); MS (EI) for C$_{22}$H$_{24}$N$_2$O$_3$: 365 (MH$^+$).

Example 46

4-(4-hydroxy-3-methylphenyl)-6-{2-[(3-hydroxypropyl)oxy]phenyl}pyrimidin-2(1H)-one (Compound 43)

Using the same or analogous synthetic techniques described in Example 1, Using the same or analogous synthetic techniques described in Example 1, 4-(4-hydroxy-3-methylphenyl)-6-{2-[(3-hydroxypropyl)oxy] phenyl}pyrimidin-2(1H)-one was prepared by replacing methyl 2-{[2-(methyloxy)ethyl]oxy}benzoate with methyl 2-(3-hydroxypropyl)benzoate prepared according to Smith, Keith; Morris, Ian K.; Owen, Philip G.; Bass, Robert J. Synthesis of novel macrocyclic lactones with potential pharmacological activity. Journal of the Chemical Society, Perkin Transactions 1: Organic and Bio-Organic Chemistry (1972-1999) (1988), (1), 77-83.

$^1$H NMR (400 MHz, d$_6$-DMSO): 10.62 (s, 1H), 7.99 (m, 1H), 7.89 (dd, 1H), 7.67 (dd, 1H), 7.58 (m, 1H), 7.32 (s, 1H), 7.24 (d, 1H), 7.12 (t, 1H), 6.94 (d, 1H), 4.52 (t, 1H), 4.18, (t, 2H), 3.54 (t, 2H), 2.19 (s, 3H), 1.88 (m, 1H); MS (EI) for C$_{20}$H$_{20}$N$_2$O$_4$: 353 (MH$^+$).

Example 47

4-(4-hydroxy-3-methylphenyl)-6-(2-{[3-(methyloxy) propyl]oxy}phenyl)pyrimidin-2(1H)-one (Compound 44)

Using the same or analogous synthetic techniques described in Example 1, 4-(4-hydroxy-3-methylphenyl)-6-(2-{[3-(methyloxy)propyl]oxy}phenyl)pyrimidin-2(1H)-one was prepared by replacing methyl 2-{[2-(methyloxy) ethyl]oxy}benzoate with methyl 2-[3-(methyloxy)propyl] benzoate prepared according to Irie, Osamu; Nihonyanagi, Atsuko; Toyao, Atsushi; Kanazawa, Takanori. Preparation of 3,4,(5)-substituted tetrahydropyridines as renin inhibitors. PCT Int. Appl. (2006) WO 2006074924 A1.

$^1$H NMR (400 MHz, d$_6$-DMSO): 10.14 (s, 1H), 7.93 (bs, 1H), 7.82 (bs, 1H), 7.62 (bs, 1H), 7.50 (m, 1H), 7.18 (d, 1H), 7.12 (bs, 1H), 7.08 (m, 1H), 6.88 (d, 1H), 4.11, (t, 2H), 3.44 (t, 2H), 3.16 (s, 3H); 2.19 (s, 3H), 1.94 (m, 1H); MS (EI) for C$_{21}$H$_{22}$N$_2$O$_4$: 367 (MH$^+$).

Example 48

4-(3-bromo-4-fluorophenyl)-6-phenylpyrimidin-2 (1H)-one hydrochloride (Compound 45)

Using the same or analogous synthetic techniques described in Example 1, 4-(3-bromo-4-fluorophenyl)-6-phenylpyrimidin-2(1H)-one hydrochloride was prepared by replacing 1-[(4-hydroxy-3-methyl)phenyl]ethanone with commercially available 1-[(3-bromo-4-fluoro)phenyl]ethanone, and by replacing methyl 2-{[2-(methyloxy)ethyl] oxy}benzoate with commercially available methyl benzoate.

$^1$H NMR (400 MHz, DMSO): 8.61 (dd, 1 h), 8.31 (m, 1H), 8.18 (d, 2H), 7.76 (m, 1H), 7.59 (m, 5H). MS (EI) for C16H10BrFN$_2$O: 345 (MH$^+$).

Example 49

4-(3-amino-1H-indazol-5-yl)-6-phenylpyrimidin-2 (1H)-one dihydrochloride (Compound 46)

To a solution of 1-(3-bromo-4-fluorophenyl)ethanone (3.0 g, 14 mmol) in tetrahydrofuran (15 mL) was added sodium hydride (1.6 g, 42 mmol), followed by benzoic anhydride (3.1 g, 14 mmol) and the resultant solution was stirred at room temperature for 2 hours. The solution was quenched with water and acidified to pH 5 using concentrated hydrochloric acid, then partitioned between water and ethyl acetate. The layers were separated and the aqueous layer was extracted (2×50 mL ethyl acetate). The combined organic layers were dried (sodium sulfate), filtered and concentrated in vacuo. Column chromatography (silica gel, 10:1 hexanes/ethyl acetate) gave 1.08 g (24% yield) of 1-(3-bromo-4-fluorophenyl)-3-phenylpropane-1,3-dione. $^1$H NMR (400 MHz, CDCl$_3$): 8.19 (d, 1H), 7.97 (d, 2H), 7.90 (m, 1H), 7.57 (t, 1H), 7.49 (t, 2H), 7.21 (t, 1H), 6.75 (s, 1H).

A solution of 1-(3-bromo-4-fluorophenyl)-3-phenylpropane-1,3-dione (1.08 g, 3.37 mmol), urea (2.03 g, 33.7 mmol) and 4.0 M hydrogen chloride in dioxane (8.4 mL) in ethanol (11 mL) was heated for 48 hours at 110° C. The mixture was then concentrated and taken back into 10 mL 4.0M hydrogen chloride in dioxane. An additional 2.0 g (33 mmol) of urea was added and the solution was again heated for 12 hours at 110° C. The resultant solution was partitioned between 10:1 ethyl acetate/methanol, and saturated sodium bicarbonate (aqueous). The layers were separated and the basic aqueous layer was extracted (2×100 mL ethyl acetate). The combined organic layers were dried (sodium sulfate), filtered and concentrated in vacuo. Column chromatography (silica gel, 95:5 dichloromethane/methanol) gave 0.66 g (57% yield) of 4-(3-bromo-4-fluorophenyl)-6-phenylpyrimidin-2(1H)-one. $^1$H NMR (400 MHz, DMSO): 8.61 (dd, 1 h), 8.31 (m, 1H), 8.18 (d, 2H), 7.76 (m, 1H), 7.59 (m, 5H).

A solution of 4-(3-bromo-4-fluorophenyl)-6-phenylpyrimidin-2(1H)-one (0.3 g, 0.9 mmol) and copper(I) cyanide (0.16 g, 1.7 mmol) in N,N-dimethylformamide (3 mL) was heated to 155° C. for 24 hours. The crude reaction mixture was concentrated in vacuo then partitioned between saturated sodium bicarbonate (aqueous) and ethyl acetate/methanol (10:1). The layers were separated and the aqueous layer was extracted once with 10:1 ethyl acetate/methanol. The combined organic layers were dried (sodium sulfate), filtered and concentrated in vacuo to give 0.30 g (quantitative yield) of crude 2-fluoro-5-(2-oxo-6-phenyl-1,2-dihydropyrimidin-4-yl)benzonitrile that was used without further purification for the next step. A solution of 2-fluoro-5-(2-oxo-6-phenyl-1,2-dihydropyrimidin-4-yl)benzonitrile (0.30 g, 1.0 mmol) and hydrazine monohydrate (1.7 mL, 36 mmol) in t-butanol (34 mL) was heated at 120° C. for 12 hours. The solution was concentrated in vacuo to give a solid, which was taken into hot methyl alcohol and treated with an excess of 4.0M hydrogen chloride in dioxane. After concentration in vacuo, the resultant solid was triturated in hot ethyl acetate, collected by vacuum filtration then lyophilized from aqueous solution to give 4-(3-amino-1H-indazol-5-yl)-6-phenylpyrimidin-2 (1H)-one dihydrochloride (0.034 g, 11% yield). $^1$H NMR (400 MHz, DMSO): 8.93 (broad s, 1H), 8.20 (d, 1H), 8.11 (d, 1H), 7.70 (t, 1H), 7.65 (t, 2H), 7.57 (broad s, 1H), 7.47 (d, 1H). MS (EI) for C$_{17}$H$_{13}$N$_5$O: 304 (MH$^+$).

Example 50

6-(4-bromo-2-methylphenyl)-4-(4-hydroxy-3-methylphenyl)pyrimidin-2(1H)-one (Compound 67)

Using the same or analogous synthetic techniques described in Example 1, 6-(4-bromo-2-methylphenyl)-4-(4-hydroxy-3-methylphenyl)pyrimidin-2(1H)-one was prepared by replacing methyl 2-{[2-(methyloxy)ethyl] oxy}benzoate with commercially available 4-bromo-2-methyl benzoic acid which was converted to the methyl ester by refluxing in HCl/MeOH.

$^1$H NMR (400 MHz, d$_6$-DMSO+D$_2$O): 7.95 (s, 1H), 7.86 (d, 1H), 7.61 (s, 1H), 7.58 (d, 1H), 7.40 (d, 1H), 6.97 (br s, 1H), 6.89 (d, 1H), 3.20 (s, 2H), 2.39 (s, 3H), 2.20 (s, 3H); MS (EI) for C$_{18}$H$_{15}$BrN$_2$O$_2$: 371:373 (1:1 Br isotope MH$^+$).

Alternatively, compounds of the 4,6-diarylpyrimidin-2 (1H)-one class can be synthesized by the synthetic route outlined in Scheme 2. Commercially available 2,4,6-trichloropyrimidine is converted to 4,6-diaryl-2-chloropyrimidine derivatives via two sequential Suzuki couplings. Hydrolysis of 4,6-diaryl-2-chloropyrimidine under concentrated hydrochloric acid with heating produces 4,6-diarylpyrimidin-2 (1H)-one. The Suzuki reagent 2-(isopentyloxy)phenylboronic acid is prepared from commercial available 2-bromophenol. Alkylation with 1-bromo-3-methylbutane gives 1-bromo-2-(isopentyloxy)benzene, which undergoes a bromo/lithium exchange reaction and then reacts with triethylborate to give 2-(isopentyloxy)phenyl boronic acid. Other Suzuki reagents not listed here are commercially available.

Scheme 2

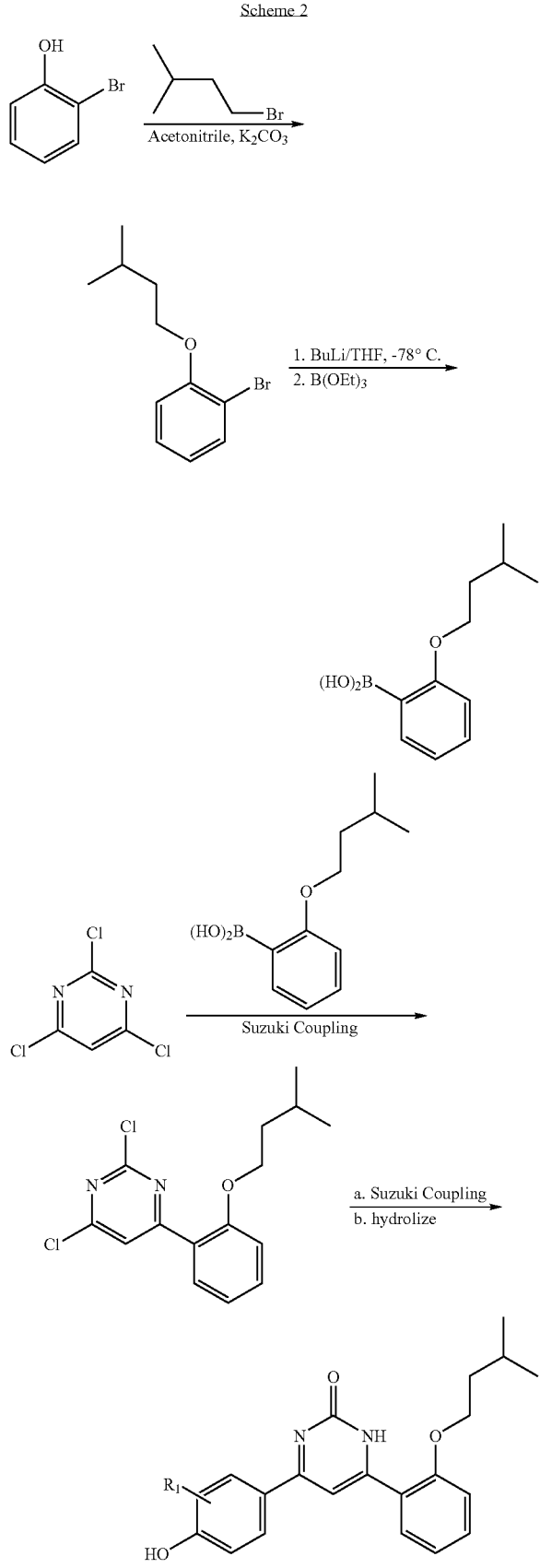

Example 51

4-(4-hydroxyphenyl)-6-(2-(isopentyloxy)phenyl) pyrimidin-2(1H)-one (Compound 51)

A 500 mL of round-bottom flask was charged with 2-bromophenol (43 g, 0.25 mol), 1-bromo-3-methylbutane (41 mL, 0.325 mol), acetonitrile (200 mL) and potassium carbonate (52 g). The reaction mixture was heated to 80° C. with stirring overnight. The reaction was cooled and filtered, and washed with acetonitrile. The filtrate was concentrated in vacuo. Vacuum distillation of the residue yielded 1-bromo-2-(isopentyloxy)benzene (83-86° C., 56 g, 93% yield).

To a solution of 1-bromo-2-(isopentyloxy)benzene (9.68 g, 40 mmol) in THF (160 mL) was added dropwise n-butyl lithium (1.6 M in hexanes, 1.05 eq., 26.3 mL) under nitrogen at −78° C. over 30 min. After further stirring for 1 hour at −78° C., triethylborate (5.86 mL, 51.3 mmol) was added. The cooling bath was removed and the reaction mixture was stirred overnight at rt. An aqueous solution of 2 N HCl (20 mL) was added and the reaction solution stirred for 30 min, at which point 50 mL of water was added. The reaction mixture was extracted with ether (5×80 mL), dried over anhydrous sodium sulfate, filtrated and concentrated to yield 2-(isopentyloxy)phenylboronic acid (6.30 g, 77% yield). $^1$H NMR (400 MHz, CDCl$_3$): 7.83 (d, 1H), 7.43 (dd, 1H), 7.03 (t, 1H), 6.93 (d, 1H), 6.05 (s, 2H), 4.10 (t, 2H), 1.86-1.75 (m, 3H), 1.0 (s, 6H).

To a solution of 2,4,6-trichloropyrimidine (40 mmol, 7.32 g) in 20 mL of THF was added 2-(isopentyloxy)phenylboronic acid (20 mmol, 4.1 g), Pd (OAc)$_2$ (2 mol %, 540 mg) and PPh$_3$ (4 mol %, 420 mg) followed by Na$_2$CO$_3$ (1M, 40 mL). The reaction was heated to 60° C. for 3 hours. Then the reaction mixture was partitioned between ethyl acetate and water. The organic layer was separated, dried with anhydrous sodium sulfate and concentrated. The residue was purified by silica gel chromatography column (hexanes to 5% EtOAc in hexanes) to give 2,4-dichloro-6-(2-(isopentyloxy)phenyl)pyrimidine (4.3 g, 70% yield). $^1$H NMR (400 MHz, CDCl$_3$): 8.18-8.12 (m, 2H), 7.50-7.44 (m, 1H), 7.08 (t, 1H), 7.01 (d, 1H), 4.15 (t, 2H), 1.90-1.80 (m, 1H), 1.78-1.70 (m, 2H), 1.0 (s, 6H).

To a solution of 2,4-dichloro-6-(2-(isopentyloxy)phenyl) pyrimidine (0.32 mmol, 100 mg) in 5 mL of THF was added 4-hydroxyphenylboronic acid (0.33 mmol, 46 mg), Pd(OAc)$_2$ (4 mol %, 10 mg) and PPh$_3$ (8 mol %, 9 mg) followed by Na$_2$CO$_3$ (1M, 1.20 mL). The reaction was heated to 60° C. for 2 hours, then concentrated in vacuo. 8 mL of conc. HCl was added to the reaction mixture which was heated to 90° C. Once the hydrolization was complete, the reaction was concentrated in vacuo. The residue was dissolved in methanol and passed through a stratosphere SPE cartridge (Polymer Labs) to remove Pd. Purification by HPLC (reverse-phase, acetonitrile/water with 0.01% ammonium acetate), followed by concentration in vacuo and lyophilization gave the title compound 4-(4-hydroxyphenyl)-6-(2-(isopentyloxy)phenyl) pyrimidin-2(1H)-one (35 mg, 30% yield). $^1$H NMR (400 MHz, d-4-MeOH): 8.03-7.97 (m, 2H), 7.67-7.63 (m, 1H), 7.56-7.51 (m, 1H), 7.22-7.18 (m, 2H), 7.15-7.10 (m, 1H), 6.93-6.90 (d, 2H), 4.17 (t, 2H), 1.85-1.70 (m, 3H), 0.95 (s, 3H), 0.93 (s, 3H). MS (EI) for C$_{21}$H$_{22}$N$_2$O$_3$: 351 (MH$^+$).

Example 52

4-(4-hydroxy-3,5-dimethylphenyl)-6-{2-[(3-methylbutyl)oxy]phenyl}pyrimidin-2(1H)-one (Compound 68)

4-(4-hydroxy-3,5-dimethylphenyl)-6-{2-[(3-methylbutyl)oxy]phenyl}pyrimidin-2(1H)-one was synthesized in a manner similar to 4-(4-hydroxyphenyl)-6-(2-(isopentyloxy)phenyl)pyrimidin-2(1H)-one (Example 51), wherein Suzuki reagent 3,5-dimethyl-4-hydroxyphenylboronic acid was substituted for 4-hydroxyphenylboronic acid. $^1$H NMR (400 MHz, d-4-MeOH): 7.75-7.65 (m, 3H), 7.55-7.48 (m, 1H), 7.22-7.17 (m, 2H), 7.10-7.05 (m, 1H), 4.17 (t, 2H), 2.25 (s, 6H), 1.82-1.70 (m, 3H), 0.95 (s, 3H), 0.92 (s, 3H). MS (I) for $C_{23}H_{26}N_2O_3$: 379 (MH$^+$).

Example 53

N-[2-(dimethylamino)ethyl]-N-ethyl-4-[6-(4-hydroxy-3-methylphenyl)-2-oxo-2,3-dihydropyrimidin-4-yl]benzamide (Compound 63)

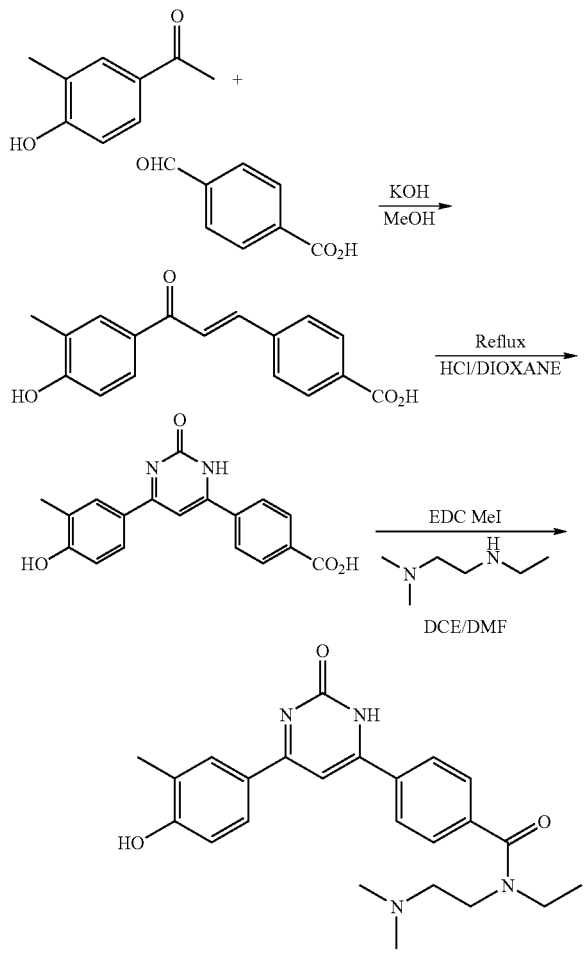

Step 1

(E)-4-(3-(4-hydroxy-3-methylphenyl)-3-oxoprop-1-enyl)benzoic acid

4-Formylbenzoic acid (15.0 g, 0.1 mol, Aldrich) and 4'-hydroxy-3'-methylacetophenone (15.0 g, 0.1 mol, Indofine) was dissolved in 150 mL of methanol and 50 mL of water. The solution was cooled with an ice-water bath, to which was added potassium hydroxide (28.0 g, 0.5 mol). The reaction mixture was stirred overnight. The resulted mixture was poured on to 600 mL of ice-water, acidified to pH=4-5 with 1 N HCl, filtered, washed with water (200 mL), and dried in the air. 25 g (87%) of (E)-4-(3-(3-(4-hydroxy-3-methylphenyl)-3-oxoprop-1-enyl)phenoxy)acetic acid were obtained. $^1$H NMR (400 MHz, DMSO-d$_6$): 10.20 (br, 1H), 10.11 (s, 1H), 8.00-8.15 (m, 3H), 7.78 (m, 2H), 6.65 (m, 4H), 2.40 (s, 3H). MS (EI) for $C_{17}H_{14}O_4$: 283 (MH$^+$).

Step 2

4-(6-(4-hydroxy-3-methylphenyl)-2-oxo-2,3-dihydropyrimidin-4-yl)benzoic acid

(E)-4-(3-(4-hydroxy-3-methylphenyl)-3-oxoprop-1-enyl)benzoic acid (14.7 g, 52.1 mmol) and urea (15.6 g, 0.26 mol) was suspended in 200 mL of 4N HCl solution in dioxane, and the reaction mixture was heated to reflux overnight, then cooled to room temperature. The resulted mixture was concentrated in vacuo to remove dioxane. The residues were suspended in 20 mL of methanol, filtered and washed with 50 mL of water, and dried in the air. 8.3 g (51%) of 4-(6-(4-hydroxy-3-methylphenyl)-2-oxo-2,3-dihydropyrimidin-4-yl)benzoic acid were obtained. $^1$H NMR (400 MHz, DMSO-d$_6$): 10.25 (s, 1H), 8.28 (m, 2H), 7.92-8.05 (m, 4H), 7.58 (s, 1H), 6.95 (m, 1H), 2.18 (s, 3H). MS (EI) for $C_{18}H_{14}N_2O_4$: 323 (MH$^+$).

Step 3

N-[2-(dimethylamino)ethyl]-N-ethyl-4-[6-(4-hydroxy-3-methylphenyl)-2-oxo-2,3-dihydropyrimidin-4-yl]benzamide

To a solution of 4-(6-(4-hydroxy-3-methylphenyl)-2-oxo-2,3-dihydropyrimidin-4-yl)benzoic acid (16.9 mg, 48 μmol) and N,N-dimethyl-N'-ethylethylenediamine (4.6 mg, 40 μmol) in dichloroethane (1.25 mL) and N,N-dimethylformamide (0.79 mL) was added 1-hydroxybenzotriazole (6.8 mg, 50 μmol) followed by 1-[3-(dimethylamino)propyl]-3-ethylcarbodiimide methiodide (17.8 mg, 60 μmol). The resultant mixture was stirred at room temperature for 15 hours. The reaction mixture was concentrated in vacuo. Purification of the residue by HPLC (reverse-phase, acetonitrile/water with 0.1% formic acid) followed by concentration in vacuo gave the title compound N-[2-(dimethylamino)ethyl]-N-ethyl-4-[6-(4-hydroxy-3-methylphenyl)-2-oxo-2,3-dihydropyrimidin-4-yl]benzamid (3 mg, 20%). $^1$H NMR (400 MHz, d$_6$-DMSO): 8.21 (m, 3H), 7.97 (s, 1H), 7.87 (dd, 1H), 7.49 (m, 3H), 6.90 (d, 1H), 3.41 (m, 4H), 2.33 (m, 2H), 2.22 (m, 6H), 1.97 (s, 3H), 1.10 (m, 3H); MS (EI) for $C_{24}H_{28}N_4O_3$: 421 (MH$^+$).

Example 54

N-[2-(dimethylamino)ethyl]-4-[6-(4-hydroxy-3-methylphenyl)-2-oxo-2,3-dihydropyrimidin-4-yl]benzamide (Compound 64)

N-[2-(dimethylamino)ethyl]-4-[6-(4-hydroxy-3-methylphenyl)-2-oxo-2,3-dihydropyrimidin-4-yl]benzamide was synthesized in a manner similar to Example 53, wherein and N,N-dimethyl-N'-ethylethylenediamine was substituted for N,N-dimethylethylenediamine. Purification by preparative HPLC resulting in 3 mg (20% Yield) of N-[2-(dimethylamino)ethyl]-4-[6-(4-hydroxy-3-methylphenyl)-2-oxo-2,3-dihydropyrimidin-4-yl]benzamide. $^1$H NMR (400 MHz, d$_6$-DMSO): 8.59 (t, 1H), 8.21 (m, 3H), 7.98 (m, 3H), 7.89 (dd, 1H), 7.50 (s, 1H), 6.91 (d, 1H), 3.39 (m, 2H), 2.45 (t, 2H), 2.21 (s, 9H); MS (EI) for $C_{22}H_{24}N_4O_3$: 393 (MH$^+$).

Example 55

N-[2-(diethylamino)ethyl]-4-[6-(4-hydroxy-3-methylphenyl)-2-oxo-2,3-dihydropyrimidin-4-yl]benzamide (Compound 65)

N-[2-(diethylamino)ethyl]-4-[6-(4-hydroxy-3-methylphenyl)-2-oxo-2,3-dihydropyrimidin-4-yl]benzamide was synthesized in a manner similar to Example 53, wherein N,N-dimethyl-N'-ethylethylenediamine was substituted for 2-diethylaminoethylamine. Purification by preparative HPLC resulting in 4 mg (24% yield) of N-[2-(diethylamino)ethyl]-4-[6-(4-hydroxy-3-methylphenyl)-2-oxo-2,3-dihydropyrimidin-4-yl]benzamide. $^1$H NMR (400 MHz, d$_6$-DMSO): 8.59 (t, 1H), 8.24 (s, 2H), 8.22 (s, 1H), 7.97 (s, 2H), 7.90 (s, 1H), 7.87 (dd, 1H), 7.50 (s, 1H), 6.91 (d, 1H), 3.36 (m, 2H), 2.61-2.49 (m, 6H), 2.21 (s, 3H), 0.98 (t, 6H); MS (EI) for $C_{24}H_{28}N_4O_3$: 421 (MH$^+$).

Example 56

N-[3-(dimethylamino)propyl]-4-[6-(4-hydroxy-3-methylphenyl)-2-oxo-2,3-dihydropyrimidin-4-yl]-N-methylbenzamide (Compound 66)

N-[3-(dimethylamino)propyl]-4-[6-(4-hydroxy-3-methylphenyl)-2-oxo-2,3-dihydropyrimidin-4-yl]-N-methylbenzamide was synthesized in a manner similar to Example 53, wherein and N,N-dimethyl-N'-ethylethylenediamine was substituted for N,N-dimethyl-N'-ethylethylenediamine. Purification by preparative HPLC resulting in 3 mg (18% Yield) of N-[3-(dimethylamino)propyl]-4-[6-(4-hydroxy-3-methylphenyl)-2-oxo-2,3-dihydropyrimidin-4-yl]-N-methylbenzamide. $^1$H NMR (400 MHz, d$_6$-DMSO): 8.24 (s, 1H), 8.20 (d, 2H), 7.98 (m, 1H), 7.87 (dd, 1H), 7.52 (t, 2H), 7.47 (s, 1H), 6.91 (d, 1H), 3.23 (m, 2H), 2.98 (s, 3H), 2.91 (s, 3H), 2.33 (m, 1H), 2.19 (s, 3H), 2.09 (m, 1H), 1.98 (s, 3H), 1.77 (m, 1H), 1.64 (m, 1H); MS (EI) for $C_{24}H_{28}N_4O_3$: 421 (MH$^+$).

Example 57

3-[6-(4-hydroxy-3-methylphenyl)-2-oxo-2,3-dihydropyrimidin-4-yl]-N-[2-(methyloxy)ethyl]benzamide (Compound 57)

Scheme 4

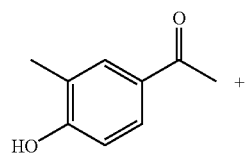

+

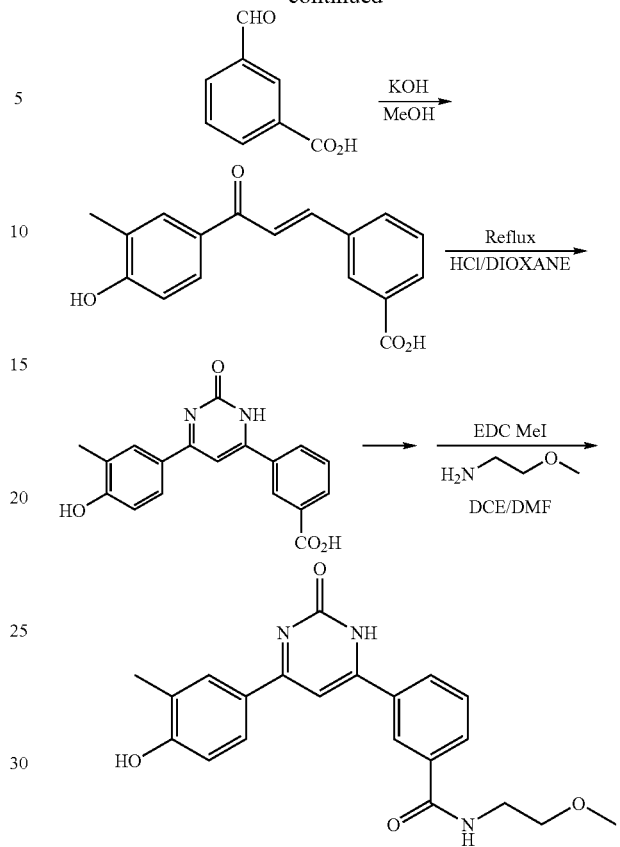

Step 1

(E)-3-(3-(4-hydroxy-3-methylphenyl)-3-oxoprop-1-enyl)benzoic acid

3-Formylbenzoic acid (15.0 g, 0.1 mol, Aldrich) and 4'-hydroxy-3'-methylacetophenone (15.0 g, 0.1 mol, Indofine) was dissolved in 150 mL of methanol and 50 mL of water. The solution was cooled with an ice-water bath, to which was added potassium hydroxide (28.0 g, 0.5 mol). The reaction mixture was stirred overnight. The resulted mixture was poured on to 600 mL of ice-water, acidified to pH=4-5 with 1 N HCl, filtered, washed with water (200 mL), methanol (100 mL) and dried in the air. 19 g (67%) of a solid was obtained as the desired (E)-3-(3-(3-(4-hydroxy-3-methylphenyl)-3-oxoprop-1-enyl)phenoxy)acetic acid. $^1$H NMR (400 MHz, DMSO-d$_6$): 13.18 (br, 1H), 10.39 (s, 1H), 8.38 (s, 1H), 8.15 (m, 1H), 7.95 (m, 4H), 7.75 (d, 1H), 7.60 (m, 1H), 6.95 (d, 1H), 2.20 (s, 3H). MS (EI) for $C_{17}H_{14}O_4$: 283 (MH$^+$).

Step 2

3-(6-(4-hydroxy-3-methylphenyl)-2-oxo-2,3-dihydropyrimidin-4-yl)benzoic acid (E)-3-(3-(4-hydroxy-3-methylphenyl)-3-oxoprop-1-enyl)benzoic acid (15.0 g, 53.0 mmol) and urea (16.0 g, 0.27 mol) was suspended in 200 mL of 4N HCl solution in dioxane, and the reaction mixture was heated to reflux overnight, then cooled to room temperature. The resulted mixture was concentrated in vacuo to remove dioxane. The residues were suspended in 150 mL of 2-propanol, filtered and washed with 50 mL of 2-propanol and then dried in the air. 8.1 g (48%) of the desired 3-(6-(4-hydroxy-3-methylphenyl)-2-oxo-2,3-dihydropyrimidin-4-yl)benzoic acid was obtained. $^1$H NMR (400 MHz, DMSO-$d_6$): 10.40 (s, 1H), 8.60 (s, 1H), 8.35 (m, 1H), 8.18 (m, 1H), 8.00 (s, 1H), 7.90 (m, 1H), 7.65 (m, 1H), 7.55 (m, 1H), 6.95 (m, 1H), 2.18 (s, 3H). MS (EI) for $C_{18}H_{14}N_2O_4$: 323 (MH$^+$).

Step 3

3-[6-(4-hydroxy-3-methylphenyl)-2-oxo-2,3-dihydropyrimidin-4-yl]-N-[2-(methyloxy)ethyl]benzamide To a solution of 3-(6-(4-hydroxy-3-methylphenyl)-2-oxo-2,3-dihydropyrimidin-4-yl)benzoic acid (16.9 mg, 48 umol) and 2-methoxyethanamine (3.0 mg, 40 umol) in dichloroethane (1.25 mL) and N,N-dimethylformamide (0.79 mL) was added 1-hydroxybenzotriazole (6.8 mg, 50 umol) followed by 1-[3-(dimethylamino)propyl]-3-ethylcarbodiimide methiodide (17.8 mg, 60 umol). The resultant mixture was stirred at room temperature for 15 hours. The reaction mixture was concentrated in vacuo. Purification of the residue by HPLC (reverse-phase, acetonitrile/water with 0.1% formic acid) followed by concentration in vacuo gave the title compound 3-[6-(4-hydroxy-3-methylphenyl)-2-oxo-2,3-dihydropyrimidin-4-yl]-N-[2-(methyloxy)ethyl]benzamide (5.4 mg, 36%).
$^1$H NMR (400 MHz, $d_6$-DMSO): 8.71 (t, 1H), 8.53 (s, 1H), 8.44 (s, 1H), 8.27 (d, 1H), 8.02 (d, 1H), 7.96 (s, 1H), 7.87 (dd, 1H), 7.64 (t, 1H), 7.46 (s, 1H), 6.93 (d, 1H), 3.52-3.44 (m, 4H), 3.29 (s, 3H), 2.20 (s, 3H). MS (EI) for $C_{21}H_{21}N_3O_4$: 380 (MH$^+$).

Example 58

3-(6-(4-hydroxy-3-methylphenyl)-2-oxo-2,3-dihydropyrimidin-4-yl)-N-(3-methoxypropyl)benzamide (Compound 71)

3-(6-(4-hydroxy-3-methylphenyl)-2-oxo-2,3-dihydropyrimidin-4-yl)-N-(3-methoxypropyl)benzamide was synthesized in a manner similar to Example 57, wherein 2-methoxyethanamine was substituted for 3-methoxypropan-1-amine. Purification by preparative HPLC resulted in 6.1 mg (39% Yield) of 3-(6-(4-hydroxy-3-methylphenyl)-oxo-2,3-dihydropyrimidin-4-yl)-N-(3-methoxypropyl)benzamide.
$^1$H NMR (400 MHz, $d_6$-DMSO): 8.65 (t, 1H), 8.52 (s, 1H), 8.47 (s, 1H), 8.27 (d, 1H), 8.01 (d, 1H), 7.96 (s, 1H), 7.87 (dd, 1H), 7.63 (t, 1H), 7.46 (s, 1H), 6.92 (d, 1H), 3.24 (s, 3H), 2.20 (s, 3H), 1.79 (t, 2H). MS (EI) for $C_{22}H_{23}N_3O_4$: 394 (MH$^+$).

Example 59

3-(6-(4-hydroxy-3-methylphenyl)-2-oxo-2,3-dihydropyrimidin-4-yl)-N-(2 isopropoxyethyl)benzamide (Compound 72)

3-(6-(4-hydroxy-3-methylphenyl)-2-oxo-2,3-dihydropyrimidin-4-yl)-N-(2-isopropoxyethyl)benzamide was synthesized in a manner similar to Example 57, wherein 2-methoxyethanamine was substituted for 2-isopropoxyethanamine. Purification by preparative HPLC resulted in 5.5 mg (34% yield) of 3-(6-(4-hydroxy-3-methylphenyl)-2-oxo-2,3-dihydropyrimidin-4-yl)-N-(2-isopropoxyethyl)benzamide.
$^1$H NMR (400 MHz, $d_6$-DMSO): 8.69 (t, 1H), 8.53 (s, 1H), 8.48 (s, 1H), 8.27 (d, 1H), 8.01 (d, 1H), 7.96 (s, 1H), 7.87 (dd, 1H), 7.63 (t, 1H), 7.46 (s, 1H), 6.93 (d, 1H), 3.63-3.56 (m, 1H), 3.54-3.49 (m, 2H), 2.20 (s, 3H), 1.10 (d, 6H). MS (EI) for $C_{23}H_{25}N_3O_4$: 408 (MH$^+$).

Example 60

N-(2-(dimethylamino)ethyl)-3-(6-(4-hydroxy-3-methylphenyl)-2-oxo-2,3-dihydropyrimidin-4-yl)benzamide Compound 73

N-(2-(dimethylamino)ethyl)-3-(6-(4-hydroxy-3-methylphenyl)-2-oxo-2,3-dihydropyrimidin-4-yl)benzamide was synthesized in a manner similar to Example 57, wherein 2-methoxyethanamine was substituted for N',N'-dimethylethane-1,2-diamine. Purification by preparative HPLC resulting in 3.1 mg (20% yield) of N-(2-(dimethylamino)ethyl)-3-(6-(4-hydroxy-3-methylphenyl)-2-oxo-2,3-dihydropyrimidin-4-yl)benzamide
$^1$H NMR (400 MHz, $d_6$-DMSO): 8.69 (t, 1H), 8.51 (s, 1H), 8.29-8.25 (m, 2H), 8.02 (d, 1H), 7.96 (s, 1H), 7.87 (dd, 1H), 7.63 (t, 1H), 7.46 (s, 1H), 6.93 (d, 1H), 2.45 (t, 2H), 2.21 (s, 9H). MS (EI) for $C_{22}H_{24}N_4O_3$: 393 (MH$^+$).

Example 61

N-(3-(dimethylaminopropyl)-3-(6-(4-hydroxy-3-methylphenyl-2-oxo-2,3-dihydropyrimidin-4-yl) benzamide (Compound 74)

N-(3-(dimethylamino)propyl)-3-(6-(4-hydroxy-3-methylphenyl)-2-oxo-2,3-dihydropyrimidin-4-yl)benzamide was synthesized in a manner similar to Example 57, wherein 2-methoxyethanamine was substituted for N',N'-dimethylpropane-1,3-diamine. Purification by preparative HPLC resulting in 2.5 mg (15% yield) of N-(3-(dimethylamino) propyl)-3-(6-(4-hydroxy-3-methylphenyl)-2-oxo-2,3-dihydropyrimidin-4-yl)benzamide.
$^1$H NMR (400 MHz, $d_6$-DMSO): 8.69 (t, 1H), 8.51 (s, 1H), 8.29-8.25 (m, 2H), 8.02 (d, 1H), 7.96 (s, 1H), 7.87 (dd, 1H), 7.63 (t, 1H), 7.46 (s, 1H), 6.93 (d, 1H), 2.33 (t, 2H), 2.21 (s, 3H), 2.19 (s, 6H), 1.70 (m, 2H). MS (EI) for $C_{23}H_{26}N_4O_3$: 407 (MH$^+$).

Example 62

N-(2-(dimethylamino)ethyl)-N-ethyl-3-(6-(4-hydroxy-3-methylphenyl)-2-oxo-2,3-dihydropyrimidin-4-yl)benzamide (Compound 75)

N-(2-(dimethylamino)ethyl)-N-ethyl-3-(6-(4-hydroxy-3-methylphenyl)-2-oxo-2,3-dihydropyrimidin-4-yl)benzamide was synthesized in a manner similar to Example 57, wherein 2-methoxyethanamine was substituted for N-ethyl-N',N'-dimethylethane-1,2-diamine. Purification by preparative HPLC resulted in 2.7 mg (16% yield) of N-(2-(dimethylamino)ethyl)-N-ethyl-3-(6-(4-hydroxy-3-methylphenyl)-2-oxo-2,3-dihydropyrimidin-4-yl)benzamide.
$^1$H NMR (400 MHz, $d_6$-DMSO): 8.28-8.18 (m, 2H), 8.12 (s, 1H), 7.97 (s, 1H), 7.88 (dd, 1H), 7.60 (t, 1H), 7.56-7.50 (m, 1H), 7.48 (s, 1H), 6.91 (d, 1H), 2.37 (m, 2H), 2.23 (s, 3H), 2.20 (s, 3H), 1.94 (s, 3H), 1.12 (brs, 3H). MS (EI) for $C_{24}H_{28}N_4O_3$: 421 (MH$^+$).

Example 63

N-(2-(dimethylaminoethyl)-3-(6-(4-hydroxy-3-methylphenyl)-2-oxo-2,3-dihydropyrimidin-4-yl)-N-methylbenzamide (Compound 76)

N-(2-(dimethylamino)ethyl)-3-(6-(4-hydroxy-3-methylphenyl)-2-oxo-2,3-dihydropyrimidin-4-yl)-N-methylbenzamide was synthesized in a manner similar to Example 57, wherein 2-methoxyethanamine was substituted for N-ethyl-N',N'-dimethylethane-1,2-diamine. Purification by preparative HPLC resulted in 3.0 mg (18% Yield) of N-(2-(dimethylamino)ethyl)-3-(6-(4-hydroxy-3-methylphenyl)-2-oxo-2,3-dihydropyrimidin-4-yl)-N-methylbenzamide.

$^1$H NMR (400 MHz, $d_6$-DMSO): 8.27 (s, 1H), 8.22 (d, 1H), 8.15 (d, 1H), 7.98 (s, 1H), 7.89 (dd, 1H), 7.62 (t, 1H), 7.55 (m, 1H), 7.49 (s, 1H), 6.92 (d, 1H), 3.42 (m, 2H), 2.98 (m, 3H), 2.38 (m, 2H), 2.24 (s, 3H), 2.20 (s, 3H), 1.95 (s, 3H). MS (EI) for $C_{23}H_{26}N_4O_3$: 407 (MH$^+$).

Example 64

N-(3-(dimethylaminopropyl)-3-(6-(4-hydroxy-3-methylphenyl)-2-oxo-2,3-dihydropyrimidin-4-yl-N-methylbenzamide (Compound 77)

N-(3-(dimethylamino)propyl)-3-(6-(4-hydroxy-3-methylphenyl)-2-oxo-2,3-dihydropyrimidin-4-yl)-N-methylbenzamide was synthesized in a manner similar to Example 57, wherein 2-methoxyethanamine was substituted for N,N,N'-trimethylpropane-1,3-diamine. Purification by preparative HPLC resulting in 2.6 mg (15% Yield) of N-(3-(dimethylamino)propyl)-3-(6-(4-hydroxy-3-methylphenyl)-2-oxo-2,3-dihydropyrimidin-4-yl)-N-methylbenzamide.

$^1$H NMR (400 MHz, $d_6$-DMSO): 8.27 (s, 1H), 8.22 (d, 1H), 8.15 (d, 1H), 7.98 (s, 1H), 7.89 (dd, 1H), 7.63-7.53 (m, 2H), 7.49 (s, 1H), 6.92 (d, 1H), 3.20 (m, 2H), 2.95 (m, 3H), 2.33 (m, 1H), 2.20 (s, 6H), 2.05 (m, 1H), 1.94 (s, 3H), 1.77 (m, 1H), 1.66 (m, 1H). MS (EI) for C24H28N4O3: 421 (MH$^+$).

Example 65

N-(2-aminoethyl)-3-(6-(4-hydroxy-3-methylphenyl)-2-oxo-2,3-dihydropyrimidin-4-yl)benzamide (Compound 56)

To a solution of 3-(6-(4-hydroxy-3-methylphenyl)-2-oxo-2,3-dihydropyrimidin-4-yl)benzoic acid obtained from step 2 of Example 57 (16.9 mg, 48 μmol) and tert-butyl 2-aminoethylcarbamate (6.4 mg, 40 μmol) in dichloroethane (1.25 mL) and N,N-dimethylformamide (0.79 mL) was added 1-hydroxybenzotriazole (6.8 mg, 50 μmol) followed by 1-[3-(Dimethylamino)propyl]-3-ethylcarbodiimide methiodide (17.8 mg, 60 μmol). The resultant mixture was stirred at room temperature for 15 hours. The reaction mixture was concentrated in vacuo, taken up in methanol (1 mL) and 4.0 N hydrochloric acid in dioxane (1 mL), and stirred at room temperature for 4 hours then concentrated. Purification of the residue by HPLC (reverse-phase, acetonitrile/water with 0.1% formic acid) followed by concentration in vacuo gave the title compound N-(2-aminoethyl)-3-(6-(4-hydroxy-3-methylphenyl)-2-oxo-2,3-dihydropyrimidin-4-yl)benzamide (3.4 mg, 23%).

$^1$H NMR (400 MHz, $d_6$-DMSO): 8.94 (t, 1H), 8.58 (s, 1H), 8.41 (s, 1H), 8.29 (d, 1H), 8.40 (d, 1H), 7.97 (s, 1H), 7.88 (dd, 1H), 7.65 (t, 1H), 7.50 (s, 1H), 6.93 (d, 1H), 2.89 (t, 2H), 2.20 (s, 3H). MS (EI) for $C_{20}H_{20}N_4O_3$: 365 (MH$^+$).

Example 66

N-(3-aminopropyl)-3-(6-(4-hydroxy-3-methylphenyl)-2-oxo-2,3-dihydropyrimidin-4-yl)benzamide (Compound 59)

N-(3-aminopropyl)-3-(6-(4-hydroxy-3-methylphenyl)-2-oxo-2,3-dihydropyrimidin-4-yl)benzamide was synthesized in a manner similar to Example 65, wherein tert-butyl 2-aminoethylcarbamate was substituted for tert-butyl 2-aminopropylcarbamate. Purification by preparative HPLC resulted in 4.2 mg (28% yield) of N-(3-aminopropyl)-3-(6-(4-hydroxy-3-methylphenyl)-2-oxo-2,3-dihydropyrimidin-4-yl)benzamide.

$^1$H NMR (400 MHz, $d_6$-DMSO): 8.86 (t, 1H), 8.55 (s, 1H), 8.45 (s, 1H), 8.29 (d, 1H), 8.02 (d, 1H), 7.96 (s, 1H), 7.87 (dd, 1H), 7.65 (t, 1H), 7.49 (s, 1H), 6.92 (d, 1H), 2.77 (t, 2H), 2.20 (s, 3H), 1.77 (t, 2H). MS (EI) for $C_{21}H_{22}N_4O_3$: 379 (MH$^+$).

Example 67

N-benzyl-2-(3-(6-(4-hydroxy-3-methylphenyl)-2-oxo-2,3-dihydropyrimidin-4-yl)phenoxy)acetamide (Compound 52)

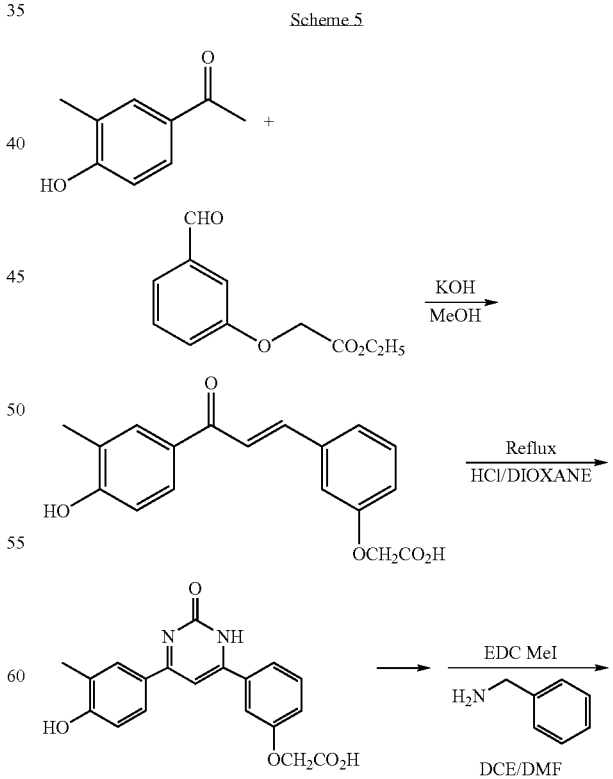

Scheme 5

-continued

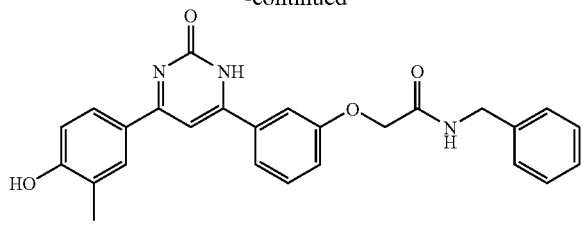

Step 1

(E)-2-(3-(3-(4-hydroxy-3-methylphenyl)-3-oxoprop-1-enyl)phenoxy)acetic acid

Ethyl 2-(3-formylphenoxy)acetate (20.8 g, 0.1 mol, Alfa Aesar) and 4'-hydroxy-3'-methylacetophenone (15.0 g, 0.1 mol, Indofine) were dissolved in 150 mL of methanol and 50 mL of water. The solution was cooled with an ice-water bath, to which was added potassium hydroxide (21.0 g, 0.375 mol). The reaction mixture was stirred overnight. The resulted mixture was poured on to 600 mL of ice-water, acidified to pH=4-5 with 1 N HCl, and extracted with ethyl acetate (4×200 mL). The combined organic layers were washed with water and brine (200 mL each), dried over anhydrous sodium sulfate, filtered and concentrated in vacuo. The obtained oil was dried under high-vacuum, 20 g (64%) of a solid was obtained as the desired (E)-2-(3-(3-(4-hydroxy-3-methylphenyl)-3-oxoprop-1-enyl)phenoxy)acetic acid.

$^1$H NMR (400 MHz, CDCl$_3$): 9.95 (s, 1H), 8.40 (br, 1H), 7.80 (s, 1H), 7.65 (m, 2H), 7.22-7.55 (m, 5H), 6.85 (d, 1H), 4.75 (s, 2H), 2.22 (s, 3H). MS (EI) for C$_{18}$H$_{16}$O$_5$: 313 (MH$^+$).

Step 2

({3-[6-(4-hydroxy-3-methylphenyl)-2-oxo-2,3-dihydropyrimidin-4-yl]phenyl}oxy)acetic acid (E)-2-(3-(3-(4-hydroxy-3-methylphenyl)-3-oxoprop-1-enyl)phenoxy)acetic acid (15.0 g, 48.0 mmol) and urea (14.4 g, 0.24 mol) were suspended in 200 mL of 4N HCl solution in dioxane, and the reaction mixture was heated to reflux overnight, then cooled to room temperature. The resulted mixture was concentrated in vacuo to remove dioxane. The residues were suspended in 150 mL of 2-propanol and heated in a 90° C. oil bath for 10 minutes, then cooled down to room temperature. The suspension was filtered and washed with 50 mL of 2-propanol and dried in the air. 9.2 g (54%) of the desired ({3-[6-(4-hydroxy-3-methylphenyl)-2-oxo-2,3-dihydropyrimidin-4-yl]phenyl}oxy)acetic acid were obtained. $^1$H NMR (400 MHz, DMSO-d$_6$): 10.39 (s, 1H), 8.00 (s, 1H), 7.90 (m, 1H), 7.75 (m, 1H), 7.65 (s, 1H), 7.40-7.55 (m, 2H), 7.16 (m, 1H), 6.95 (m, 1H), 4.80 (s, 2H), 2.20 (s, 3H). MS (EI) for C$_{19}$H$_{16}$N$_2$O$_5$: 353 (MH$^+$).

Step 3

N-benzyl-2-(3-(6-(4-hydroxy-3-methylphenyl)-2-oxo-2,3-dihydropyrimidin-4-yl)phenoxy)acetamide To a solution of ({3-[6-(4-hydroxy-3-methylphenyl)-2-oxo-2,3-dihydropyrimidin-4-yl]phenyl}oxy)acetic acid (16.9 mg, 48 µmol) and benzylamine (4.3 mg, 40 umol) in dichloroethane (1.25 mL) and N,N-dimethylformamide (0.79 mL) was added 1-hydroxybenzotriazole (6.8 mg, 50 µmol) followed by 1-[3-(Dimethylamino)propyl]-3-ethylcarbodiimide methiodide (17.8 mg, 60 µmol). The resultant mixture was stirred at room temperature for 15 hours. The reaction mixture was concentrated in vacuo. Purification of the residue by HPLC (reverse-phase, acetonitrile/water with 0.1% formic acid) followed by concentration in vacuo gave the title compound N-benzyl-2-(3-(6-(4-hydroxy-3-methylphenyl)-2-oxo-2,3-dihydropyrimidin-4-yl)phenoxy)acetamide (4.5 mg, 25%).

$^1$H NMR (400 MHz, d$_6$-DMSO): 8.74 (t, 1H), 7.95 (s, 1H), 7.86 (dd, 1H), 7.77-7.70 (m, 2H), 7.47 (t, 1H), 7.36 (s, 1H), 7.30-7.24 (m, 4H), 7.23-7.16 (m, 2H), 6.90 (d, 1H), 4.70 (s, 2H), 4.36 (d, 2H), 2.20 (s, 3H). MS (EI) for C$_{26}$H$_{23}$N$_3$O$_4$: 442 (MH$^+$).

Example 68

Scheme 6

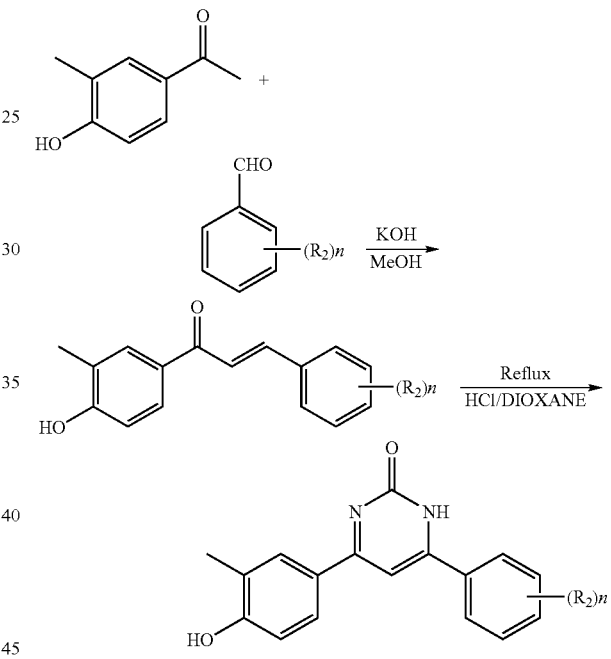

6-(2,3-dichlorophenyl)-4-(4-hydroxy-3-methylphenyl)pyrimidin-2(1H)-one (Compound 78)

To a mixture of 1-(4-hydroxy-3-methylphenyl)ethanone (0.7 g, 4.66 mmol) (ICC, Indofine Chemical Company Inc.) and NaOH (0.36 g, 9.1 mmol) in 10 mL of 200 proof EtOH was added 2,3-dichlorobenzaldehyde (0.8 g, 4.66 mmol) (ACROS). The reaction mixture was stirred at rt for 18 h. Upon completion by LC/MS, 5 mL of H$_2$O was added and the reaction mixture was acidified with conc. HCl to pH 5-6. The resulting precipitate was filtered, washed with water and dried to yield (E)-3-(2,3-dichlorophenyl)-1-(4-hydroxy-3-methylphenyl)prop-2-en-1-one, (0.45 g, 31%). MS (EI) for C$_{16}$H$_{12}$C$_2$O$_2$, 308.3 (MH$_+$).

A mixture of (E)-3-(2,3-dichlorophenyl)-1-(4-hydroxy-3-methylphenyl)prop-2-en-1-one (123 mg, 0.4 mmol) and urea (28 mg, 2.0 mmol,) (SIGMA-ALDRICH) in 4N HCl/dioxane (5 mL) was heated to 120° C. in a sealed vessel overnight. The reaction was complete as determined by LCMS, and the solution was cooled to room temperature. The crude reaction mixture was purified by reverse-phase HPLC (acetonitrile/10 mM aqueous ammonium acetate) to yield the desired product (35 mg, 25%) $^1$H NMR (400 MHz, d6-DMSO): 7.93 (s, 1H), 7.80-7.82 (dd, 1H), 7.49-7.58 (m, 2H), 7.09 (s, 1H), 6.88 (d, 1H), 2.18 (s, 3H). MS (EI) for $C_{17}H_{12}Cl_2N_2O_2$: 348.5 (MH+).

Example 69

4-(4-hydroxy-3-methylphenyl)-6-[2-(1-methylethyl) phenyl]pyrimidin-2(1H-one (Compound 50)

Using the same or analogous synthetic techniques described in Example 68, 4-(4-hydroxy-3-methylphenyl)-6-[2-(1-methylethyl)phenyl]pyrimidin-2(1H)-one was prepared by replacing 2,3-dichlorobenzaldehyde with commercially available 2-isopropylbenzaldehyde.

$^1$H NMR (400 MHz, d6-DMSO): 7.94 (s, 1H), 7.84 (d, 1H), 7.49 (m, 2H), 7.32 (m, 2H), 6.87 (m, 2H), 2.17 (s, 3H), 1.20 (s, 3H), 1.18 (s, 3H). MS (EI) for $C_{20}H_{20}N_2O_2$: 321.2 (MH$^+$).

Example 70

6-[2,4-bis(methyloxy)phenyl]-4-(4-hydroxy-3-methylphenyl)pyrimidin-2(1H)-one (Compound 53)

Using the same or analogous synthetic techniques described in Example 68, 6-[2,4-bis(methyloxy)phenyl]-4-(4-hydroxy-3-methylphenyl)pyrimidin-2(1H)-one was prepared by replacing 2,3-dichlorobenzaldehyde with commercially available 2,4-dimethoxybenzaldehyde.

$^1$H NMR (400 MHz, d$_6$-DMSO): 7.88 (s, 1H), 7.79 (dd, 1H), 7.61 (d, 1H), 7.04 (s, 1H), 6.88 (d, 1H), 6.70 (d, 1H), 6.67 (dd, 1H), 3.86 (s, 3H), 3.85 (s, 3H), 2.18 (s, 3H). MS (EI) for $C_{19}H_{18}N_2O_4$: 339 (MH$^+$).

Example 71

6-[2,3-bis(methyloxy)phenyl]-4-(4-hydroxy-3-methylphenyl)pyrimidin-2(1H)-one (Compound 54)

Using the same or analogous synthetic techniques described in Example 68, 6-[2,3-bis(methyloxy)phenyl]-4-(4-hydroxy-3-methylphenyl)pyrimidin-2(1H)-one was prepared by replacing 2,3-dichlorobenzaldehyde with commercially available 2,3-dimethoxybenzaldehyde.

$^1$H NMR (400 MHz, d6-DMSO): 7.88 (s, 1H), 7379 (d, 1H), 7.61 (d, 1H), 7.03 (s, 1H), 6.88 (d, 1H), 6.72 (d, 1H), 6.66-6.71 (dd, 1H), 3.87 (s, 3H), 3.85 (s, 3H), 2.19 (s, 3H). MS (EI) for $C_{19}H_{18}N_2O_4$: 339.4 (MH$^+$).

Example 72

4-(4-hydroxy-3-methylphenyl)-6-(2-iodophenyl) pyrimidin-2(1H)-one (Compound 55)

Using the same or analogous synthetic techniques described in Example 68, 4-(4-hydroxy-3-methylphenyl)-6-(2-iodophenyl)pyrimidin-2(1H)-one was prepared by replacing 2,3-dichlorobenzaldehyde with commercially available 2-iodobenzaldehyde.

$^1$H NMR (400 MHz, d6-DMSO): 8.00 (d, 1H), 7.94 (s, 1H), 7.84 (d, 1H), 7.52 (m, 2H), 7.26 (t, 1H), 6.93 (s, 1H), 6.88 (d, 1H), 2.18 (s, 3H). MS (EI) for $C_{17}H_{13}IN_2O_2$: 405.0 (MH$^+$).

Example 73

6-(2,5-dichlorophenyl)-4-(4-hydroxy-3-methylphenyl)pyrimidin-2(1H)-one (Compound 58)

Using the same or analogous synthetic techniques described in Example 68, 6-(2,5-dichlorophenyl)-4-(4-hydroxy-3-methylphenyl)pyrimidin-2(1H)-one was prepared by replacing 2,3-dichlorobenzaldehyde with commercially available 2,5-dichlorobenzaldehyde.

$^1$H NMR (400 MHz, d6-DMSO): 7.93 (s, 1H), 7.83 (s, 1H), 7.74 (s, 1H), 7.76 (m, 2H), 7.09 (s, 1H), 6.88 (d, 1H), 2.18 (s, 3H). MS (EI) for $C_{16}H_{12}Cl_2O_2$: 307.0 (MH$^+$).

Example 74

6-[3-bromo-4-(methyloxy)phenyl]-4-(4-hydroxy-3-methylphenyl)pyrimidin-2(1H)-one (Compound 60)

Using the same or analogous synthetic techniques described in Example 68, 6-[3-bromo-4-(methyloxy)phenyl]-4-(4-hydroxy-3-methylphenyl)pyrimidin-2(1H)-one was prepared by replacing 2,3-dichlorobenzaldehyde with commercially available 3-bromo-4-methoxybenzaldehyde. 6-[3,4-bis(methyloxy)phenyl]-4-(4-hydroxy-3-methylphenyl)pyrimidin-2(1H)-one:

$^1$H NMR (400 MHz, d6-DMSO): 10.21 (s, 1H), 8.43 (s, 1H), 8.20 (d, 1H), 7.95 (s, 1H), 7.87 (d, 1H), 7.25 (d, 1H), 6.89 (d, 1H), 3.94 (s, 3H), 2.19 (s, 3H). MS (EI) for $C_{18}H_{15}BrN_2O_3$: 387.0 (MH$^+$).

Example 75

6-[3,4-bis(methyloxy)phenyl]-4-(4-hydroxy-3-methylphenyl)pyrimidin-2(1H)-one (Compound 61)

Using the same or analogous synthetic techniques described in Example 68, 6-[3,4-bis(methyloxy)phenyl]-4-(4-hydroxy-3-methylphenyl)pyrimidin-2(1H)-one was prepared by replacing 2,3-dichlorobenzaldehyde with commercially available 3,4-dimethoxybenzaldehyde.

$^1$H NMR (400 MHz, d6-DMSO): 7.95 (s, 1H), 7.86 (d, 1H), 7.77 (d, 1H), 7.68 (s, 1H), 7.33 (s, 1H), 7.10 (d, 1H), 6.90 (d, 1H), 3.88 (s, 3H), 3.85 (s, 3H), 2.21 (s, 3H). MS (EI) for $C_{19}H_{18}N_2O_4$: 339.1 (MH$^+$).

Example 76

6-(3,4-dichlorophenyl)-4-(4-hydroxy-3-methylphenyl)pyrimidin-2(1H)-one (Compound 62)

Using the same or analogous synthetic techniques described in Example 68, 6-(3,4-dichlorophenyl)-4-(4-hydroxy-3-methylphenyl)pyrimidin-2(1H)-one was prepared by replacing 2,3-dichlorobenzaldehyde with commercially available 3,4-dichlorobenzaldehyde. 6-(3,4-dichlorophenyl)-4-(4-hydroxy-3-methylphenyl)pyrimidin-2(1H)-one:

$^1$H NMR (400 MHz, d6-DMSO): 11.90 (s, 1H), 10.15 (s, 1H), 8.47 (s, 1H), 8.19 (s, 1H), 7.88 (m, 2H), 6.90 (d, 1H), 2.21 (s, 3H). MS (EI) for $C_{17}H_{12}Cl_2N_2O_2$: 347.0 (MH$^+$).

Biological Assay:

For a biochemical measurement of CK2 inhibitory activity, compounds of the invention were screened in a luciferase-coupled chemiluminescence assay that detects consumption of ATP by the CK2 enzyme. The assay was performed using two different constructs of the enzyme, CK2 holoenzyme and CK2 alpha subunit. The assay buffer is composed of 20 mM Tris, pH 7.5, 10 mM $MgCl_2$, 0.03% Triton-X-1000, 1 mM DTT and 0.1 mM $NaVO_3$.

For the CK2 alpha subunit assay, the assay is performed as follows: 0.5 µl of test compound is added to a microtiter plate, followed by the addition of 10 µl substrate containing CK2 peptide (RRRDDDSDDD) and ATP and 10 µl of alpha subunit of the CK2 enzyme. The concentration of CK2 peptide is 9 µM, ATP is 2 µM and CK2-alpha subunit is 10 nM.

For the CK2 holoenzyme assay, the assay is performed as follows: 0.5 µl of test compound is added to a microtiter plate, followed by the addition of 10 µl substrate containing casein and ATP and 10 µl of CK2 holoenzyme. The concentration of casein is 2 µM, ATP is 2 µM and CK2 holoenzyme is 6 nM.

For both assays, the mixture is shaken briefly and incubated for 120 min at room temperature. At the end of the incubation, 10 µl of Kinase Glo (luciferase) is added and the signal is detected in a luminescence reader (Victor, Perkin Elmer).

The compounds in Table 1 have been tested for their CK2 inhibitory activity ($IC_{50}$ values), and these compounds have CK2 $IC_{50}$ values of less than 5000 nM. A preferred group of compounds of Table 1 have CK2 $IC_{50}$ values of less than 4000 nm. Another preferred group of compounds of Table 1 have CK2 $IC_{50}$ values of less than 510 nm. Another preferred group of compounds of Table 1 have CK2 $IC_{50}$ values of less than 500 nm. Another preferred group of compounds of Table 1 have CK2 $IC_{50}$ values of less than 200 nm. Another preferred group of compounds of Table 1 have CK2 $IC_{50}$ values of less than 100 nm.

Compounds of the invention may also be active against PIM 1 and/or PIM 2 kinase activity. Accordingly, compounds of the invention can also be useful for treating proliferative disorders associated with PIM 1 and/or PIM 2 kinase activity.

PIM Assay Protocol

PIM kinase activity can be measured by monitoring peptide substrate dependent hydrolysis of ATP via quantitation of remaining ATP with luciferase based chemiluminescence. For compound evaluation, 0.5 ul compound dissolved in DMSO is added to 10 ul of PIM-1 and/or PIM-3 dissolved in assay buffer (20 mM HEPES pH 7.5, 10 mM MgCl2, 0.03% Triton and 1 mM DTT). After preincubation for about 30 minutes at about room temperature, the reaction is initiated by addition of 10 ul of ATP and substrate peptide AKRRRLSA in assay buffer. The reaction mixture is incubated for about 120 min at room temperature, and the reaction progress can be quantitated by addition of 10 ul Kinase-Glo (Promega) and measuring chemiluminescence in a Victor reader (Perkin Elmer). A reaction in which compound is omitted is used to determine maximum reaction progress. Omission of compound and enzyme from the reaction can be used to determine zero reaction progress.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of Formula I:

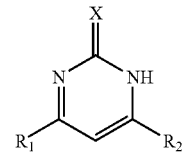

or a pharmaceutically acceptable salt thereof, wherein:

X is O;

$R_1$ is phenyl, —NH-phenyl, pyrrol, pyridinyl, dihydropyridinyl or indole, wherein each phenyl, —NH-phenyl, pyrrol, pyridinyl, dihydropyridinyl, and indole are optionally substituted with one or more groups independently selected from halo, —OH, —($C_1$-$C_6$)alkyl, —$CF_3$, —O($C_1$-$C_6$)alkyl-phenyl, —N-phenyl, —($C_1$-$C_6$)alkyl-phenyl, —O($C_1$-$C_6$)alkyl, -(5-10 membered) heteroaryl, —($C_1$-$C_6$)alkoxy, —($C_1$-$C_6$)alkoxy($C_1$-$C_6$) alkoxy, —O($C_1$-$C_6$)alkyl-N[($C_1$-$C_6$)alkyl]$_2$, —C(O)NH ($C_1$-$C_6$)alkyl, —C(O)NH($C_1$-$C_6$)alkyl-N[($C_1$-$C_6$) alkyl]$_2$, —C(O)NH($C_1$-$C_6$)alkyl$NH_2$, —O—($C_1$-$C_6$) alkyl-C(O)NH($C_1$-$C_6$)alkyl-phenyl, —C(O)NH($C_1$-$C_6$) alkyl-O—($C_1$-$C_6$)alkyl, C(O)—N[($C_1$-$C_6$)alkyl]$_2$—N [($C_1$-$C_6$)alkyl]$_2$ and oxo;

$R_2$ is phenyl substituted in the ortho or meta positions with one or more groups independently selected from —O($C_1$-$C_6$)alkyl-phenyl, —($C_1$-$C_6$)alkyl-phenyl, —O($C_1$-$C_6$)alkyl, -(5-10 membered)heteroaryl, —$NH_2$, —($C_1$-$C_6$)alkoxy, —($C_1$-$C_6$)alkoxy($C_1$-$C_6$)alkoxy, —O($C_1$-$C_6$)alkyl-N[($C_1$-$C_6$)alkyl]$_2$, —C(O)NH($C_1$-$C_6$)alkyl, —C(O)NH($C_1$-$C_6$)alkyl-N[($C_1$-$C_6$)alkyl]$_2$, —C(O)NH($C_1$-$C_6$)alkyl$NH_2$, —O—($C_1$-$C_6$)alkyl-C (O)NH($C_1$-$C_6$)alkyl-phenyl, —C(O)NH($C_1$-$C_6$)alkyl-O—($C_1$-$C_6$)alkyl, and —C(O)—N[$C_1$-$C_6$)alkyl]$_2$-N [($C_1$-$C_6$)alkyl]$_2$; or $R_2$ is phenyl substituted with both Br and —$CH_3$ or both Br and —$OCH_3$;

with the provisos that when one of $R_1$ phenyl, then $R_2$ is not or one of $R_1$ or $R_2$ is

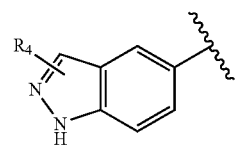

and the remaining $R_1$ or $R_2$ is

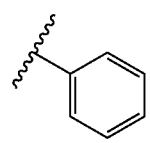

wherein $R_4$ is selected from hydrogen, halo, —OH, —$NH_2$, and —($C_1$-$C_6$)alkyl;

or one of $R_1$ or $R_2$ is an unsubstituted phenyl, and the remaining $R_1$ or $R_2$ is phenyl substituted with one —$NH_2$ and optionally one —($C_1$-$C_6$)alkyl.

2. The compound according to claim 1, wherein
R₁ is phenyl substituted with one or more groups independently selected from Cl, I, —OH, —(C₁-C₆)alkyl, —CF₃, —O(C₁-C₆)alkyl-phenyl, —(C₁-C₆)alkyl-phenyl, —O(C₁-C₆)alkyl, -(5-10 membered)heteroaryl, —(C₁-C₆)alkoxy, —(C₁-C₆)alkoxy(C₁-C₆)alkoxy, —O(C₁-C₆)alkyl]₂, —C(O)NH(C₁-C₆)alkyl, —C(O)NH(C₁-C₆)alkyl-N[(C₁-C₆)alkyl]₂, —C(O)NH(C₁-C₆)alkyl-NH₂, —O—(C₁-C₆)alkyl-C(O)NH(C₁-C₆)alkyl-phenyl, —C(O)NH(C₁-C₆)alkyl-O—(C₁-C₆)alkyl, and —C(O)—N[(C₁C₆)alkyl]₂—N[C₁-C₆)alkyl]₂.

3. The compound according to claim 1, wherein R₁ is phenyl substituted with one or more groups independently selected from —OH and —(C₁-C₆)alkyl.

4. The compound according to claim 1, wherein R₁ is

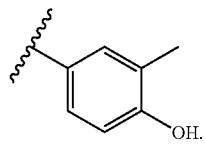

5. The compound according to claim 1, wherein
R₂ is phenyl substituted in the ortho or meta positions with one or more groups independently selected from —O(C₁-C₃)alkyl-OH, —O(C₆)alkyl, —(C₁-C₃)alkoxy(C—C₃)alkoxy, —O(C₁C₃)alkyl-(5-6 membered)heteroaryl, —O(C₁-C₃)alkyl-N[(C₁-C₃)alkyl]₂, —C(O)NH(C₁-C₃)alkyl, —C(O)NH(C₁-C₃)alkyl-N[(C₁-C₃)alkyl]₂, —C(O)—N[(C₁—C3)alkyl]₂-N[(C₁-C₃)alkyl]₂, —C(O)NH(C₁-C₃)alkyl-O—(C₁-C₃)alkyl, and —C(O)NH(C₁-C₃)alkyl-N[(C₁-C₆)alkyl]₂.

6. A compound of Formula I:

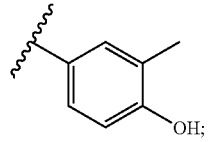

or a pharmaceutically acceptable salt thereof, wherein:
X is O;
R₁ is phenyl substituted with one or more groups independently selected from Cl, I, —OH, —(C₁-C₆)alkyl, —CF₃, —O(C₁-C₆)alkyl-phenyl, —(C₁-C₆)alkyl-phenyl, —O(C₁-C₆)alkyl, -(5-10 membered)heteroaryl, —(C₁-C₆)alkoxy, —(C₁-C₆)alkoxy(C₁-C₆)alkoxy, —O(C₁C₆)alkyl-N[(C₁-C₆)alkyl]₂, —C(O)NH(C₁-C₆)alkyl, —C(O)NH(C₁-C₆)alkyl-N[(C₁-C₆)alkyl]₂, —C(O)NH(C₁-C₆)alkylNH₂, —O—(C₁-C₆)alkyl-C(O)NH(C₁-C₆)alkyl-phenyl, —C(O)NH(C₁-C₆)alkyl-O—(C₁-C₆)alkyl, and —C(O)—N[(C₁-C₆)alkyl]₂—N[(C₁-C₆)alkyl]₂,
R₂ is phenyl, substituted with one or more groups independently selected from —O(C₁-C₆)alkylphenyl, —(C₁-C₆)alkyl-phenyl, —O(C₆)alkyl, -(5-10 membered)heteroaryl, —NH₂, —(C₁-C₆)alkoxy, —(C₁-C₆)alkoxy(C₁-C₆)alkoxy, —O(C₁-C₆)alkyl-N[(C₁-C₆)alkyl]₂—C(O)NH(C₁-C₆)alkyl, —C(O)NH(C₁-C₆)alkyl-N[(C₁-C₆)alkyl]₂, —C(O)NH(C₁-C₆)alkyl-NH₂, —O—(C₁-C₆)alkyl-C(O)NH(C₁-C₆)alkyl-phenyl, —C(O)NH(C₁-C₆)alkyl-O—(C₁-C₆)alkyl, and —C(O)—N[(C₁-C₆)alkyl]₂—N[(C₁-C₆)alkyl]₂ or
R₂ is phenyl substituted with both Br and —CH₃ or both Br and —OCH₃,
or R₁ is an unsubstituted phenyl; and R₂ is phenyl substituted with one —NH₂ and optionally one —(C₁-C₆)alkyl.

7. The compound according to claim 1, wherein
X is O;
R₁ is phenyl substituted with one or more groups independently selected from —OH and —(C₁-C₆)alkyl; and
R₂ is phenyl substituted with one or more groups independently selected from —O(C₁-C₆)alkylOH, —O(C₁-C₆)alkyl, —(C₁-C₆)alkoxy(C₁-C₆)alkoxy, —O(C₆)alkyl-(5-10 membered)heteroaryl, —O(C₆)alkyl-N[(C₁-C₆)alkyl]₂, —C(O)NH(C₁-C₆)alkyl, —C(O)NH(C₁-C₆)alkyl-N[(C₁-C₆)alkyl]₂, —C(O)—N[(C₁-C₆)alkyl]₂—N[(C₁-C₆)alkyl]₂, —C(O)NH(C₁-C₆)alkyl-O—(C₁-C₆)alkyl, and —C(O)NH(C₁-C₆)alkyl-N[(C₁-C₆)alkyl]₂; or
R₂ is phenyl substituted with both Br and —CH₃ or both Br and —OCH3.

8. The compound according to claim 1, wherein
X is O;
R₁ is

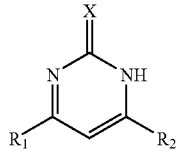

and
R₂ is phenyl substituted with one or more groups independently selected from —O(C₁-C₃)alkylOH, —O(C₁-C₆)alkyl, —(C₁-C₃)alkoxy(C₁-C₃)alkoxy, —O(C₁—C3)alkyl-(5-6 membered)heteroaryl, —O(C₁-C₃)alkyl-N[(C₁-C₃)alkyl]₂, —C(O)NH(C₁—C3)alkyl, —C(O)NH(C₁-C₃)alkyl-N[(C₁-C₃)alkyl]₂, —C(O)—N[(C₁-C₃)alkyl]₂-N[(C₁-C₃)alkyl]₂, —C(O)NH(C₁-C₃)alkyl-O—(C₁-C₃)alkyl, and —C(O)NH(C₁-C₃)alkyl-N[(C₁-C₆)alkyl]₂.

9. The compound according to claim 1, wherein one of R₁ or R₂ is phenyl substituted with —O—(CH₂)₂—O—CH₃.

10. A compound selected from:
6-phenyl-4-[4-(trifluoromethyl)phenyl]pyrimidin-2(1H)-one;
6-(4-bromophenyl)-4-(4-hydroxy-3-methylphenyl)pyrimidin-2(1H)-one;
4-(3-methylphenyl)-6-phenylpyrimidin-2(1H)-one;
4-(1-methyl-1H-pyrrol-2-yl)-6-phenylpyrimidin-2(1H)-one;
4-(4-fluorophenyl)-6-phenylpyrimidin-2(1H)-one;
4-(4-fluoro-3-methylphenyl)-6-phenylpyrimidin-2(1H)-one;
4-(3-hydroxyphenyl)-6-phenylpyrimidin-2(1H)-one;
6[2-(methyloxy)phenyl]-4-{3-methyl-4-[(phenylmethyl)oxy]phenyl}pyrimidin-2(1H)-one;
6[3-(methyloxy)phenyl]-4-{3-methyl-4-[(phenylmethy)oxy]phenyl}pyrimidin-2(1H)-one;
4-(4-hydroxy-3-methylphenyl)-6[2-(methyloxy)phenyl]pyrimidin-2(1H)-one;
4-(4-hydroxy-3-methylphenyl)-6[3-(methyloxy)phenyl]pyrimidin-2(1H)-one;

4-(4-hydroxy-3-methylphenyl)-6[4-(methyloxy)phenyl] pyrimidin-2(1H)-one;
4-(4-hydroxy-3-methylphenyl)-6[4-(trifluoromethyl)phenyl]pyrimidin-2(1H)-one;
4-(4-hydroxy-3-methylphenyl)-6-(4-methylphenyl)pyrimidin-2(1H)-one;
4-(4-hydroxy-3-methylphenyl)-6-(4-hydroxyphenyl)pyrimidin-2(1H)-one;
4-(3-aminophenyl)-6-phenylpyrimidin-2(1H)-one;
6-[2-bromo-5-(methyloxy)phenyl]-4-(4-hydroxy-3-methylphenyl)pyrimidin-2(1H)-one;
6-(4-chlorophenyl)-4-(4-hydroxy-3-methylphenyl)pyrimidin-2(1H)-one;
4-(4-hydroxy-3-methylphenyl)-6-(phenylamino)pyrimidin-2(1H)-one;
6-(2-chlorophenyl)-4-(4-hydroxy-3-methylphenyl)pyrimidin-2(1H)-one;
4[4-hydroxy-3-(methyloxy)phenyl]-6-phenylpyrimidin-2(1H)-one;
4-(3-chloro-4-hydroxyphenyl)-6-phenylpyrimidin-2(1H)-one;
4-(3-ethyl-4-hydroxyphenyl)-6-phenylpyrimidin-2(1H)-one;
6-[6-oxo-1-(phenylmethyl)-1,6-dihydropyridin-3-yl]-4-phenylpyrimidin-2(1H)-one;
6-[4-hydroxy-3-(1-methylethyl)phenyl]-4-phenylpyrimidin-2(1H)-one;
4-(3-bromophenyl)-6-(4-hydroxy-3-methylphenyl)pyrimidin-2(1H)-one;
4-(2-bromophenyl)-6-(4-hydroxy-3-methylphenyl)pyrimidin-2(1H)-one;
4-(4-amino-3-methylphenyl)-6-phenylpyrimidin-2(1H)-one;
4-(4-fluoro-3-methylphenyl)-6-[2-(methyloxy)phenyl] pyrimidin-2(1H)-one;
4-(4-hydroxy-3-methylphenyl)-6-(2-{[2-(methyloxy)ethyl]oxy]phenyl)pyrimidin-2(1H)-one;
4-(4-hydroxy-3-methylphenyl)-6-(3-{[2-(methyloxy)ethyl]oxy}phenyl)pyrimidin-2(1H)-one;
4-(4-hydroxy-3-methylphenyl)-6-(4-{[2-(methyloxy)ethyl]oxy}phenyl)pyrimidin-2(1H)-one;
6-(2-{[2-(diethylamino)ethyl]oxy}phenyl)-4-(4-hydroxy-3-methylphenyl)pyrimidin-2(1H)-one;
4-(1H-indazol-5-yl)-6-phenylpyrimidin-2(1H)-one;
6-(3-{[2-(diethylamino)ethyl]oxy}phenyl)-4-(4-hydroxy-3-methylphenyl)pyrimidin-2(1H)-one;
4-(4-hydroxy-3-methylphenyl)-6-{3-[(2-morpholin-4-yl-ethyl)oxy]phenyl]pyrimidin-2(1H)-one;
N-[3-(diethylamino)propyl]-3[6-(4-hydroxy-3-methylphenyl)-2-oxo-2,3-dihydropyrimidin-4-yl]benzamide;
N[2-(diethylamino)ethyl]-3[6-(4-hydroxy-3-methylphenyl)-2-oxo-2,3-dihydropyrimidin-4-yl]benzamide;
6-(2,5-bis{[2-(methyloxy)ethyl]oxy]phenyl)-4-(4-hydroxy-3-methylphenyl)pyrimidin-2(1H)-one;
6-(2,4-bis{[2-(methyloxy)ethyl]oxy]phenyl)-4-(4-hydroxy-3-methylphenyl)pyrimidin-2(1H)-one;
4-(4-hydroxy-3-methylphenyl)-6[2-(propyloxy)phenyl] pyrimidin-2(1H)-one;
6-[2-(butyloxy)phenyl]-4-(4-hydroxy-3-methylphenyl) pyrimidin-2(1H)-one;
4-(4-hydroxy-3-methylphenyl)-6-{2[(3-hydroxypropyl) oxy]phenyl]pyrimidin-2(1H)-one;
4-(4-hydroxy-3-methylphenyl)-6-(2-{[3-(methyloxy)propyl]oxy]phenyl)pyrimidin-2(1H)-one;
4-(3-bromo-4-fluorophenyl)-6-phenylpyrimidin-2(1H)-one;
4-(3-amino-1H-indazol-5-yl)-6-phenylpyrimidin-2(1H)-one;
4-(4-hydroxy-3-methylphenyl)-6-{2-[(2-methylpropyl) oxy]phenyl}pyrimidin-2(1H)-one;
4-(4-hydroxy-3-methylphenyl)-6-{2-[(3-methylbutyl) oxy]phenyl]pyrimidin-2(1H)-one;
4-(4-hydroxy-3-methylphenyl)-6-[2-(1-methylethyl)phenyl]pyrimidin-2(1H)-one;
4-(4-hydroxyphenyl)-6-{2-[(3-methylbutyl)oxy]phenyl] pyrimidin-2(1H)-one;
2-({3-[6-(4-hydroxy-3-methylphenyl)-2-oxo-2,3-dihydropyrimidin-4-yl]phenyl}oxy)-N-(phenylmethyl)acetamide;
6-[2,4-bis(methyloxy)phenyl]-4-(4-hydroxy-3-methylphenyl)pyrimidin-2(1H)-one;
6-[2,3-bis(methyloxy)phenyl]-4-(4-hydroxy-3-methylphenyl)pyrimidin-2(1H)-one;
4-(4-hydroxy-3-methylphenyl)-6-(2-iodophenyl)pyrimidin-2(1H)-one;
N-(2-aminoethyl)-3-[6-(4-hydroxy-3-methylphenyl)-2-oxo-2,3-dihydropyrimidin-4-yl]benzamide;
6-[2-bromo-5-(methyloxy)phenyl]-4-(4-hydroxy-3-methylphenyl)pyrimidin-2(1H)-one;
6-[2,5-dichlorophenyl)-4-(4-hydroxy-3-methylphenyl) pyrimidin-2(1H)-one;
N-(3-aminopropyl)-3-[6-(4-hydroxy-3-methylphenyl)-2-oxo-2,3-dihydropyrimidin-4-yl]benzamide;
6-[3-bromo-4-(methyloxy)phenyl]-4-(4-hydroxy-3-methylphenyl)pyrimidin-2(1H)-one;
6-[3,4-bis(methyloxy)phenyl]-4-(4-hydroxy-3-methylphenyl)pyrimidin-2(1H)-one;
6-(3,4-dichlorophenyl)-4-(4-hydroxy-3-methylphenyl) pyrimidin-2(1H)-one;
N-[2-(dimethylamino)ethyl]-N-ethyl-4-[6-(4-hydroxy-3-methylphenyl)-2-oxo-2,3-dihydropyrimidin-4-yl]benzamide;
N-[2-(dimethylamino)ethyl]-4-[6-(4-hydroxy-3-methylphenyl)-2-oxo-2,3-dihydropyrimidin-4-yl]benzamide;
N-[2-(diethylamino)ethyl]-4-[6-(4-hydroxy-3-methylphenyl)-2-oxo-2,3-dihydropyrimidin-4-yl]benzamide;
N-[3-(dimethylamino)propyl]-4-[6-(4-hydroxy-3-methylphenyl)-2-oxo-2,3-dihydropyrimidin-4-yl]-N-methylbenzamide;
6-(4-bromo-2-methylphenyl)-4-(4-hydroxy-3-methylphenyl)pyrimidin-2(1H)-one;
4-(4-hydroxy-3,5-dimethylphenyl)-6-12-[(3-methylbutyl)oxy]phenyl]pyrimidin-2(1H)-one;
N-[2-(diethylamino)ethyl]-3-[6-(4-hydroxy-3-methylphenyl)-2-oxo-2,3-dihydropyrimidin-4-yl]benzamide;
3-[6-(4-hydroxy-3-methylphenyl)-2-oxo-2,3-dihydropyrimidin-4-yl]-N-[2-(methyloxy)ethyl]benzamide;
3-[6-(4-hydroxy-3-methylphenyl)-2-oxo-2,3-dihydropyrimidin-4-yl]-N-[3-(methyloxy)propyl]benzamide;
3-[6-(4-hydroxy-3-methylphenyl)-2-oxo-2,3-dihydropyrimidin-4-yl]-N-{2-[(1-methylethyl)oxy] ethyl}benzamide;
N-[2-(dimethylamino)ethyl]-3-[6-(4-hydroxy-3-methylphenyl)-2-oxo-2,3-dihydropyrimidin-4-yl]benzamide;
N-[3-(dimethylamino)propyl]-3-[6-(4-hydroxy-3-methylphenyl)-2-oxo-2,3-dihydropyrimidin-4-yl]benzamide;

N-[2-(dimethylamino)ethyl]-N-ethyl-3-[6-(4-hydroxy-3-methylphenyl)-2-oxo-2,3-dihydropyrimidin-4-yl]benzamide;

N-[2-(dimethylamino)ethyl]-3-[6-(4-hydroxy-3-methylphenyl)-2-oxo-2,3-dihydropyrimidin-4-yl]-N-methylbenzamide;

N-[3-(dimethylamino)propyl]-3-[6-(4-hydroxy-3-methylphenyl)-2-oxo-2,3-dihydropyrimidin-4-yl]-N-methylbenzamide; and 6-(2,3-dichlorophenyl)-4-(4-hydroxy-3-methylphenyl)pyrimidin-2(1H)-one.

11. A pharmaceutical composition comprising the compound according to claim 1, and a pharmaceutically acceptable carrier, excipient, or diluent.

12. A method of inhibiting CK2 in a cell comprising contacting the cell, in which inhibition of CK2 is desired, with the compound according to claim 1.

13. A method of treating breast cancer comprising administering to a patient, in need of said treatment, the compound according to claim 1.

* * * * *